United States Patent [19]
Dryja et al.

[11] Patent Number: 5,498,521
[45] Date of Patent: Mar. 12, 1996

[54] DIAGNOSIS OF HEREDITARY RETINAL DEGENERATIVE DISEASES

[75] Inventors: Thaddeus P. Dryja, Milton; Eliot L. Berson, Boston, both of Mass.

[73] Assignee: President and Fellows of Harvard College, Cambridge, Mass.

[21] Appl. No.: 33,081

[22] Filed: Mar. 11, 1993

Related U.S. Application Data

[63] Continuation-in-part of Ser. No. 805,123, Dec. 11, 1991, Pat. No. 5,262,529, which is a continuation-in-part of Ser. No. 469,215, Jan. 24, 1990, Pat. No. 5,225,546.

[51] Int. Cl.$^6$ .......................... C07H 21/04; C12P 19/34; C12Q 1/68
[52] U.S. Cl. .......................... 435/6; 435/91.2; 536/24.31; 536/24.33; 935/77; 935/78
[58] Field of Search .................. 435/6, 91.2; 536/24.31, 536/24.33

[56] References Cited

U.S. PATENT DOCUMENTS

| | | | |
|---|---|---|---|
| 4,683,195 | 7/1987 | Mullis et al. | 435/6 |
| 4,736,866 | 4/1988 | Leder et al. | 800/2 |

OTHER PUBLICATIONS

Dryja et al., PNAS (USA) 88:9370–9374 (Oct. 1991).
Berson et al., Arch Ophthal 80:58–67, 1968, Rod Responses in Retinitis Pigmentosa, Dominantly Inherited.
Nie et al., Tissue Antigens 12:106–108, 1978, A New H–2–Linked Mutation, rds, Causing Retinal Degeneration in the Mouse.
Sanyal et al., The Journal of Comparative Neurology 194:193–207, 1980, Development and Degeneration of Retina in rds Mutant Mice: Light Microscopy.
Cohen, Investigative Ophthalmology & Visual Science 24:832–843, 1983, Some Cytological and Initial Biochemical Observations on Photoreceptors in Retinas of rds Mice.
Bunker et al., American Journal of Ophthalmology 97:357–365, 1984, Prevalence of Retinitis Pigmentosa in Maine.
Nathans et al., Proc. Natl. Acad. Sci. USA 81:4851–4855, 1984, Isolation and nucleotide sequence of the gene encoding human rhodopsin.
Medynski et al., Proc. Natl. Acad. Sci. USA 82:4311–4315, 1985, Amino acid sequence of the α subunit of transducin deduced from the cDNA sequence.
Lerea et al., Science 234:77–80, 1986, Identification of specific Transducin α Subunits in Retinal Rod and Cone Photoreceptors.
Nathans et al., Science 232:193–202, 1986, Molecular Genetics of Human Color Vision: The Genes Encoding Blue, Green, and Red Pigments.
Sparkes et al., Communication 797–798, 1986, Assignment of the rhodopsin gene to human chromosome three, region 3q21–3q24 by in situ hybridization studies.
Applebury et al., Vision Res. 26:1881–1895, 1986, Molecular Biology Of The Visual Pigments.
Sparkes et al., Invest. Ophthalmol Vis. Sci. 27:1170–1172, 1986, Assignment of the Rhodopsin Gene to Human Chromosome 3.
Nathans et al., Science 232:203–210, 1986, Molecular Genetics of Inherited Variation in Human Color Vision.
Yijian et al., Cytogenetics and Cell Genetics, p. 614, 1987, Human Gene Mapping 9.
Donis–Keller et al., Cell 51:319–337, 1987, A Genetic Linkage Map of the Human Genome.
Yamaki et al., FEB 234:39–43, 1988, The sequence of human retinal S–antigen reveals similarities with αtransducin.

(List continued on next page.)

*Primary Examiner*—Stephanie W. Zitomer
*Attorney, Agent, or Firm*—Fish & Richardson

[57] ABSTRACT

The invention generally provides a method of diagnosing in a human subject an increased likelihood of developing or transmitting to future generations a disease in which a mutant form of a human photoreceptor protein is a causative agent. The method involves analyzing the DNA of the subject to determine the presence or absence of a mutation in a gene for a photoreceptor protein.

17 Claims, 31 Drawing Sheets

OTHER PUBLICATIONS

Fong et al., J. Biol. Chem. 263:15330–15334, 1988, Internal Quadruplication in the Structure of Human Interstitial Retinol–binding Protein Deduced from Its Cloned cDNA*.

Tuteja et al., FEB 232:182–186, 1988, γ–Subunit of mouse retinal cyclic–GMP phosphodiesterase: cDNA and corresponding amino acid sequence.

Yandell et al., Cancer Cells 7:223–227, 1989, Direct Genomic Sequencing of Alleles at the Human Retinoblastoma Locus: Application to Cancer Diagnosis and Genetic Counseling.

Travis et al., Nature 338:70–73, 1989, Identification of photoreceptor–specific mRNA encoded by the gene responsible for retinal degeneration slow (rds).

Orita et al., Genomics 5:874–879, 1989, Rapid and Sensitive Detection of Point Mutations and DNA Polymorphisms Using the Polymerase Chain Reaction.

Chen et al., Am.J. Hum. Genet. 45:401–411, 1989, Linkage Heterogeneity between X–linked Retinitis Pigmentosa and a Map of 10 RFLP Loci.

Reichel et al., American Journal of Ophthalmology 108:540–547, 1989, An Electroretinographic and Molecular Genetic Study of X–Linked Cone Degeneration.

Weber et al., Am. J. Hum. Genet. 44:388–396, 1989, Abundant Class of Human DNA Polymorphisms Which Can Be Typed Using the Polymerase Chain Reaction.

McWilliam et al., Genomics 5:619–622, 1989, Autosomal Dominant Retinitis Pigmentosa (ADRP): Localization of an ADRP Gene to the Long Arm of Chromosome 3.

Begy et al., Nucleic Acids Research, 18:3058, 1990, Nucleotide and predicted protein sequence of rat retinal degeneration slow (rds).

Connell et al., Biochemistry 29:4691–4698, 1990, Molecular Cloning, Primary Structure, and Orientation of Vertebrate Photoreceptor Cell Protein Peripherin in the Rod Outer Segment Disk Membrane†, ‡.

Dryja et al., New England Journal of Medicine 323:1302–1307, 1990, Mutations Within The Rhodopsin Gene in Patients with Autosomal Dominant Retinitis Pigmentosa.

Dryja et al., Nature 343:364–366, 1990, A point mutation of the rhodopsin gene is one form of retinitis pigmentosa.

Travis et al., Genomics 10:733, 1991, The Human Retinal Degeneration Slow (RDS) Gene: Chromosome Assignment and Structure of the mRNA.

Travis et al., Neuron 6:61–70, 1991, The Retinal Degeneration Slow (rds) Gene Product Is a Photoreceptor Disc Membrane–Associated Glycoprotein.

Connell et al., Proc. Natl. Acad. Sic. USA 88:723–726, 1991, Photoreceptor peripherin is the normal product of the gene responsible for retinal degeneration in the rds mouse.

Bhattacharya et al., The Lancet 337:185, 1991, Retinitis pigmentosa and mutations in rhodopsin.

Sung et al., Proc. Natl. Acad. Sci. USA 88:6481–6485, 1991, Rhodopsin mutations in autosomal dominant retinitis pigmentosa.

Sheffield et al., Am. J. Hum. Genet. 49:699–706, 1991, Identification of Novel Rhodps in Mutations Associated with Retinitis Pigmentosa by GC–clamped Denaturing Gradient Gel Electrophoresis.

Keen et al., Genomics 11:199–205, 1991, Autosomal Dominant Retinitis Pigmentosa: Four New Mutations in Rhodopsin, One of Them in the Retinal Attachment Site.

Inglehearn et al., Am. J. Hum. Genet. 48:26–30, 1991, A 3–bp Deletion in the Rhodopsin Gene in a Family with Autosomal Dominant Retinitis Pigmentosa.

Gal et al., Genomics 11;468–470, 1991, Pro–347–Arg Mutation of the Rhodopsin Gene in Autosomal Dominant Retinitis Pigmentosa.

Berson et al., Arch Ophthalmol 109:92–100, 1991, Ocular Findings in Patients With Autosomal Dominant Retinitis Pigmentosa and a Rhodopsin Gene Defect (Pro–23–His).

Berson et al., American Journal of Ophthalmology 111:614–623, 1991, Ocular Findings in Patients With Autosomal Dominant Retinitis Pigmentosa and Rhodopsin, Proline–347–Leucine.

Dryja et al., Proc. Natl. Acad. Sci. USA 88:9370–9374, 1991, Mutation spectrum of the rhodopsin gene among patients with autosomal dominant retinitis pigmentosa.

Farrar et al., Genomics 11:1170–1171. 1991, Autosomal Dominant Retinitis Pigmentosa: A Mutation in Codon 178 of the Rhodopsin Gene in Two Families of Celtic Origin.

Sandberg et al., Investigative Ophthalmology & Visual Science, 31:2283–2287, 1990, Rod electroretinograms in an elevated cyclic guanosine monophosphate–type human retinal degeneration.

Tuteja et al., Gene 88:227–232, 1990, Isolation and characterization of cDNA encoding the gamma–subunit of cGMP phosphodiesterase in human retina.

Bowes et al., Nature 347:677–680, 1990, Retinal degeneration in the rd mouse is caused by a defect in the β subunit of rod cGMP–phosphodiesterase.

Collins et al., Genomics 13:698–704, 1992, The human β–subunit of rod photoreceptor cGMP phosphodiesterase: Complete retinal cDNA sequence and evidence for expression in brain.

Cotran et al., Exp. Eye Res. 53:557–564, 1991, Genetic analysis of patients with retinitis pigmentosa using a cloned cDNA probe for the human gamma subunit of cyclic GMP phosphodiesterase.

Weber et al., Nucleic Acids Research 19:6263–6268, 1991, Genomic organization and complete sequence of the human gene encoding the β–subunit of the cGMP phosphodiesterase and its localisation of 4p16.3.

Pittler et al., Proc. Natl. Acad. Sci. USA 88:;8322–8326, 1991, Identification of a nonsense mutation in the rod photoreceptor cGMP phosphodiesterase β–subunit gene of the rd mouse.

Olsson et al., Neuron 9:815–830, 1992, Transgenic mice with a rhodopsin mutation (Pro23His): A mouse model of autosomal dominant retinitis pigmentosa.

Kajiwara et al., Nature 354:480–483, 1991, Mutations in the human retinal degeneration slow gene in autosomal dominant retinitis pigmentosa.

Washburn et al., Journal of Biological Chemistry 264:15464–15466, 1989, Molecular defects in Drosophila rhodopsin mutants.

Charbonneau et al., Proc. Natl. Acad. Sci. USA 87:288–292, 1990, Identification of a noncatalytic cGMP–binding domain conserved in both the cGMP–stimulated and photoreceptor cyclic nucleotide phosphodiesterases.

Farber et al., J. Cyclic Nucleotide Research, 2;139–148, 1976, Enzymic Basis for Cyclic GMP accmulation in degenerative photoreceptor cells of mouse retina.

Ferrendelli et al., Biochemical/Biophysical Research Comm. 73:421–427, 1976, The effects of light and dark adaptation on the levels of cyclic nucleotides in retinas of mice heterozygous for a gene . . . .

Riess et al., nature Genetics 1;104–108, 1992, Exclusion of

DNA changes in the B–subunit of the c–GMP phosphodiesterase gene as the cause for Huntington's disease.
Riess et al., Am. J. Hum. Genet. 51:755–762, 1992, Search for Mutations in the Gene for the Beta subunit of the cGMP Phosphodiesterase (PDEB) in Patients with Autosomal Recessive Retinitis Pigmentosa.

GTATGAGCCG... Intron 1 ...TGCCTTGCAG

```
609                     624                     639                     654
TTC GGG CCC ACA GGA TGC AAT TTG GAG GGC TTC TTT GCC ACC CTG GGC GGT
Phe Gly Pro Thr Gly Cys Asn Leu Glu Gly Phe Phe Ala Thr Leu Gly Gly
                                                                120

2452                    2467                    2482
GAA ATT GCC CTG TGG TCC TTG GTG GTC CTG GCC ATC GAG CGG TAC GTG GTG
Glu Ile Ala Leu Trp Ser Leu Val Val Leu Ala Ile Glu Arg Tyr Val Val 2497                    2512                    2527                    2542
GTG TGT AAG CCC ATG AGC AAC TTC CGC TTC GGG GAG AAC CAT GCC ATC ATG
Val Cys Lys Pro Met Ser Asn Phe Arg Phe Gly Glu Asn His Ala Ile Met
        140

2557                    2572                    2587
GGC GTT GCC TTC ACC TGG GTC ATG GCG CTG GCC TGC GCC GCA CCC CCA CTC
Gly Val Ala Phe Thr Trp Val Met Ala Leu Ala Cys Ala Ala Pro Pro Leu
                160
```

GTAATGGCAC... Intron 2 ...CTGTCCTCAG

```
        2602                            3828                    3843
GCC GGC TGG TCC AGG TAC ATC CCC GAG GGC CTG CAG TGC TCG TGT GGA ATC
Ala Gly Trp Ser Arg Tyr Ile Pro Glu Gly Leu Gln Cys Ser Cys Gly Ile
                                180

3858                    3873                    3888
GAC TAC TAC ACG CTC AAG CCG GAG GTC AAC AAC GAG TCT TTT GTC ATC TAC
Asp Tyr Tyr Thr Leu Lys Pro Glu Val Asn Asn Glu Ser Phe Val Ile Tyr
                                                200

3903                    3918                    3933                    3948
ATG TTC GTG GTC CAC TTC ACC ATC CCC ATG ATT ATC ATC TTT TTC TGC TAT
Met Phe Val Val His Phe Thr Ile Pro Met Ile Ile Ile Phe Phe Cys Tyr
                                                                220
```

GTACGGGCCG... Intron 3 ...TGTCCTGCAG

```
        3963                    3978            4109
GGG CAG CTC GTC TTC ACC GTG AAG GAG GCC GCT GCC CAG CAG CAG GAG TCA
Gly Gln Leu Val Phe Thr Val Lys Glu Ala Ala Ala Gln Gln Gln Glu Ser
                                                                240
```

FIG. 1b

```
                4124                          4139                       4154                         4169
        GCC ACC ACA CAG AAG GCA GAG AAG GAG GTC ACC CGG ATG GTC ATC ATC ATG
        Ala Thr Thr Gln Lys Ala Glu Lys Glu Val Thr Arg Met Val Ile Ile Met 4184                        4199                     4214
        GTC ATC GCT TTC CTG ATC TGC TGG GTG CCC TAC GCC AGC GTG GCA TTC TAC
        Val Ile Ala Phe Leu Ile Cys Trp Val Pro Tyr Ala Ser Val Ala Phe Tyr
                260

4229                        4244                     4259
        ATC TTC ACC CAC CAG GGC TCC AAC TTC GGT CCC ATC TTC ATG ACC ATC CCA
        Ile Phe Thr His Gln Gly Ser Asn Phe Gly Pro Ile Phe Met Thr Ile Pro
                                        280

4274                        4289                          4304                     4319
        GCG TTC TTT GCC AAG AGC GCC GCC ATC TAC AAC CCT GTC ATC TAT ATC ATG
        Ala Phe Phe Ala Lys Ser Ala Ala Ile Tyr Asn Pro Val Ile Tyr Ile Met
                                                300

GTGCCTACTG... Intron 4 ...TGCCTTCCAG 4334                      5182                         5197
        ATG AAC AAG CAG TTC CGG AAC TGC ATG CTC ACC ACC ATC TGC TGC CGC AAG
        Met Asn Lys Gln Phe Arg Asn Cys Met Leu Thr Thr Ile Cys Cys Arg Lys
                                                        320

5212                      5227                   5242                     5257
        AAC CCA CTG GGT GAC GAT CAG GCC TCT GCT ACC GTG TCC AAG ACG GAG ACG
        Asn Pro Leu Gly Asp Asp Gln Ala Ser Ala Thr Val Ser Lys Thr Glu Thr
                                                                        340

5272           5285        5295        5305
        AGC CAG GTG GCC CCG GCC TAAGACCTGC CTAGGACTCT GTGGCCGACT
        Ser Gln Val Ala Pro Ala
                            348

5315          5325          5335         5345         5355         5365
        ATAGGCGTCT  CCCATCCCCT  ACACCTTCCC  CCAGCCACAG  CCATCCCACC  AGGAGCAGCG 5375          5385          5395         5405         5415         5425
        CCTGTGCAGA  ATGAACGAAG  TCACATAGGC  TCCTTAATTT  TTTTTTTTTT  TTTAAGAAAT 5435          5445          5455         5465         5475         5485
        AATTAATGAG  CTCCTCACT   CACCTGGGAC  AGCCTGAGAA  GGGACATCCA  CCAAGACCTA 5495          5505          5515         5525         5535         5545
        CTGATCTGGA  GTCCCACGTT  CCCCAAGGCC  AGCGGGATGT  GTGCCCCTCC  TCCTCCCAAC
```

FIG. 1c

```
          5555       5565       5575       5585       5595       5605
     TCATCTTTCA GGAACACGAG GATTCTTGCT TTCTGGAAAA GTGTCCCAGC TTAGGGATAA
                                                  ‾‾‾‾‾‾‾‾‾‾ ‾‾‾‾‾‾‾‾‾‾
          5615       5625       5635       5645       5655       5665
     GTGTCTAGCA CAGAATGGGG CACACAGTAG GTGCTTAATA AATGCTGGAT GGATGCAGGA
     ‾‾‾‾‾‾‾‾‾‾

5675       5685       5695       5705       5715       5725
     AGGAATGGAG GAATGAATGG GAAGGGAGAA CATATCTATC CTCTCAGACC CTCGCAGCAG 5735       5745       5755       5765       5775       5785
     CAGCAACTCA TACTTGGCTA ATGATATGGA GCAGTTGTTT TTCCCTCCCT GGGCCTCACT 5795       5805       5815       5825       5835       5845
     TTCTTCTCCT ATAAAATGGA AATCCCAGAT CCCTGGTCCT GCCGACACGC AGCTACTGAG 5855       5865       5875       5885       5895       5905
     AAGACCAAAA GAGGTGTGTG TGTGTCTATG TGTGTGTTTC AGCACTTTGT AAATAGCAAG 5915       5925       5935       5945       5955       5965
     AAGCTGTACA GATTCTAGTT AATGTTGTGA ATAACATCAA TTAATGTAAC TAGTTAATTA 5975       5985       5995       6005       6015       6025
     CTATGATTAT CACCTCCTGA TAGTGAACAT TTTGAGATTG GGCATTCAGA TGATGGGGTT 6035       6045       6055       6065       6075       6085
     TCACCCAACC TTGGGGCAGG TTTTTAAAAA TTAGCTAGGC ATCAAGGCCA GACCAGGGCT
```

FIG. 1d

```
      6095       6105       6115       6125       6135       6145
GGGGGTTGGG CTGTAGGCAG GGACAGTCAC AGGAATGCAG GATGCAGTCA TCAGACCTGA 6155       6165       6175       6185       6195       6205
AAAAACAACA CTGGGGGAGG GGGACGGTGA AGGCCAAGTT CCCAATGAGG GTGAGATTGG 6215       6225       6235       6245       6255       6265
GCCTGGGGTC TCACCCCTAG TGTGGGGCCC CAGGTCCCGT GCCTCCCCTT CCCAATGTGG 6275       6285       6295       6305       6315       6325
CCTATGGAGA GACAGGCCTT TCTCTCAGCC TCTGGAAGCC ACCTGCTCTT TTGCTCTAGC 6335       6345       6355       6365       6375       6385
ACCTGGGTCC CAGCATCTAG AGCATGGAGC CTCTAGAAGC CATGCTCACC CGCCCACATT 6395       6405       6415       6425       6435       6445
TAATTAACAG CTGAGTCCCT GATGTCATCC TTACTCGAAG AGCTTAGAAA CAAAGAGTGG 6455       6465       6475       6485       6495       6505
GAAATTCCAC TGGGCCTACC TTCCTTGGGG ATGTTCATGG GCCCCAGTTT CCAGTTTCCC 6515       6525       6535       6545       6555       6565
TTGCCAGACA AGCCCATCTT CAGCAGTTGC TAGTCCATTC TCCATTCTGG AGAATCTGCT
```

FIG. 1e

```
        6575       6585       6595       6605       6615       6625
CCAAAAAGCT GGCCACATCT CTGAGGTGTC AGAATTAAGC TGCCTCAGTA ACTGCTCCCC 6635       6645       6655       6665       6675       6685
CTTCTCCATA TAAGCAAAGC CAGAAGCTCT AGCTTTACCC AGCTCTGCCT GGAGACTAAG 6695       6705       6715       6725       6735       6745
GCAAATTGGG CCATTAAAAG CTCAGCTCCT ATGTTGGTAT TAACGGTGGT GGGTTTTGTT 6755       6765       6775       6785       6795       6805
GCTTTCACAC TCTATCCACA GGATAGATTG AAACTGCCAG CTTCCACCTG ATCCCTGACC 6815       6825       6835       6845       6855       6865
CTGGGATGGC TGGATTGAGC AATGAGCAGA GCCAAGCAGC ACAGAGTCCC CTGGGGCTAG 6875       6885       6895       6905       6915       6925
AGGTGGAGGA CGCAGTCCTG GGAATGGGAA AAACCCCAAC TTTGGGGTCA TAGAGGCACA 6935       6945
GGTAACCCAT AAAACTGCAA ACAAGCTT
```

FIG. 1f

```
GGATCCTGAG TACCTCTCCT CCCTGACCTC AGGCTTCCTC CTAGTGTCAC CTTGGCCCCT   60
CTTAGAAGCC AATTAGGCCC TCAGTTTCTG CAGCGGGGAT TAATATGATT ATGAACACCC  120
CCAATCTCCC AGATGCTGAT TCAGCCAGGA GCTTAGGAGG GGGAGGTCAC TTTATAAGGG  180
TCTGGGGGGG TCAGAACCCA GAGTCATCCA GCTGGAGCCC TGAGTGGCTG AGCTCAGGCC  240
TTCGCAGCAT TCTTGGGTGG GAGCAGCCAC GGGTCAGCCA CAAGGGCCAC AGCCATGAAT  300
GGCACAGAAG GCCCTAACTT CTACGTGCCC TTCTCCAATG CGACGGGTCT GGTACGCAGC  360
CCCTTCGAGT ACCCACAGTA CTACCTGGCT GAGCCATGGC AGTTCTCCAT GCTGGCCGCC  420
TACATGTTTC TGCTGATCGT GCTGGGCTTC CCCATCAACT TCCTCACGCT CTACGTCACC  480
GTCCAGCACA AGAAGCTGCG CACGCCTCTC AACTACATCC TGCTCAACCT AGCCGTGGCT  540
GACCTCTTCA TGGTCCTAGG TGGCTTCACC AGCACCCTCT ACACCTCTCT GCATGGATAC  600
TTCGTCTTCG GGCCCACAGG ATGCAATTTG GAGGGCTTCT TTGCCACCCT GGGCGGTATG  660
AGCCGGGTGT GGGTGGGGTG TGCAGGAGCC CGGGAGCATG GAGGGTCTG GAGAGTCCC  720
GGGCTTGGCG GTGGTGGCTG AGAGGCCTTC TCCCTTCTCC TGTCCTGTCA ATGTTATCCA  880
AAGCCCTCAT ATATTCAGTC AACAAACACC ATTCATGGTG ATAGCCGGGC TGCTGTTTGT  840
GCAGGGCTGG CACTGAACAC TGCCTTGATC TTATTTGGAG CAATATGCGC TTGTCTAATT  900
TCACAGCAAG AAAACTGAGC TGAGGCTCAA AGGCCAAGTC AAGCCCCTGC TGGGGCGTCA  960
GACAGGGACG GGTGCAGACT TGACTTGGAA GCCCGCATCT ATCTCGGGCC ATGTTTGCAG 1020
GACCAAGCCT CTGTTTCCCT TGGAGCAGCT GTGCTGAGTC AGACCCAGGC TGGGCACTGA 1080
GGGAGAGCTG GGCAAGCCAG ACCCCTCCTC TCTGGGGCC CAAGCTCAGG GTGGGAAGTG 1140
TGGCATCCTC TGCCTCCCCT CTCAGCCCCT GTCCTCAGGT GCCCCTCCAG CCTCCCTGCC 1200
GCGTTCCAAG TCTCCTGGTG TTGAGAACCG CAAGCAGCCG CTCTGAAGCA GTTCCTTTTT 1320
GCTTTAGAAT AATGTCTTGC ATTTAACAGG AAAACAGATG GGTGCTGCA GGATAACAG 1380
ATCCCACTTA ACAGAGAGGA AAACTGAGGC AGGGAGAGGG GAAGAGACTC ATTTAGGGAT 1400
GTGGCCAGGC AGCAACAAGA GCCTAGGTCT CCTGGCTGTG ATCCAGGAAT ATCTCTGCTG 1500
```

FIG. 2a

```
AGATGCAGGA GGAGACGCTA GAAGCAGCCA TTGCAAAGCT GGGTGACGGG GAGAGCTTAC 1560
CGCCAGCCAC AAGCGTCTCT CTGCCAGCCT TGCCCTGTCT CCCCCATGTC CAGGCTGCTG 1620
CCTCGGTCCC ATTCTCAGGG AATCTCTGGC CATTGTTGGG TGTTTGTTGC ATTCAATAAT 1680
CACAGATCAC TCAGTTCTGG CCAGAAGGTG GGTGTGCCAC TTACGGGTGG TTGTTCTCTG 1740
CAGGGTCAGT CCCAGTTTAC AAATATTGTC CCTTTCACTG TTAGGAATGT CCCAGTTTGG 1800
TTGATTAACT ATATGGCCAC TCTCCCTATG AAACTTCATG GGGTGGTGAG CAGGACAGAT 1860
GTTCGAATTC CATCATTTCC TTCTTCTTCC TCTGGGCAAA ACATTGCACA TTGCTTCATG 1920
GCTCCTAGGA GAGGCCCCCA CATGTCCGGG TTATTTCATT TCCCGAGAAG GGAGAGGGAG 1980
GAAGGACTGC CAATTCTGGG TTTCCACCAC CTCTGCATTC CTTCCCAACA AGGAACTCTG 2040
CCCCACATTA GGATGCATTC TTCTGCTAAA CACACACACA CACACACACA CACACACACA 2100
ACACACACAC ACACACACAC ACACACACAC AAAACTCCCT ACCGGGTTCC CAGTTCAATC 2160
CTGACCCCCT GATCTGATTC GTGTCCCTTA TGGGCCCAGA GCGCTAAGCA AATAACTTCC 2220
CCCATTCCCT GGAATTTCTT TGCCCAGCTC TCCTCAGCGT GTGGTCCCTC TGCCCCTTCC 2280
CCCTCCTCCC AGCACCAAGC TCTCTCCTTC CCAAGGCCT CCTCAAATCC CTCTCCCAGT 2340
CCTGGTTGCC TTCCTAGCTA CCCTCTCCCT GTCTAGGGGG GAGTGCACCC TCCTTAGGCA 2400
GTGGGGTCTG TGCTGACCGC CTGCTGACTG CCTTGCAGGT GAAATTGCCC TGTGGTCCTT 2460
GGTGGTCCTG GCCATCGAGC GGTACGTGGT GGTGTGTAAG CCCATGAGCA ACTTGGGCTT 2520
CGGGGAGAAC CATGCCATCA TGGGCGTTGC CTTCACCTGG GTCATGGCGC TGGCCTGCGC 2580
CGFFCTCTTT CTCGCCGGCT GGTCCAGGTA ATGGCACTGA GCAGAAGGGA AGAAGCTCCG 2640
GGGGCTCTTT GTAGGGTCCT CCAGTCAGGA CTCAAACCCA GTAGTGTCTG CTTCCAGGCA 2700
CTGACCTTGT ATGTCTCCTG GCCCAAATGC CCACTCAGGG TAGGGGTGTA GGGCAGAAGA 2760
AGAAACAGAC TCTAATGTTG CTACAAGGGC TGGTCCCATC TCCTGAGCCC CATGTCAAAC 2820
AGAATCCAAG ACATCCCAA CCTTCACCTT GGCTGTGCCC CTAATCCTCA ACTAAGCTAG 2880
GCGCAAATTC CAATCCTCTT TGGTCTAGTA CCCCGGGGGC AGCCCCTCT AACCTTGGGC 2940
GTCAGCAGCA GGGGAGGCCA CACCTTCGTA GTGCAGGTGG CCATATTGTG GCCCCTTGGA 3000
ACTGGGTCCC ACTCAGCCTC TAGGCGATTG TCTCCTAATG GGGCTGAGAT GAGACTCAGT 3060
GGGGACAGTG GTTTGGACAA TAGGACTGGT GACTCTGGTC CCCAGAGGCC TCATGTCCCT 3120
```

FIG. 2b

```
CTGTCTCCAG AAAATTCCCA CTCTCACTTC CCTTTCCTCC TCAGTCTTGC TAGGGTCCAT 3180
TTCTACCCCT TGCTGAATTT GAGCCCACCC CCTGGACTTT TTCCCCATCT TCTCCAATCT 3240
GGCCTAGTTC TATCCTCTGG AAGCAGAGCC GCTGGACGCT CTGGGTTTCC TGAGGCCCGT 3300
CCACTGTCAC CAATATCAGG AACCATTGCC ACGTCCTAAT GACGTGCGCT GGAAGCCTCT 3360
AGTTTCCAGA AGCTGCACAA AGATCCCTTA GATACTCTGT GTGTCCATCT TTGGCCTGGA 3420
AAATACTCTC ACCCTGGGGC TAGGAAGACC TCGGTTTGTA CAAACTTCCT CAAATGCAGA 3480
GCCTGAGGGC TCTCCCCACC TCCTCACCAA CCCTCTGCGT GGCATAGCCC TAGCCTCAGC 3540
GGGCAGTGGA TGCTGGGGCT GGGCATGCAG GGAGAGGCTG GGTGGTGTCA TCTGGTAACG 3600
CAGCCACCAA ACAATGAAGC GACACTGATT CCACAAGGTG CATCTGCATC CCATCTGAT 3660
CCATTCCATC CTGTCACCCA GCCATGCAGA CGTTTATGAT CCCCTTTTCC AGGGAGGGAA 3720
TGTGAAGCCC CAGAAAGGGC CAGGGCTCGG CAGCCACCTT GGCTGTTCCC AAGTCCCTCA 3780
CAGGCAGGGT CTCCCTACCT GCCTGTCCTC AGGTACATCC CCGAGGGCCT GCAGTGCTCG 3840
TGTGGAATCG ACTACTACAC GCTCAAGCCG GAGGTCAACA ACGAGTCTTT TGTCATCTAC 3900
ATGTTCGTGG TCCACTTCAC CATCCCCATG ATTATCATCT TTTTCTGCTA TGGGCAGCTC 3960
GTCTTCACCG TCAAGGAGGT ACGGGCCGGG GGTGGGCGG CCTCACGGCT CTGAGGGTCC 4020
AGCCCCCAGC ATGCATCTGC GGCTCCTGCT CCCTGGAGGA GCCATGGTCT GGACCCGGGT 4080
CCCGTGTCCT GCAGGCCGCT GCCCAGCAGC AGGAGTCAGC CACCACACAG AAGGCAGAGA 4140
AGGAGGTCAC CCGCATGGTC ATCATCATGG TCATCGCTTT CCTGAGCTGC TGGGTGCCCT 4200
ACGCCAGCGT GGCATTCTAC ATCTTCACCC ACCAGGGCTC CAACTTCGGT CCCATCTTCA 4260
TGACCATCCC AGCGTTCTTT GCCAAGAGCG CCGCCATCTA CAACCCTGTC ATCTATATCA 4320
TGATGAACAA GCAGGTGCCT ACTGCGGGTG GGAGGGCCCC AGTGCCCCAG GCCACAGGCG 4380
CTGCCTGCCA AGGACAAGCT ACTCCCAGGG CAGGGAGGG GCTCCATCAG GGTTACTGGC 4440
AGCAGTCTTG GGTCAGCAGT CCCAATGGGG AGTGTGTGAG AAATGCAGAT TCCTGGCCCC 4500
ACTCAGAACT GCTGAATCTC AGGGTGGGCC CAGGAACCTG CATTTCCAGC AAGCCCTCCA 4560
CAGGTGGCTC AGATGCTCAC TCAGGTGGGA GAAGCTCCAG TCAGCTAGTT CTGGAAGCCC 4620
AATGTCAAAG TCAGAAGGAC CCAAGTCGGG AATGGGATGG GCCAGTCTCC ATAAAGCTGA 4660
ATAAGGAGCT AAAAACTCTT ATTCTGAGGG GTAAAGGGGT AAAGGGTTCC TCGGAGAGGT 4740
```

FIG. 2c

```
ACCTCCGAGG GGTAAACAGT TGGGTAAACA GTCTCTGAAG TCAGCTCTGC CATTTTCTAG 4800
CTGTATGGCC CTGGGCAAGT CAATTTCCTT CTCTGTGCTT TGGTTTCCTC ATCCATAGAA 4860
AGGTAGAAAG GGCAAAACAC CAAACTCTTG CATTACAAGA GATAATTTAC AGAACACCCT 4920
TGGCACACAG AGGGCACCAT GAAATGTCAC GGGTGACACA GCCCCCTTGT GCTGAGTCCC 4980
TGGCATCTCT AGGGGTGAGG AGCGTCTGCC TAGCAGGTTC CCACCAGGAA GCTGGATTTG 5040
AGTGGATGGG GCGCTGGAAT CGTCAGGGGC AGAAGCAGGC AAAGGGTCGG GGCGAACCTC 5100
ACTAACGTGC CAGTTCCAAG TAGACAGTGG GCAGCCCTGG CCCTGACTCA AGCCTCTTGC 5160
GTTCCAGTTC CGGAACTGCA TGCTCACCAC CATCTGCTGC GGCAAGAACC CACTGGGTGA 5220
CGATGAGGCC TCTGCTACCG TGTCCAAGAC GGAGACGAGC CAGGTGGCCC CGGCCTAAGA 5280
CCTGCCTAGG ACTCTGTGGC CGACTATAGG CGTCTCCCAT CCCCTACACC TTCCCCCAGC 5340
CACAGCCATC CCACCAGGAG CAGCGCCTGT GCAGAATGAA CGAAGTCACA TAGGCTCCTT 5400
AATTTTTTTT TTTTTTTTAA GAAATAATTA TAGAGGCTCC TCACTCACCT GGGACA???? 5460
GAGAAGGGAC ATCCACCAAG ACCTACTGAT CTGGAGTCCC ACGTTCCCCA AGGCCAGCGG 5520
GATGTGTGCC CCTCCTCCTC CCAACTCATC TTTCAGGAAC ACGAGGATTC TTGCTTTCTG 5580
GAAAAGTGTC CCAGCTTAGG CATAAGTGTC TAGCACAGAA TGGGCACAC AGTAGGTGCT 5640
TAATAAATGC TGGATGGATG CAGGAAGGAA TGGAGGAATG AATGGGAAGG GAGAACATAT 5700
CTATCCTCTC AGACCCTCGC AGCAGCAGCA ACTCATACTT GGCTAATGAT ATGGAGCAGT 5760
TGTTTTTCCC TCCCTGGGCC TCACTTTCTT CTCCTATAAA ATGGAAATCC CAGATCCCTG 5820
GTCCTGCCGA CACGCAGCTA CTGAGAAGAC CAAAAGAGGT GTGTGTGTGT CTATGTGTGT 5880
GTTTCAGCAC TTTGTAAATA GCAAGAAGCT GTACAGATTC TAGTTAATGT TGTGAATAAC 5940
ATCAATTAAT CTAACTAGTT AATTACTATG ATTATCACCT CCTGATAGTG AACATTTGA 6000
GATTGGGCAT TCAGATGATG GGGTTTCACC CAACCTTGGG GCAGGTTTTT AAAAATTAGC 6060
TAGGCATCAA GGCCAGACCA GGGCTGGGGG TTGGGCTGTA GGCAGGGACA GTCACAGGAA 6120
TGCAGGATGC AGTCATCAGA CCTGAAAAAA CAACACTGGG GGAGGGGGAC GGTGAAGGCC 6180
AAGTTCCCAA TGAGGGTGAG ATTGGGCCTG GGTCTCACC CCTAGTGTGG GGCCCCAGGT 6240
CCCGTGCCTC CCCTTCCCAA TGTGGCCTAT GGAGAGACAG GCCTTTCTCT CAGCCTCTGG 6300
AAGCCACCTG CTCTTTTGCT CTAGCACCTG GGTCCCAGCA TCTAGAGCAT GGAGCCTCTA 6360
```

FIG. 2d

```
GAAGCCATGC TCACCCGCCC ACATTTAATT AACAGCTGAG TCCCTGATGT CATCCTTACT 6420

CGAAGAGCTT AGAAACAAAG AGTGGGAAAT TCCACTGGGC CTACCTTCCT TGGGGATGTT 6480

CATGGGCCCC AGTTTCCAGT TTCCCTTGCC AGACAAGCCC ATCTTCAGCA GTTGCTAGTC 6540

CATTCTCCAT TCTGGAGAAT CTGCTCCAAA AAGCTGGCCA CATCTCTGAG GTGTCAGAAT 6600

TAAGCTGCCT CAGTAACTGC TCCCCCTTCT CCATATAAGC AAAGCCAGAA GCTCTAGCTT 6660

TACCCAGCTC TGCCTGGAGA CTAAGGCAAA TTGGGCCATT AAAAGCTCAG CTCCTATGTT 6720

GGTATTAACG GTGGTGGGTT TTGTTGCTTT CACACTCTAT CCACAGGATA GATTGAAACT 6780

GCCAGCTTCC ACCTGATCCC TGACCCTGGG ATGGCTGGAT TGAGCAATGA GCAGAGCCAA 6840

GCAGCACAGA GTCCCTGGG GCTAGAGGTG GAGGAGGCAG TCCTGGGAAT GGGAAAAACC 6900

CCAACTTTGG GGTCATAGAG GCACAGGTAA CCCATAAAAC TGCAAACAAG CTT         6960
```

FIG. 2e (a) 5' − ACGCAGCCACTTCGAGTAC − 3'

(b) 5' − ACGCAGCCCCTTCGAGTAC − 3'

(c) 5' − CGCAGCCACTTCGAG − 3'

(d) 5' − CGCAGCCCCTTCGAG − 3'

```
              220              240                              260
5' GCTGGAGCCC TGAGTGGCTG AGCTCAGGCC TTCGCAGCAT TCTTGGGTGG
3  GACCTCGGG  ACTCACCGAC TCGAGTCCGG AAGCGTCGTA AGAACCCACC 280              300
   GAGCAGCCAC GGGTCAGCCA CAAGGGCCAC AGCCATGAAT
   CTCGTCGGTG CCCAGTCGGT GTTCCCGGTG TCGGTACTTA 320                        340
   GGCACAGAAG GCCCTAACTT CTACGTGCCC TTCTCCAATG CGACGGGTGT
   CCGTGTCTTC CGGGATTGAA GATGCACGGG AAGAGGTTAC GCTGCCCACA
                CODON
                 28
             360              380
   GGTACGCAGC CCCTTCGAGT ACCCACAGTA CTACCTGGCT              3'
   CCATGCGTCG GGGAAGCTCA TGGGTGTCAT GATGGACCGA              5'

TGAAGCTCA TGGGTGTCAT G           #502
                                              #485
```

FIG. 8

```
       10         20         30         40         50         60
CGGGGCTGTG CTGCACTTGA CCGCAGCAGG AGGGAGTCCA GGAGCCAAGG TTGCCGCGGT 70         80         90        100        110        120
GTCTCCGTCA GCCTCACCAT GAACCTGGAA CCGCCCAAGG CTGAGTTCCG GTCAGCCACC 130        140        150        160        170        180
AGGGTGGCCG GGGGACCTGT CACCCCCAGG AAAGGTCCCC CTAAATTTAA GCAGCGACAG 190        200        210        220        230        240
ACCAGGCAGT TCAAGAGCAA GCCCCCAAAG AAAGGCGTTC AAGGGTTTGG GGACGACATC 250        260        270        280        290        300
CCTGGAATGG AAGGCCTGGG AACAGACATC ACAGTCATCT GCCCTTGGGA GGCCTTCAAC 310        320        330        340        350        360
CACCTGGAGC TGCACGAGCT GGCCCAATAT GGCATCATCT AGCACGAGGC CCTGCTGAAG 370        380        390        400        410        420
TCCAGACCCT CCCCCTCCTG CCCACTGTGC TCTAAACCCT GCTCAGGATT CCTGTTGAGG 430        440        450        460        470        480
AGATGCCTCC CTAGCCCAGA TGGCACCTGG ACACCAGGAT GGGACTGCAA CCTCAGGTCT 490        500        510        520        530        540
CCCCCTACAT ATTAATACCA GTCACCAGGA GCCCACCACC TCCCTCTAGG ATGCCCCCTC 550        560        570        580        590        600
AGGGGCTGGC CAGGCCCTGC TCAACATCTG GAGATACAGG CCCACCCCTC AGTCCTGCCC 610        620        630        640        650        660
ACAGAGAGGC TTGGTCGGTC TCCACTCCCA GGGAGAACGG GAAGTGGACC CCAGCCCGGG 670        680        690        700        710        720
AGCCTGCTGG ACCCCAGATC GTCCCCTCCT CCCAGCTGGA AAGCTAGGGC AGGTCTCCCC 730        740        750        760        770        780
AGAGTGCTTC TGCACCCCAG CCCCCTGTCC TGCCTGTAAG GGGATACAGA GAAGCTCCCC 790        800        810        820        830        840
GTCTCTGCAT CCCTTCCCAG GGGGGTGCCC TTAGTTTGGA CATGCTGGGT AGCAGGACTC 850        860        870        880        890        900
CAGGGCGTGC ACGGTGAGCA GATGAGGCCC CAAGCTCATC ACACCAGGGG GCCATCCTTC 910        920        930        940        950        960
TCAATACAGG CTGCCCTTGC AGTCCCTATT TCAAAATAAA ATTAGTGTGT CCTTGCCAAA

970
AAAAAAAAAA AAA
```

FIG. 10

ATG AAC CTG GAA CCG CCC AAG GCT GAG TTC CGG TCA GCC ACC AGG GTG GCC GGG GGA CCT
Met Asn Leu Glu Pro Pro Lys Ala Glu Phe Arg Ser Ala Thr Arg Val Ala Gly Gly Pro

GTC ACC CCC AGG AAA GGT CCC CCT AAA TTT AAG CAG CGA CAG ACC AGG CAG TTC AAG AGC
Val Thr Pro Arg Lys Gly Pro Pro Lys Phe Lys Gln Arg Gln Thr Arg Gln Phe Lys Ser

AAG CCC CCA AAG AAA GGC GTT CAA GGG TTT GGG GAC ATC CCT GGA ATG GAA GGC CTG
Lys Pro Pro Lys Lys Gly Val Gln Gly Phe Gly Asp Asp Ile Pro Gly Met Glu Gly Leu

GGA ACA GAC ATC ACA GTC ATC TGC CCT TGG GAG GCC TTC AAC CAC CTG GAG CTG CAC GAG
Gly Thr Asp Ile Thr Val Ile Cys Pro Trp Glu Ala Phe Asn His Leu Glu Leu His Glu

CTG GCC CAA TAT GGC ATC ATC TAG
Leu Ala Gln Tyr Gly Ile Ile End

FIG. 11

SEQUENCE LISTING ( 1 ) GENERAL INFORMATION:

( i i i ) NUMBER OF SEQUENCES: 25

( 2 ) INFORMATION FOR SEQ ID NO: 1:

( i ) SEQUENCE CHARACTERISTICS:
( A ) LENGTH: 3016
( B ) TYPE: nucleic acid
( C ) STRANDEDNESS: double
( D ) TOPOLOGY: linear ( x i ) SEQUENCE DESCRIPTION: SEQ ID NO: 1:

```
GGATCCTGAG  TACCTCTCCT  CCCTGACCTC  AGGCTTCCTC  CTAGTGTCAC  CTTGGCCCCT        60

CTTAGAAGCC  AATTAGGCCC  TCAGTTTCTG  CAGCGGGGAT  TAATATGATT  ATGAACACCC       120

CCAATCTCCC  AGATGCTGAT  TCAGCCAGGA  GCTTAGGAGG  GGGAGGTCAC  TTTATAAGGG       180

TCTGGGGGGG  TCAGAACCCA  GAGTCATCCA  GCTGGAGCCC  TGAGTGGCTG  AGCTCAGGCC       240

TTCGCAGCAT  TCTTGGGTGG  GAGCAGCCAC  GGGTCAGCCA  CAAGGGCCAC  AGCC             294
```

| ATG | AAT | GGC | ACA | GAA | GGC | CCT | AAC | TTC | TAC | GTG | CCC | TTC | TCC | AAT | GCG | 342 |
|---|---|---|---|---|---|---|---|---|---|---|---|---|---|---|---|---|
| Met | Asn | Gly | Thr | Glu | Gly | Pro | Asn | Phe | Tyr | Val | Pro | Phe | Ser | Asn | Ala | |
| 1 | | | | 5 | | | | | 10 | | | | | 15 | | |

| ACG | GGT | GTG | GTA | CGC | AGC | CCC | TTC | GAG | TAC | CCA | CAG | TAC | TAC | CTG | GCT | 390 |
|---|---|---|---|---|---|---|---|---|---|---|---|---|---|---|---|---|
| Thr | Gly | Val | Val | Arg | Ser | Pro | Phe | Glu | Tyr | Pro | Gln | Tyr | Tyr | Leu | Ala | |
| | | | 20 | | | | | 25 | | | | | 30 | | | |

| GAG | CCA | TGG | CAG | TTC | TCC | ATG | CTG | GCC | GCC | TAC | ATG | TTT | CTG | CTG | ATC | 438 |
|---|---|---|---|---|---|---|---|---|---|---|---|---|---|---|---|---|
| Glu | Pro | Trp | Gln | Phe | Ser | Met | Leu | Ala | Ala | Tyr | Met | Phe | Leu | Leu | Ile | |
| | | 35 | | | | | 40 | | | | | 45 | | | | |

| GTG | CTG | GGC | TTC | CCC | ATC | AAC | TTC | CTC | ACG | CTC | TAC | GTC | ACC | GTC | CAG | 486 |
|---|---|---|---|---|---|---|---|---|---|---|---|---|---|---|---|---|
| Val | Leu | Gly | Phe | Pro | Ile | Asn | Phe | Leu | Thr | Leu | Tyr | Val | Thr | Val | Gln | |
| | 50 | | | | | 55 | | | | | 60 | | | | | |

| CAC | AAG | AAG | CTG | CGC | ACG | CCT | CTC | AAC | TAC | ATC | CTG | CTC | AAC | CTA | GCG | 534 |
|---|---|---|---|---|---|---|---|---|---|---|---|---|---|---|---|---|
| His | Lys | Lys | Leu | Arg | Thr | Pro | Leu | Asn | Tyr | Ile | Leu | Leu | Asn | Leu | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| GTG | GCT | GAC | CTC | TTC | ATG | GTC | CTA | GGT | GGC | TTC | ACC | AGC | ACC | CTC | TAC | 582 |
| Val | Ala | Asp | Leu | Phe | Met | Val | Leu | Gly | Gly | Phe | Thr | Ser | Thr | Leu | Tyr | |
| | | | | 85 | | | | 90 | | | | | | 95 | | |
| ACC | TCT | CTG | CAT | GGA | TAC | TTC | GTC | TTC | GGG | CCC | ACA | GGA | TGC | AAT | TTG | 630 |
| Thr | Ser | Leu | His | Gly | Tyr | Phe | Val | Phe | Gly | Pro | Thr | Gly | Cys | Asn | Leu | |
| | | | 100 | | | | | 105 | | | | | 110 | | | |
| GAG | GGC | TTC | TTT | GCC | ACC | CTG | GGC | GGT | GAA | ATT | GCC | CTG | TGG | TCC | TTG | 678 |
| Glu | Gly | Phe | Phe | Ala | Thr | Leu | Gly | Gly | Glu | Ile | Ala | Leu | Trp | Ser | Leu | |
| | | 115 | | | | | 120 | | | | | 125 | | | | |
| GTG | GTC | CTG | GCC | ATC | GAG | CGG | TAC | GTG | GTG | GTG | TGT | AAG | CCC | ATG | AGC | 726 |
| Val | Val | Leu | Ala | Ile | Glu | Arg | Tyr | Val | Val | Val | Cys | Lys | Pro | Met | Ser | |
| | 130 | | | | | 135 | | | | | 140 | | | | | |
| AAC | TTC | CGC | TTC | GGG | GAG | AAC | CAT | GCC | ATC | ATG | GGC | GTT | GCC | TTC | ACC | 774 |
| Asn | Phe | Arg | Phe | Gly | Glu | Asn | His | Ala | Ile | Met | Gly | Val | Ala | Phe | Thr | |
| 145 | | | | | 150 | | | | | 155 | | | | | 160 | |
| TGG | GTC | ATG | GCG | CTG | GCC | TGC | GCC | GCA | CCC | CCA | CTC | GCC | GGC | TGG | TCC | 822 |
| Trp | Val | Met | Ala | Leu | Ala | Cys | Ala | Ala | Pro | Pro | Leu | Ala | Gly | Trp | Ser | |
| | | | | 165 | | | | | 170 | | | | | 175 | | |
| AGG | TAC | ATC | CCC | GAG | GGC | CTG | CAG | TGC | TCG | TGT | GGA | ATC | GAC | TAC | TAC | 870 |
| Arg | Tyr | Ile | Pro | Glu | Gly | Leu | Gln | Cys | Ser | Cys | Gly | Ile | Asp | Tyr | Tyr | |
| | | | 180 | | | | | 185 | | | | | 190 | | | |
| ACG | CTC | AAG | CCG | GAG | GTC | AAC | AAC | GAG | TCT | TTT | GTC | ATC | TAC | ATG | TTC | 918 |
| Thr | Leu | Lys | Pro | Glu | Val | Asn | Asn | Glu | Ser | Phe | Val | Ile | Tyr | Met | Phe | |
| | | 195 | | | | | 200 | | | | | 205 | | | | |
| GTG | GTC | CAC | TTC | ACC | ATC | CCC | ATG | ATT | ATC | ATC | TTT | TTC | TGC | TAT | GGG | 966 |
| Val | Val | His | Phe | Thr | Ile | Pro | Met | Ile | Ile | Ile | Phe | Phe | Cys | Tyr | Gly | |
| | 210 | | | | | 215 | | | | | 220 | | | | | |
| CAG | CTC | GTC | TTC | ACC | GTC | AAG | GAG | GCC | GCT | GCC | CAG | CAG | CAG | GAG | TCA | 1014 |
| Gln | Leu | Val | Phe | Thr | Val | Lys | Glu | Ala | Ala | Ala | Gln | Gln | Gln | Glu | Ser | |
| 225 | | | | | 230 | | | | | 235 | | | | | 240 | |
| GCC | ACC | ACA | CAG | AAG | GCA | GAG | AAG | GAG | GTC | ACC | CGG | ATG | GTC | ATC | ATC | 1062 |
| Ala | Thr | Thr | Gln | Lys | Ala | Glu | Lys | Glu | Val | Thr | Arg | Met | Val | Ile | Ile | |
| | | | | 245 | | | | | 250 | | | | | 255 | | |
| ATG | GTC | ATC | GCT | TTC | CTG | ATC | TGC | TGG | GTG | CCC | TAC | GCC | AGC | GTG | GCA | 1110 |
| Met | Val | Ile | Ala | Phe | Leu | Ile | Cys | Trp | Val | Pro | Tyr | Ala | Ser | Val | Ala | |
| | | | 260 | | | | | 265 | | | | | 270 | | | |
| TTC | TAC | ATC | TTC | ACC | CAC | CAG | GGC | TCC | AAC | TTC | GGT | CCC | ATC | TTC | ATG | 1158 |
| Phe | Tyr | Ile | Phe | Thr | His | Gln | Gly | Ser | Asn | Phe | Gly | Pro | Ile | Phe | Met | |
| | | 275 | | | | | 280 | | | | | 285 | | | | |
| ACC | ATC | CCA | GCG | TTC | TTT | GCC | AAG | AGC | GCC | GCC | ATC | TAC | AAC | CCT | GTC | 1206 |
| Thr | Ile | Pro | Ala | Phe | Phe | Ala | Lys | Ser | Ala | Ala | Ile | Tyr | Asn | Pro | Val | |
| | 290 | | | | | 295 | | | | | 300 | | | | | |
| ATC | TAT | ATC | ATG | ATG | AAC | AAG | CAG | TTC | CGG | AAC | TGC | ATG | CTC | ACC | ACC | 1254 |
| Ile | Tyr | Ile | Met | Met | Asn | Lys | Gln | Phe | Arg | Asn | Cys | Met | Leu | Thr | Thr | |
| 305 | | | | | 310 | | | | | 315 | | | | | 320 | |
| ATC | TGC | TGC | CGC | AAG | AAC | CCA | CTG | GGT | GAC | GAT | CAG | GCC | TCT | GCT | ACC | 1302 |
| Ile | Cys | Cys | Gly | Lys | Asn | Pro | Leu | Gly | Asp | Asp | Gln | Ala | Ser | Ala | Thr | |
| | | | | 325 | | | | | 330 | | | | | 335 | | |
| GTG | TCC | AAG | ACG | GAG | ACG | AGC | CAG | GTG | GCC | CCG | GCC | | | | | 1338 |
| Val | Ser | Lys | Thr | Glu | Thr | Ser | Gln | Val | Ala | Pro | Ala | | | | | |
| | | | 340 | | | | | 345 | | | | | | | | |

```
TAAGACCTGC CTAGGACTCT GTGGCCGACT                                           1368

ATAGGCGTCT CCCATCCCCT ACACCTTCCC CCAGCCACAG CCATCCCACC AGGAGCAGCG          1428

CCTGTGCAGA ATGAACGAAG TCACATAGGC TCCTTAATTT TTTTTTTTTT TTTAAGAAAT          1488

AATTAATGAG GCTCCTCACT CACCTGGGAC AGCCTGAGAA GGGACATCCA CCAAGACCTA          1548

CTGATCTGGA GTCCCACGTT CCCCAAGGCC AGCGGGATGT GTGCCCCTCC TCCTCCCAAC          1608

TCATCTTTCA GGAACACGAG GATTCTTGCT TTCTGGAAAA GTGTCCCAGC TTAGGGATAA          1668
```

| | | | | | | |
|---|---|---|---|---|---|---|
| GTGTCTAGCA | CAGAATGGGG | CACACAGTAG | GTGCTTAATA | AATGCTGGAT | GGATGCAGGA | 1728 |
| AGGAATGGAG | GAATGAATGG | GAAGGGAGAA | CATATCTATC | CTCTCAGACC | CTCGCAGCAG | 1788 |
| CAGCAACTCA | TACTTGGCTA | ATGATATGGA | GCAGTTGTTT | TTCCCTCCCT | GGGCCTCACT | 1848 |
| TTCTTCTCCT | ATAAATGGA | AATCCCAGAT | CCCTGGTCCT | GCCGACACGC | AGCTACTGAG | 1908 |
| AAGACCAAAA | GAGGTGTGTG | TGTGTCTATG | TGTGTGTTTC | AGCACTTTGT | AAATAGCAAG | 1968 |
| AAGCTGTACA | GATTCTAGTT | AATGTTGTGA | ATAACATCAA | TTAATGTAAC | TAGTTAATTA | 2028 |
| CTATGATTAT | CACCTCCTGA | TAGTGAACAT | TTTGAGATTG | GCATTCAGA | TGATGGGGTT | 2088 |
| TCACCCAACC | TTGGGGCAGG | TTTTTAAAAA | TTAGCTAGGC | ATCAAGGCCA | GACCAGGGCT | 2148 |
| GGGGGTTGGG | CTGTAGGCAG | GGACAGTCAC | AGGAATGCAG | GATGCAGTCA | TCAGACCTGA | 2208 |
| AAAACAACA | CTGGGGGAGG | GGGACGGTGA | AGGCCAAGTT | CCCAATGAGG | GTGAGATTGG | 2268 |
| GCCTGGGGTC | TCACCCCTAG | TGTGGGGCCC | CAGGTCCCGT | GCCTCCCTT | CCCAATGTGG | 2328 |
| CCTATGGAGA | GACAGGCCTT | TCTCTCAGCC | TCTGGAAGCC | ACCTGCTCTT | TTGCTCTAGC | 2388 |
| ACCTGGGTCC | CAGCATCTAG | AGCATGGAGC | CTCTAGAAGC | CATGCTCACC | CGCCCACATT | 2448 |
| TAATTAACAG | CTGAGTCCCT | GATGTCATCC | TTACTCGAAG | AGCTTAGAAA | CAAAGAGTGG | 2508 |
| GAAATTCCAC | TGGGCCTACC | TTCCTTGGGG | ATGTTCATGG | GCCCAGTTT | CCAGTTTCCC | 2568 |
| TTGCCAGACA | AGCCCATCTT | CAGCAGTTGC | TAGTCCATTC | TCCATTCTGG | AGAATCTGCT | 2628 |
| CCAAAAAGCT | GGCCACATCT | CTGAGGTGTC | AGAATTAAGC | TGCCTCAGTA | ACTGCTCCCC | 2688 |
| CTTCTCCATA | TAAGCAAAGC | CAGAAGCTCT | AGCTTACCC | AGCTCTGCCT | GGAGACTAAG | 2748 |
| GCAAATTGGG | CCATTAAAAG | CTCAGCTCCT | ATGTTGGTAT | TAACGGTGGT | GGGTTTGTT | 2808 |
| GCTTTCACAC | TCTATCCACA | GGATAGATTG | AAACTGCCAG | CTTCCACCTG | ATCCCTGACC | 2868 |
| CTGGGATGGC | TGGATTGAGC | AATGAGCAGA | GCCAAGCAGC | ACAGAGTCCC | CTGGGGCTAG | 2928 |
| AGGTGGAGGA | CGCAGTCCTG | GGAATGGGAA | AAACCCCAAC | TTTGGGGTCA | TAGAGGCACA | 2988 |
| GGTAACCCAT | AAAACTGCAA | ACAAGCTT | | | | 3016 |

( 2 ) INFORMATION FOR SEQ ID NO: 2:

( i ) SEQUENCE CHARACTERISTICS:
( A ) LENGTH: 6953
( B ) TYPE: nucleic acid
( C ) STRANDEDNESS: double
( D ) TOPOLOGY: linear ( x i ) SEQUENCE DESCRIPTION: SEQ ID NO: 2:

| | | | | | | |
|---|---|---|---|---|---|---|
| GGATCCTGAG | GACCTCTCCT | CCCTGACCTC | AGGCTTCCTC | CTAGTGTCAC | CTTGGCCCCT | 60 |
| CTTAGAAGCC | AATTAGGCCC | TCAGTTTCTG | CAGCGGGGAT | TAATATGATT | ATGAACACCC | 120 |
| CCAATCTCCC | AGATGCTGAT | TCAGCCAGGA | GCTTAGGAGG | GGGAGGTCAC | TTTATAAGGG | 180 |
| TCTGGGGGGG | TCAGAACCCA | GAGTCATCCA | GCTGGAGCCC | TGAGTGGCTG | AGCTCAGGCC | 240 |
| TTCGCAGCAT | TCTTGGGTGG | GAGCAGCCAC | GGGTCAGCCA | CAAGGGCCAC | AGCCATGAAT | 300 |
| GGCACAGAAG | GCCCTAACTT | CTACGTGCCC | TTCTCCATTG | CGACGGGTGT | GGTACGCAGC | 360 |
| CCCTTCGAGT | ACCCACAGTA | CTACCTGGCT | GAGCCATGGC | AGTTCTCCAT | GCTGGCCGCC | 420 |
| TACATGTTTC | TGCTGATCGT | GCTGGGCTTC | CCCATCAACT | TCCTCACGCT | CTACGTCACC | 480 |
| GTCCAGCACA | AGAAGCTGCG | CACGCCTCTC | AACTACATCC | TGCTCAACCT | AGCCGTGGCT | 540 |
| GACCTCTTCA | TGGTCCTAGG | TGGCTTCACC | AGCACCCTCT | ACACCTCTCT | GCATGGATAC | 600 |
| TTCGTCTTCG | GGCCCACAGG | ATGCAATTTG | GAGGGCTTCT | TTGCCACCCT | GGGCGGTATG | 660 |
| AGCCGGGTGT | GGGTGGGGTG | TGCAGGAGCC | CGGGAGCATG | GAGGGTCTG | GGAGAGTCCC | 720 |

```
GGGCTTGGCG GTGGTGGCTG AGAGGCCTTC TCCCTTCTCC TGTCCTGTCA ATGTTATCCA      780
AAGCCCTCAT ATATTCAGTC AACAAACACC ATTCATGGTG ATAGCCGGGC TGCTGTTTGT      840
GCAGGGCTGG CACTGAACAC TGCCTTGATC TTATTTGGAG CAATATGCGC TTGTCTAATT      900
TCACAGCAAG AAAACTGAGC TGAGGCTCAA AGGCCAAGTC AAGCCCCTGC TGGGGCGTCA      960
CACAGGGACG GGTGCAGAGT TGAGTTGGAA GCCCGCATCT ATCTCGGGCC ATGTTTGCAG     1020
CACCAAGCCT CTGTTTCCCT TGGAGCAGCT GTGCTGAGTC AGACCCAGGC TGGGCACTGA     1080
GGGAGAGCTG GGCAAGCCAG ACCCCTCCTC TCTGGGGGCC CAAGCTCAGG GTGGGAAGTG     1140
GATTTTCCAT TCTCCAGTCA TTGGGTCTTC CCTGTGCTGG GCAATGGGCT CGGTCCCCTC     1200
TGGCATCCTC TGCCTCCCCT CTCAGCCCCT GTCCTCAGGT GCCCTCCAG CCTCCCTGCC      1260
GCGTTCCAAG TCTCCTGGTG TTGAGAACCG CAAGCAGCCG CTCTGAAGCA GTTCCTTTTT     1320
GCTTTAGAAT AATGTCTTGC ATTTAACAGG AAAACAGATG GGTGCTGCA GGATAACAG       1380
ATCCCACTTA ACAGAGAGGA AAACTGAGGC AGGGAGAGGG AAGAGACTC ATTTAGGGAT      1440
GTGGCCAGGC AGCAACAAGA GCCTAGGTCT CCTGGCTGTG ATCCAGGAAT ATCTCTGCTG     1500
AGATGCAGGA GGAGACGCTA GAAGCAGCCA TTGCAAAGCT GGGTGACGGG GAGAGCTTAC     1560
CGCCAGCCAC AAGCGTCTCT CTGCCAGCCT TGCCCTGTCT CCCCATGTC CAGGCTGCTG      1620
CCTCGGTCCC ATTCTCAGGG AATCTCTGGC CATTGTTGGG TGTTTGTTGC ATTCAATAAT    1680
CACAGATCAC TCAGTTCTGG CCAGAAGGTG GGTGTGCCAC TTACGGGTGG TTGTTCTCTG     1740
CAGGGTCAGT CCCAGTTTAC AAATATTGTC CCTTTCACTG TTAGGAATGT CCCAGTTTGG     1800
TTGATTAACT ATATGGCCAC TCTCCCTATG AAACTTCATG GGTGGTGAG CAGGACAGAT      1860
GTTCGAATTC CATCATTTCC TTCTTCTTCC TCTGGGCAAA ACATTGCACA TTGCTTCATG     1920
GCTCCTAGGA GAGGCCCCCA CATGTCCGGG TTATTTCATT TCCCGAGAAG GGAGAGGGAG    1980
GAAGGACTGC CAATTCTGGG TTTCCACCAC CTCTGCATTC CTTCCCAACA AGGAACTCTG    2040
CCCCACATTA GGATGCATTC TTCTGCTAAA CACACACACA CACACACACA CACACAACAC    2100
ACACACACAC ACACACACAC ACACACACAC AAAACTCCCT ACCGGGTTCC CAGTTCAATC    2160
CTGACCCCCT GATCTGATTC GTGTCCCTTA TGGGCCCAGA GCGCTAAGCA ATAACTTCC     2220
CCCATTCCCT GGAATTTCTT TGCCCAGCTC TCCTCAGCGT GTGGTCCCTC TGCCCCTTCC    2280
CCCTCCTCCC AGCACCAAGC TCTCTCCTTC CCAAGGCCT CCTCAAATCC CTCTCCCACT     2340
CCTGGTTGCC TTCCTAGCTA CCCTCTCCCT GTCTAGGGGG GAGTGCACCC TCCTTAGGCA    2400
GTGGGGTCTG TGCTGACCGC CTGCTGACTG CCTTGCAGGT GAAATTGCCC TGTGGTCCTT    2460
GGTGGTCCTG GCCATCGAGC GGTACGTGGT GGTGTGTAAG CCCATGAGCA ACTTCCGCTT    2520
CGGGGAGAAC CATGCCATCA TGGGCGTTGC CTTCACCTGG GTCATGGCGC TGGCCTGCGC    2580
CGCACCCCCA CTCGCCGGCT GGTCCAGGTA ATGGCACTGA GCAGAAGGGA AGAAGCTCCG    2640
GGGGCTCTTT GTAGGGTCCT CCAGTCAGGA CTCAAACCCA GTAGTGTCTG GTTCCAGGCA    2700
CTGACCTTGT ATGTCTCCTG GCCCAAATGC CCACTCAGGG TAGGGTGTA GGGCAGAAGA     2760
AGAAACAGAC TCTAATGTTG CTACAAGGGC TGGTCCCATC TCCTGAGCCC CATGTCAAAC    2820
AGAATCCAAG ACATCCCAAC CCTTCACCTT GGCTGTGCCC CTAATCCTCA ACTAAGCTAG    2880
GCGCAAATTC CAATCCTCTT TGGTCTAGTA CCCCGGGGGC AGCCCCTCT AACCTTGGGC     2940
CTCAGCAGCA GGGGAGGCCA CACCTTCCTA GTGCAGGTGG CCATATTGTG GCCCCTTGGA    3000
ACTGGGTCCC ACTCAGCCTC TAGGCGATTG TCTCCTAATG GGGCTGAGAT GAGACTCAGT    3060
GGGGACAGTG GTTTGGACAA TAGGACTGGT GACTCTGGTC CCCAGAGGCC TCATGTCCCT    3120
```

| | | | | | |
|---|---|---|---|---|---|
| CTGTCTCCAG | AAAATTCCCA | CTCTCACTTC | CCTTTCCTCC | TCAGTCTTGC | TAGGGTCCAT 3180 |
| TTCTACCCCT | TGCTGAATTT | GAGCCCACCC | CCTGGACTTT | TTCCCCATCT | TCTCCAATCT 3240 |
| GGCCTAGTTC | TATCCTCTGG | AAGCAGAGCC | GCTGGACGCT | CTGGGTTTCC | TGAGGCCCGT 3300 |
| CCACTGTCAC | CAATATCAGG | AACCATTGCC | ACGTCCTAAT | GACGTGCGCT | GGAAGCCTCT 3360 |
| AGTTTCCAGA | AGCTGCACAA | AGATCCCTTA | GATACTCTGT | GTGTCCATCT | TTGGCCTGGA 3420 |
| AAATACTCTC | ACCCTGGGGC | TAGGAAGACC | TCGGTTTGTA | CAAACTTCCT | CAAATGCAGA 3480 |
| GCCTGAGGGC | TCTCCCCACC | TCCTCACCAA | CCCTCTGCGT | GGCATAGCCC | TAGCCTCAGC 3540 |
| GGGCAGTGGA | TGCTGGGGCT | GGGCATGCAG | GGAGAGGCTG | GGTGGTGTCA | TCTGGTAACG 3600 |
| CAGCCACCAA | ACAATGAAGC | GACACTGATT | CCACAAGGTG | CATCTGCATC | CCATCTGAT 3660 |
| CCATTCCATC | CTGTCACCCA | GCCATGCAGA | CGTTTATGAT | CCCCTTTTCC | AGGGAGGGAA 3720 |
| TGTGAAGCCC | CAGAAAGGGC | CAGCGCTCGG | CAGCCACCTT | GGCTGTTCCC | AAGTCCCTCA 3780 |
| CAGGCAGGGT | CTCCCTACCT | GCCTGTCCTC | AGGTACATCC | CCGAGGGCCT | GCAGTGCTCG 3840 |
| TGTGGAATCG | ACTACTACAC | GCTCAAGCCG | GAGGTCAACA | ACGAGTCTTT | TGTCATCTAC 3900 |
| ATGTTCGTGG | TCCACTTCAC | CATCCCCATG | ATTATCATCT | TTTTCTGCTA | TGGGCAGCTC 3960 |
| GTCTTCACCG | TCAAGGAGGT | ACGGGCCGGG | GGGTGGGCGG | CCTCACGGCT | CTGAGGGTCC 4020 |
| AGCCCCCAGC | ATGCATCTGC | GGCTCCTGCT | CCCTGGAGGA | GCCATGGTCT | GGACCCGGGT 4080 |
| CCCGTGTCCT | GCAGGCCGCT | GCCCAGCAGC | AGGAGTCAGC | CACCACACAG | AAGGCAGAGA 4140 |
| AGGAGGTCAC | CCGCATGGTC | ATCATCATGG | TCATCGCTTT | CCTGATCTGC | TGGGTGCCCT 4200 |
| ACGCCAGCGT | GGCATTCTAC | ATCTTCACCC | ACCAGGGCTC | CAACTTCGGT | CCCATCTTCA 4260 |
| TGACCATCCC | AGCGTTCTTT | GCCAAGAGCG | CCGCCATCTA | CAACCCTGTC | ATCTATATCA 4320 |
| TGATGAACAA | GCAGGTGCCT | ACTGCGGGTG | GGAGGGCCCC | AGTGCCCAG | GCCACAGGCG 4380 |
| CTGCCTGCCA | AGGACAAGCT | ACTCCCAGGG | CAGGGAGGG | GCTCCATCAG | GGTTACTGGC 4440 |
| AGCAGTCTTG | GGTCAGCAGT | CCCAATGGGG | AGTGTGTGAG | AAATGCAGAT | TCCTGGCCCC 4500 |
| ACTCAGAACT | GCTGAATCTC | AGGGTGGGCC | CAGGAACCTG | CATTTCCAGC | AAGCCCTCCA 4560 |
| CAGGTGGCTC | AGATGCTCAC | TCAGGTGGGA | GAAGCTCCAG | TCAGCTAGTT | CTGGAAGCCC 4620 |
| AATGTCAAAG | TCAGAAGGAC | CCAAGTCGGG | AATGGGATGG | GCCAGTCTCC | ATAAAGCTGA 4680 |
| ATAAGGAGCT | AAAAAGTCTT | ATTCTGAGGG | GTAAAGGGGT | AAAGGGTTCC | TCGGAGAGGT 4740 |
| ACCTCCGAGG | GGTAAACAGT | TGGGTAAACA | GTCTCTGAAG | TCAGCTCTGC | CATTTTCTAG 4800 |
| CTGTATGGCC | CTGGGCAAGT | CAATTTCCTT | CTCTGTGCTT | TGGTTTCCTC | ATCCATAGAA 4860 |
| AGGTAGAAAG | GGCAAAACAC | CAAACTCTTG | GATTACAAGA | GATAATTTAC | AGAACACCCT 4920 |
| TGGCACACAG | AGGGCACCAT | GAAATGTCAC | GGGTGACACA | GCCCCTTGT | GCTCAGTCCC 4980 |
| TGGCATCTCT | AGGGGTGAGG | AGCGTCTGCC | TAGCAGGTTC | CCACCAGGAA | GCTGGATTTG 5040 |
| AGTGGATGGG | GCGCTGGAAT | CGTGAGGGGC | AGAAGCAGGC | AAAGGGTCGG | GGCGAACCTC 5100 |
| ACTAACGTGC | CAGTTCCAAG | CACACTGTGG | GCAGCCCTGG | CCCTGACTCA | AGCCTCTTGC 5160 |
| CTTCCAGTTC | CGGAACTGCA | TGCTCACCAC | CATCTGCTGC | GGCAAGAACC | CACTGGGTGA 5220 |
| CGATGAGGCC | TCTGCTACCG | TGTCCAAGAC | GGAGACGAGC | CAGGTGGCCC | CGGCCTAAGA 5280 |
| CCTGCCTAGG | ACTCTGTGGC | CGACTATAGG | CGTCTCCCAT | CCCTACACC | TTCCCCAGC 5340 |
| CACAGCCATC | CCACCAGGAG | CAGCGCCTGT | GCAGAATGAA | CGAAGTCACA | TAGGCTCCTT 5400 |
| AATTTTTTTT | TTTTTTTTAA | GAAATAATTA | ATGAGGCTCC | TCACTCACCT | GGGACAGCCT 5460 |
| GAGAAGGGAC | ATCCACCAAG | ACCTACTGAT | CTGGAGTCCC | ACGTTCCCCA | AGGCAGCGG 5520 |

```
GATGTGTGCC CCTCCTCCTC CCAACTCATC TTTCAGGAAC ACGAGGATTC TTGCTTTCTG    5580

GAAAAGTGTC CCAGCTTAGG GATAAGTGTC TAGCACAGAA TGGGGCACAC AGTAGGTGCT    5640

TAATAAATGC TGGATGGATG CAGGAAGGAA TGGAGGAATG AATGGGAAGG GAGAACATAT    5700

CTATCCTCTC AGACCCTCGC AGCAGCAGCA ACTCATACTT GGCTAATGAT ATGGAGCAGT    5760

TGTTTTTCCC TCCCTGGGCC TCACTTTCTT CTCCTATAAA ATGGAAATCC CAGATCCCTG    5820

GTCCTGCCGA CACGCAGCTA CTGAGAAGAC CAAAGAGGT GTGTGTGT CTATGTGTGT      5880

GTTTCAGCAC TTTGTAAATA GCAAGAAGCT GTACAGATTC TAGTTAATGT TGTGAATAAC    5940

ATCAATTAAT GTAACTAGTT AATTACTATG ATTATCACCT CCTGATAGTG AACATTTTGA    6000

GATTGGGCAT TCAGATGATG GGGTTTCACC CAACCTTGGG GCAGGTTTTT AAAAATTAGC    6060

TAGGCATCAA GGCCAGACCA GGGCTGGGGG TTGGGCTGTA GGCAGGGACA GTCACAGGAA    6120

TGCAGGATGC AGTCATCAGA CCTGAAAAAA CAACACTGGG GGAGGGGGAC GGTGAAGGCC    6180

AAGTTCCCAA TGAGGGTGAG ATTGGGCCTG GGGTCTCACC CCTAGTGTGG GGCCCCAGGT    6240

CCCGTGCCTC CCCTTCCCAA TGTGGCCTAT GGAGAGACAG GCCTTTCTCT CAGCCTCTGG    6300

AAGCCACCTG CTCTTTTGCT CTAGCACCTG GGTCCCAGCA TCTAGAGCAT GGAGCCTCTA    6360

GAAGCCATGC TCACCCGCCC ACATTTAATT AACAGCTGAG TCCCTGATGT CATCCTTACT    6420

CGAAGAGCTT AGAAACAAAG AGTGGGAAAT TCCACTGGGC CTACCTTCCT TGGGGATGTT    6480

CATGGGCCCC AGTTTCCAGT TTCCCTTGCC AGACAAGCCC ATCTTCAGCA GTTGCTAGTC    6540

CATTCTCCAT TCTGGAGAAT CTGCTCCAAA AAGCTGGCCA CATCTCTGAG GTGTCAGAAT    6600

TAAGCTGCCT CAGTAACTGC TCCCCCTTCT CCATATAAGC AAAGCCAGAA GCTCTAGCTT    6660

TACCCAGCTC TGCCTGGAGA CTAAGGCAAA TTGGGCCATT AAAAGCTCAG CTCCTATGTT    6720

GGTATTAACG GTGGTGGGTT TTGTTGCTTT CACACTCTAT CCACAGGATA GATTGAAACT    6780

GCCAGCTTCC ACCTGATCCC TGACCCTGGG ATGGCTGGAT TGAGCAATGA GCAGAGCCAA    6840

GCAGCACAGA GTCCCTGGG GCTAGAGGTG GAGGAGGCAG TCCTGGGAAT GGGAAAAACC     6900

CCAACTTTGG GGTCATAGAG GCACAGGTAA CCCATAAAAC TGCAAACAAG CTT           6953
```

( 2 ) INFORMATION FOR SEQ ID NO: 3:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( x i ) SEQUENCE DESCRIPTION: SEQ ID NO: 3:

```
ACGCAGCCAC TTCGAGTAC                                                   19
```

( 2 ) INFORMATION FOR SEQ ID NO: 4:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( x i ) SEQUENCE DESCRIPTION: SEQ ID NO: 4:

```
ACGCAGCCCC TTCGAGTAC                                                   19
```

( 2 ) INFORMATION FOR SEQ ID NO: 5:

( i ) SEQUENCE CHARACTERISTICS:
        ( A ) LENGTH: 15

( B ) TYPE: nucleic acid
( C ) STRANDEDNESS: single
( D ) TOPOLOGY: linear ( x i ) SEQUENCE DESCRIPTION: SEQ ID NO: 5:

| CGCAGCCACT TCGAG | 15 |
|---|---|

( 2 ) INFORMATION FOR SEQ ID NO: 6:

( i ) SEQUENCE CHARACTERISTICS:
( A ) LENGTH: 15
( B ) TYPE: nucleic acid
( C ) STRANDEDNESS: single
( D ) TOPOLOGY: linear ( x i ) SEQUENCE DESCRIPTION: SEQ ID NO: 6:

| CGCAGCCCCT TCGAG | 15 |
|---|---|

( 2 ) INFORMATION FOR SEQ ID NO: 7:

( i ) SEQUENCE CHARACTERISTICS:
( A ) LENGTH: 140
( B ) TYPE: nucleic acid
( C ) STRANDEDNESS: single
( D ) TOPOLOGY: linear ( x i ) SEQUENCE DESCRIPTION: SEQ ID NO: 7:

| AGCTCAGGCC | TTCGCAGCAT | TCTTGGGTGC | GAGCAGCCAG | GGGTCAGCCA | CAAGGGCCAC | 60 |
|---|---|---|---|---|---|---|
| AGCCATGAAT | CTACGTGCCC | TTCTCCAATG | CGACGGGTGT | GGTACGCAGC | CCCTTCGAGT | 120 |
| ACCCACAGTA | CTACCTGGCT | | | | | 140 |

( 2 ) INFORMATION FOR SEQ ID NO: 8:

( i ) SEQUENCE CHARACTERISTICS:
( A ) LENGTH: 973
( B ) TYPE: nucleic acid
( C ) STRANDEDNESS: single
( D ) TOPOLOGY: linear ( x i ) SEQUENCE DESCRIPTION: SEQ ID NO: 8:

| CGGGGCTGTG | CTGCACTTGA | CCGCAGCAGG | AGGGAGTCCA | GGAGCCAAGG | TTGCCGCGGT | 60 |
|---|---|---|---|---|---|---|
| GTCTCCGTCA | GCCTCACCAT | GAACCTGGAA | CCGCCCAAGG | CTGAGTTCCG | GTCAGCCACC | 120 |
| AGGGTGGCCG | GGGACCTGT | CACCCCAGG | AAAGGTCCCC | CTAAATTTAA | GCAGCGACAG | 180 |
| ACCAGGCAGT | TCAAGAGCAA | GCCCCCAAAG | AAAGGCGTTC | AAGGGTTTGG | GGACGACATC | 240 |
| CCTGGAATGG | AAGGCCTGGG | AACAGACATC | ACAGTCATCT | GCCCTTGGGA | GGCCTTCAAC | 300 |
| CACCTGGAGC | TGCACGAGCT | GGCCCAATAT | GGCATCATCT | AGCACGAGGC | CCTCGTGAAG | 360 |
| TCCAGACCCT | CCCCCTCCTG | CCCACTGTGC | TCTAAACCCT | GCTCAGGATT | CCTGTTGAGG | 420 |
| AGATGCCTCC | CTAGCCCAGA | TGGCACCTGG | ACACCAGGAT | GGGACTGCAA | CCTCAGGTCT | 480 |
| CCCCCTACAT | ATTAATACCA | GTCACCAGGA | GCCCACCACC | TCCCTCTAGG | ATGCCCCCTC | 540 |
| AGGGCCTGGC | CAGGCCCTGC | TCAACATCTG | GAGATACAGG | CCCACCCCTC | AGTCCTGCCC | 600 |
| ACAGAGAGGC | TTGGTCGGTC | TCCACTCCCA | GGGAGAACGG | GAAGTGGACC | CCAGCCCGGG | 660 |
| AGCCTGCTGG | ACCCCAGATC | GTCCCCTCCT | CCCAGCTGGA | AAGCTAGGGC | AGGTCTCCCC | 720 |
| AGAGTGCTTC | TGCACCCCAG | CCCCCTGTCC | TGCCTGTAAG | GGGATACAGA | GAAGCTCCCC | 780 |
| GTCTCTGCAT | CCCTTCCCAG | GGGGGTGCCC | TTAGTTTGGA | CATGCTGGGT | AGCAGGACTC | 840 |
| CAGGGCGTGC | ACGGTGAGCA | GATGAGGCCC | GAAGCTCATC | ACACCAGGGG | GCCATCCTTC | 900 |
| TCAATACAGC | CTGCCCTTGC | AGTCCCTATT | TCAAAATAAA | ATTAGTGTGT | CCTTGCCAAA | 960 |

AAAAAAAAAA AAA                                                                                                        973

( 2 ) INFORMATION FOR SEQ ID NO: 9:

( i ) SEQUENCE CHARACTERISTICS:
        ( A ) LENGTH: 264
        ( B ) TYPE: nucleic acid
        ( C ) STRANDEDNESS: single
        ( D ) TOPOLOGY: linear ( x i ) SEQUENCE DESCRIPTION: SEQ ID NO: 9:

```
ATG  AAC  CTG  GAA  CCG  CCC  AAG  GCT  GAG  TTC  CGG  TCA  GCC  ACC  AGG  GTG      48
Met  Asn  Leu  Glu  Pro  Pro  Lys  Ala  Glu  Phe  Arg  Ser  Ala  Thr  Arg  Val
 1                   5                        10                       15

GCC  GGG  GGA  CCT  GTC  ACC  CCC  AGG  AAA  GGT  CCC  CCT  AAA  TTT  AAG  CAG      96
Ala  Gly  Gly  Pro  Val  Thr  Pro  Arg  Lys  Gly  Pro  Pro  Lys  Phe  Lys  Gln
                20                       25                       30

CGA  CAG  ACC  AGG  CAG  TTC  AAG  AGC  AAG  CCC  CCA  AAG  AAA  GGC  GTT  CAA     144
Arg  Gln  Thr  Arg  Gln  Phe  Lys  Ser  Lys  Pro  Pro  Lys  Lys  Gly  Val  Gln
                35                       40                       45

GGG  TTT  GGG  GAC  GAC  ATC  CCT  GGA  ATG  GAA  GGC  CTG  GGA  ACA  GAC  ATC     192
Gly  Phe  Gly  Asp  Asp  Ile  Pro  Gly  Met  Glu  Gly  Leu  Gly  Thr  Asp  Ile
         50                       55                       60

ACA  GTC  ATC  TGC  CCT  TGG  GAG  GCC  TTC  AAC  CAC  CTG  GAG  CTG  CAC  GAG     240
Thr  Val  Ile  Cys  Pro  Trp  Glu  Ala  Phe  Asn  His  Leu  Glu  Leu  His  Glu
 65                       70                       75                       80

CTG  GCC  CAA  TAT  GGC  ATC  ATC  TAG                                              264
Leu  Ala  Gln  Tyr  Gly  Ile  Ile
                85
```

( 2 ) INFORMATION FOR SEQ ID NO: 10:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 10:

AGCTCAGGCC TTCGCAGCAT                                                                                                  20

( 2 ) INFORMATION FOR SEQ ID NO: 11:

( i ) SEQUENCE CHARACTERISTICS:
        ( A ) LENGTH: 20
        ( B ) TYPE: nucleic acid
        ( C ) STRANDEDNESS: sinle
        ( D ) TOPOLOGY: linear ( x i ) SEQUENCE DESCRIPTION: SEQ ID NO: 11:

GGAAGCTCAT GGGTGTCATG                                                                                                  20

( 2 ) INFORMATION FOR SEQ ID NO: 12:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 12:

TGAAGCTCAT GGGTGTCATG                                                                                                  20

( 2 ) INFORMATION FOR SEQ ID NO: 13:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( x i ) SEQUENCE DESCRIPTION: SEQ ID NO: 13:

ACCGCCCCAC CCTCACCTCT 20

( 2 ) INFORMATION FOR SEQ ID NO: 14:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( x i ) SEQUENCE DESCRIPTION: SEQ ID NO: 14:

CCCTATCCCT CCCTCTCCTG 20

( 2 ) INFORMATION FOR SEQ ID NO: 15:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( x i ) SEQUENCE DESCRIPTION: SEQ ID NO: 15:

CCTCCCTCAG CCCACAATCC 20

( 2 ) INFORMATION FOR SEQ ID NO: 16:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( x i ) SEQUENCE DESCRIPTION: SEQ ID NO: 16:

TGACTATGCG CCTGCGGTGT 20

( 2 ) INFORMATION FOR SEQ ID NO: 17:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( x i ) SEQUENCE DESCRIPTION: SEQ ID NO: 17:

GCGCTCTGGC GGGACTTACA 20

( 2 ) INFORMATION FOR SEQ ID NO: 18:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( x i ) SEQUENCE DESCRIPTION: SEQ ID NO: 18:

GCCTGCACAA CCCTGGTGAT 20

( 2 ) INFORMATION FOR SEQ ID NO: 19:

( i ) SEQUENCE CHARACTERISTICS:
    ( A ) LENGTH: 20

( B ) TYPE: nucleic acid
( C ) STRANDEDNESS: single
( D ) TOPOLOGY: linear ( x i ) SEQUENCE DESCRIPTION: SEQ ID NO: 19:

CCCTGCTGCT GTGGTCAGAC    20

( 2 ) INFORMATION FOR SEQ ID NO: 20:

( i ) SEQUENCE CHARACTERISTICS:
( A ) LENGTH: 20
( B ) TYPE: nucleic acid
( C ) STRANDEDNESS: single
( D ) TOPOLOGY: linear ( x i ) SEQUENCE DESCRIPTION: SEQ ID NO: 20:

CCTCTAAACT TCCTGTGGGA    20

( 2 ) INFORMATION FOR SEQ ID NO: 21:

( i ) SEQUENCE CHARACTERISTICS:
( A ) LENGTH: 20
( B ) TYPE: nucleic acid
( C ) STRANDEDNESS: single
( D ) TOPOLOGY: linear ( x i ) SEQUENCE DESCRIPTION: SEQ ID NO: 21:

AAGCCCATCT CCAGCTGTCT    20

( 2 ) INFORMATION FOR SEQ ID NO: 22:

( i ) SEQUENCE CHARACTERISTICS:
( A ) LENGTH: 30
( B ) TYPE: nucleic acid
( C ) STRANDEDNESS: single
( D ) TOPOLOGY: linear ( x i ) SEQUENCE DESCRIPTION: SEQ ID NO: 22:

TCGTAACTGT TCGTAACTGT AGTGTGCTGA    30

( 2 ) INFORMATION FOR SEQ ID NO: 23:

( i ) SEQUENCE CHARACTERISTICS:
( A ) LENGTH: 20
( B ) TYPE: nucleic acid
( C ) STRANDEDNESS: single
( D ) TOPOLOGY: linear ( x i ) SEQUENCE DESCRIPTION: SEQ ID NO: 23:

TATGCCAGAT GGAAGCCCTG    20

( 2 ) INFORMATION FOR SEQ ID NO: 24:

( i ) SEQUENCE CHARACTERISTICS:
( A ) LENGTH: 20
( B ) TYPE: nucleic acid
( C ) STRANDEDNESS: single
( D ) TOPOLOGY: linear ( x i ) SEQUENCE DESCRIPTION: SEQ ID NO: 24:

TCTGACCCCA GGACTGGAAG    20

( 2 ) INFORMATION FOR SEQ ID NO: 25:

( i ) SEQUENCE CHARACTERISTICS:
( A ) LENGTH: 20
( B ) TYPE: nucleic acid
( C ) STRANDEDNESS: single (D) TOPOLOGY: linear (xi) SEQUENCE DESCRIPTION: SEQ ID NO: 25:

AGTACTACCG GGACACAGAC 20

DIAGNOSIS OF HEREDITARY RETINAL DEGENERATIVE DISEASES

This application was partially funded by a grant from the National Eye Institute. The U.S. government has certain rights to the invention.

This application is a Continuation-In-Part of U.S. Ser. No. 805,123, Dec. 11, 1991, now U.S. Pat. No. 5,262,529, issued Nov. 16, 1993 which is in turn a Continuation-In-Part of U.S. Ser. No. 469,215, Jan. 24, 1990, now U.S. Pat. No. 5,335,546 issued Jul. 6, 1993.

BACKGROUND OF THE INVENTION

The field of the invention is detection of genetic abnormalities in humans.

The hereditary retinal degenerative diseases ("HRD diseases") are a group of inherited conditions in which progressive, bilateral degeneration of retinal structures leads to loss of retinal function; these diseases include, for example, age-related macular degeneration, a leading cause of visual impairment in the elderly; Leber's congenital amaurosis, which causes its victims to be born blind; and retinitis pigmentosa ("RP"). RP is the name given to those inherited retinopathies which are characterized by loss of retinal photoreceptors (rods and cones), with retinal electrical responses to light flashes (i.e. electroretinograms, or "ERGs") that are reduced in amplitude. Familial cases of RP usually present in childhood with night blindness and loss of midperipheral visual field due to the loss of rods and cones in the peripheral retina. As the condition progresses, contraction of the visual fields eventually leads to blindness. Signs on fundus examination in advanced stages include retinal vessel attenuation, intraretinal pigment in the peripheral fundus, "bone spicule" pigmentation of the retina, and waxy pallor of the optic disc. Patients have abnormal light-evoked electrical responses from the retina (i.e., ERGs), even in the early stages in the absence of visible abnormalities on fundus examination. Histopathologic studies have revealed widespread loss of photoreceptors in advanced stages.

The incidence of RP in the United States is estimated to be about 1:3500 births. Approximately 43% of cases in the state of Maine are from families with an autosomal dominant mode of transmission, 20% autosomal recessive, and 8% X-linked; 23% are isolated cases and 6% are undetermined (e.g., adopted) (Bunker et al., Am. J. Ophthalmol. 97:357–365, 1984). Genetic heterogeneity is thought to exist within each hereditary pattern. For example, linkage studies have revealed at least two distinct genetic loci for RP on the X-chromosome (Chen, Am. J. Hum. Genet. 45:401–411, 1989), another possibly near the rhesus locus on chromosome 1p (Yijian et al., Cytogenet. Cell Genet. 46:614, 1987), and a fourth on the long arm of chromosome 3 (McWilliam et al., Genomics 5:619–622, 1989). Hence, RP is not one disease, but a group of diseases caused by mutations at various loci within the human genome.

SUMMARY OF THE INVENTION

In general, the invention features a method of diagnosing in a mammal, e.g., a human subject, an increased likelihood of, inclination toward, or susceptibility to developing a disease, e.g., retinitis pigmentosa, in which a mutant form of a human photoreceptor protein is a causative agent. The same method is also used to diagnose the ability of a mammal, e.g., a human, to transmit to future generations a mutant form of a human photoreceptor protein which is a causative agent of a disease, e.g., retinitis pigmentosa. The method involves analyzing the DNA of the mammal to determine the presence or absence of a mutation in a gene for a photoreceptor protein, the presence of such a mutation indicating the increased likelihood. Preferably the DNA is analyzed by amplifying the DNA with, e.g., the polymerase chain reaction, and identifying mutations in the DNA by use of the single-strand conformation polymorphism (SSCP) technique, as used and described herein, or by direct DNA sequencing. The term "photoreceptor protein" means any protein which is expressed solely or predominantly by retinal cells, including cells of the retinal pigment epithelium; preferably it is one of the following: a cone visual pigment, a subunit of rod-transducin, a subunit of cone transducin, rhodopsin, interphotoreceptor retinal binding protein, retinal degeneration slow protein (RDS; also known as peripherin) or, more preferably, a subunit of retinal cGMP phosphodiesterase, e.g., the α- or γ-subunits of the retinal cGMP phosphodiesterase, or the γ-subunit of retinal cGMP phosphodiesterase (hereafter referred to as PDE β; also known in the art as the β-subunit of rod phosphodiesterase). A photoreceptor protein can be an enzyme, e.g., a member of the phototransduction enzyme cascade, or a structural protein of the photoreceptor outer segment. Examples are shown in FIG. 20.

The invention also features a probe or primer (that is, an oligonucleotide suitable for serving as a hybridization probe and/or as a primer for DNA or RNA synthesis along a complementary template, the oligonucleotide being of 10–50, preferably 13–35, or 15–25 bases in length) which includes a substantially purified single-stranded oligonucleotide (an RNA or DNA molecule at least two nucleotides in length) containing a region the sequence of which is identical to the sequence of a six-nucleotide, single-stranded segment of a gene encoding a mutant form of a human photoreceptor protein, which segment includes part or all of the mutation, or part or all of a mutation characterizing the mutant form of the protein.

Where the photoreceptor protein is the protein encoded by the RDS gene, the mutation preferably includes a change in codon 219, 216, or 185, preferably such that, respectively, there is a change, e.g., a deletion, at codon 219, a change, e.g., a C-to-T transition, in the second base of codon 216, or a change, e.g., a T-to-C transition, in the second base of codon 185.

Where the photoreceptor protein is encoded by the gene for PDE β, the mutation preferably includes a change in codon 298, 496, 531, or 557, preferably such that, respectively, there is a change, i.e., a C-to-T transition, resulting in a nonsense mutation (the first base of codon 298); a change, i.e., a C-to-T transition, resulting in a nonsense mutation (the first base of codon 531); a change, i.e., a deletion, in a nucleotide of codon 496, and a change, i.e., a C-to-T transition, resulting in a missense mutation (the first base of codon 557) resulting in a tyrosine.

The probe or primer of the invention may be used in one of the various methods of the invention, each of which is useful for detecting a mutation in a gene encoding a human photoreceptor protein, or for diagnosing an HRD disease (preferably RP) in a human fetus or patient, or for detecting, in a human fetus or patient, a genetic predisposition to develop such a disease. One of the methods includes the following steps:

(a) providing the probe or primer of the invention, (b) exposing the probe or primer to a nucleic acid sample obtained or derived from the individual to be tested, and (c) detecting hybridization of the probe or primer to the nucleic acid sample. The nucleic acid sample may be RNA, cDNA, genomic DNA, or DNA amplified by cloning or polymerase chain reaction ("PCR").

Another such method involves the following steps:

(a) providing the probe or primer of the invention;

(b) combining this probe or primer with a second primer and a nucleic acid sample (generally but not necessarily genomic DNA) derived from the individual to be tested, under conditions permitting a detectable difference in the extent of amplification (i.e., the making of multiple DNA copies) of a nucleic acid template which includes the mutant sequence, compared to the extent of amplification of the corresponding section of a normal allele; and (c) detecting (e.g., by ethidium bromide staining of a gel) the extent of amplification which took place. The second primer is an oligonucleotide that includes a sequence identical to that of a six- nucleotide segment of the template DNA, which segment is located (i) on the DNA strand complementary to the strand on which the probe or primer segment of the gene is located, and (ii) on the opposite side of the mutation from the probe or primer segment of the gene, such that the probe or primer and the second primer together are suitable for priming the amplification, by multiple cycles of PCR, of a section of template DNA that encompasses the mutation.

The invention also provides for a method of preparing such a probe or primer, which method includes the steps of (a) providing a sample of nucleic acid (i.e., genomic DNA, cDNA, or mRNA) obtained or derived from a patient with an HRD disease;

(b) amplifying a portion of the nucleic acid, which portion includes a fragment of a gene encoding a mutant form of a human photoreceptor protein, which fragment includes part or all of the mutation (i.e., part or all of the segment of the mutant gene sequence which differs from the sequence of the normal allele is included in the sequence of the fragment);

(c) sequencing (i.e., determining the DNA sequence of) the amplified nucleic acid; and (d) preparing a single-stranded oligonucleotide (preferably DNA) containing a region the sequence of which is identical to the sequence of a six-nucleotide segment of the amplified nucleic acid, which segment includes part or all of the mutation.

In another aspect, the invention features a transgenic non-human mammal (preferably a mouse), some or all of whose nucleated cells contain a gene encoding a mutant form of a human photoreceptor protein, preferably a mutant form of either the RDS gene, or of the gene encoding PDE β, which gene was introduced into the mammal, or an ancestor of that mammal, at an embryonic or germ cell stage. This "embryonic stage" may be any point from the moment of conception (e.g., as where the sperm or egg bears the foreign gene) throughout all of the stages of embryonic development of the fetus. A "transgenic mammal" herein denotes a mammal bearing in some or all of its nucleated cells one or more genes derived from a different species; if the cells bearing the foreign gene include cells of the animal's germline, the gene may be transmissable to the animal's offspring. The photoreceptor protein is preferably selected from the group consisting of rhodopsin, a cone visual pigment, a subunit of rod-transducin, a subunit of cone-transducin, a subunit of retinal cGMP phosphodiesterase, e.g., PDE β, the protein encoded by RDS, and interphotoreceptor retinal binding protein. Where the photoreceptor protein is the protein encoded by RDS, this gene has, most preferably, a mutation in codon 219, 216, or 185, preferably such that, respectively, there is a change, e.g., a deletion, at codon 219, a change, e.g., a C-to-T transition, in the second base of codon 216, or a change, e.g., a T-to-C transition, in the second base of codon 185. Where the photoreceptor protein is PDE β, the gene encoding it has, most preferably, a mutation in the codon 298, 496, 531, or 557, preferably such that, respectively, there is a change, e.g., a C-to-T transition, resulting in a nonsense mutation (the first base of codon 298); a change, i.e., a C-to-T transition, resulting in a nonsense mutation (the first base of codon 531); a change, i.e., a deletion, in a nucleotide of codon 496, and a change, i.e., a C-to-T transition, resulting in a missense mutation (the first base of codon 557) resulting in a tyrosine.

The probe or primers of the invention provide a simple and highly accurate means of diagnosing certain HRD diseases, including those involving defects in the genes encoding rhodopsin, PDE β, and other photoreceptor proteins. The diagnostic assay can be carried out on DNA from virtually any nucleated cell of the patient, including an easily obtained cell such as a leukocyte. Once a particular genetic defect has been identified in a patient with a given HRD disease, family members of that patient may be conveniently tested for the presence of that genetic defect and thus for their expected susceptibility to the same disease, or their status as carriers of the defect. In particular, by applying the assay of the invention to cells obtained by amniocentesis, a fetus can be tested while still in utero. Treatment to forestall the progress of the disease could thus be begun prior to the onset of any physical symptoms.

The invention also provides a means of creating animal models for HRD diseases, which, chiefly because the affected tissue is solely located within the eye, have proven very difficult to study in humans. The transgenic animals will provide a way to develop and test potential therapies for the various HRD diseases, and may eventually lead to cures for these devastating illnesses.

Other features and advantages of the invention will be apparent from the following description of the preferred embodiments thereof, and from the claims.

DESCRIPTION OF THE PREFERRED EMBODIMENTS

The drawings will first briefly be described. Drawings FIG. 1 is the nucleotide sequence of the gene encoding normal human rhodopsin (SEQ ID NO: 1), with the corresponding amino acid sequence shown below the nucleotide sequence and with the placement but not the full sequence of each of the five rhodopsin introns indicated; codon 23 is circled (adapted from FIG. 2 of Nathan and Hogness, Proc. Natl. Acad. Sci. USA 81:4851–4855, 1984).

FIG. 2a and 2b the nucleotide sequence of the entire gene encoding normal human rhodopsin, including the full sequence of each intron (SEQ ID NO: 2), with numbered boxes drawn around the sequences which correspond to PCR primers ultized to amplify the various exons (sequence obtained from Genbank Accession No. K02281, EMBL ID:HSOPS).

FIG. 3 is a DNA sequencing gel analysis of codons 20 to 26 of rhodopsin genes obtained from three patients with autosomal dominant RP.

FIG. 4 is an illustration of the nucleotide sequences of (a) a 19mer oligonucleotide probe with a C-to-A transversion mutation in codon 23 (underlined) (SEQ ID NO: 3), (b) the corresponding 19mer oligonucleotide probe with the normal proline-23 codon (SEQ ID NO: 4), (c) a 15mer oligonucleotide probe with the C-to-A transversion mutation in codon 23 (SEQ ID NO: 5), and (d) the corresponding 15mer oligonucleotide probe with the normal proline-23 codon (SEQ ID NO: 6).

Figure 7:
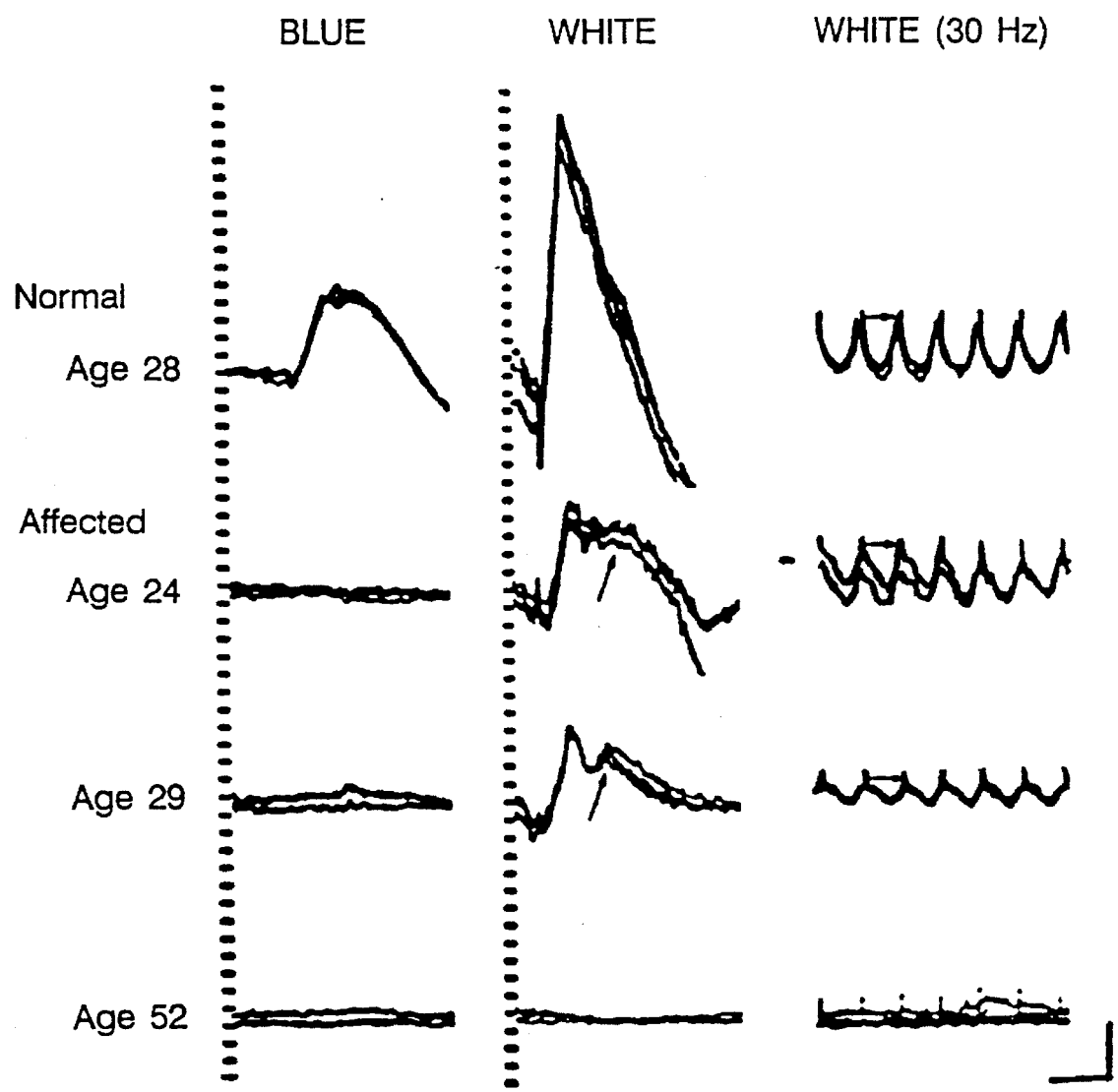

FIG. 7 is a comparison of full-field ERGs from an unaffected individual (age 28), her two affected siblings (ages 24 and 29), and an affected aunt (age 52) in family #5850 with autosomal dominant RP in a rhodopsin gene mutation.

FIG. 8 is the sequence of a portion of the human rhodopsin gene from nucleotide #211 to #390 (SEQ ID NO: 7), showing the sequences (boxed) of PCR primers #348 (SEQ ID NO: 10), #485 (SEQ ID NO: 11), and #502 (SEQ ID NO: 12), wherein #485 and #502 are identical except for their 3' nucleotides.

Figure 9:
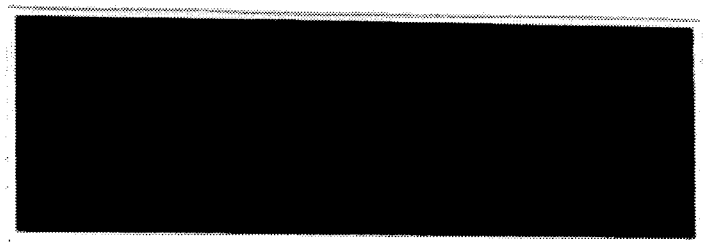

FIG. 9 is a photograph of an agarose gel in which the products of PCR amplification of the DNA of a patient with a C-to-A mutation in codon 23 of one rhodopsin allele (lanes 2 and 7) and that of an individual with two normal rhodopsin alleles (lanes 3 and 8) are compared to that of a mutation-bearing control (lanes 1 and 6).

FIG. 10 is the cDNA sequence of the γ-subunit of human retinal cGMP phosphodiesterase (SEQ ID NO: 8).

FIG. 11 is the DNA sequence of the longest open reading frame in the cDNA sequence of FIG. 9, with amino acid residues shown below corresponding codons (SEQ ID NO: 9).

Figure 12:
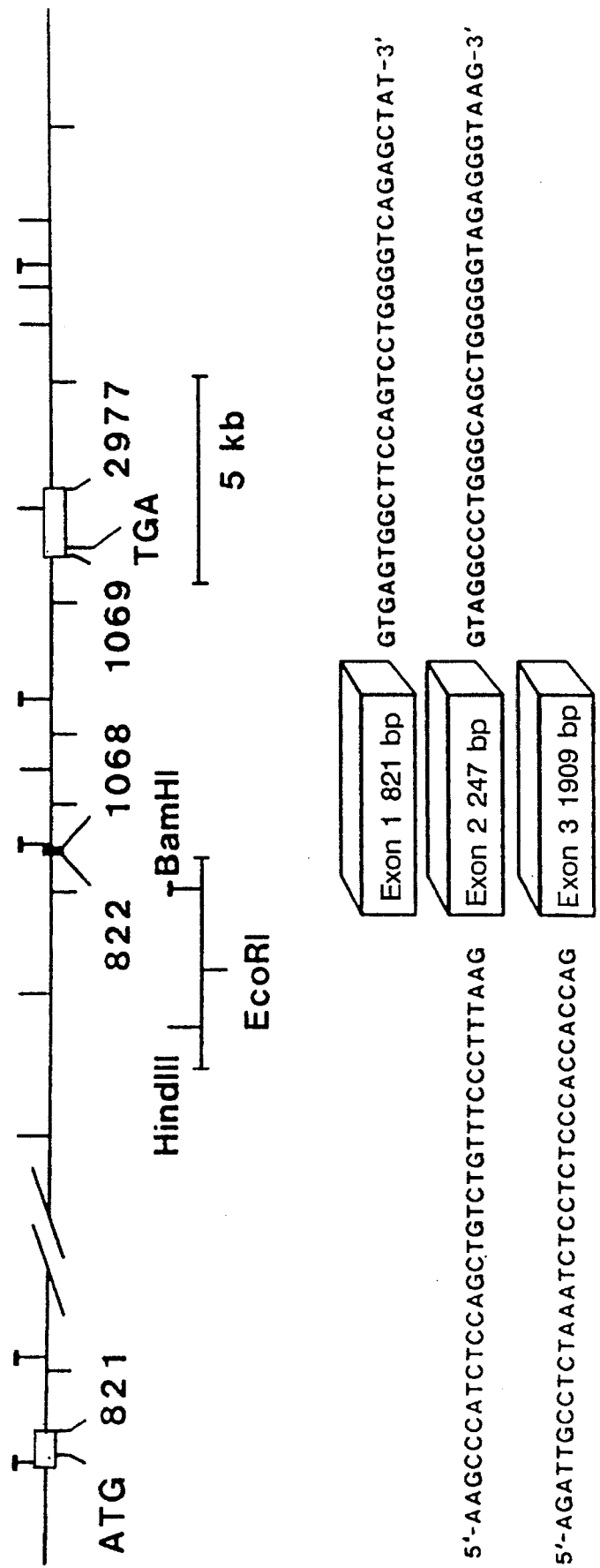

FIG. 12 is a map of the human RDS locus. In the top part of the figure, the numbers beneath each exon denote the nucleotides at the 5' or 3' ends. The lower part of the figure provides the flanking intron sequences from which primers were derived. The numbering scheme is that described in Travis et al. (1991, Genomics 10:773).

Figure 13A:
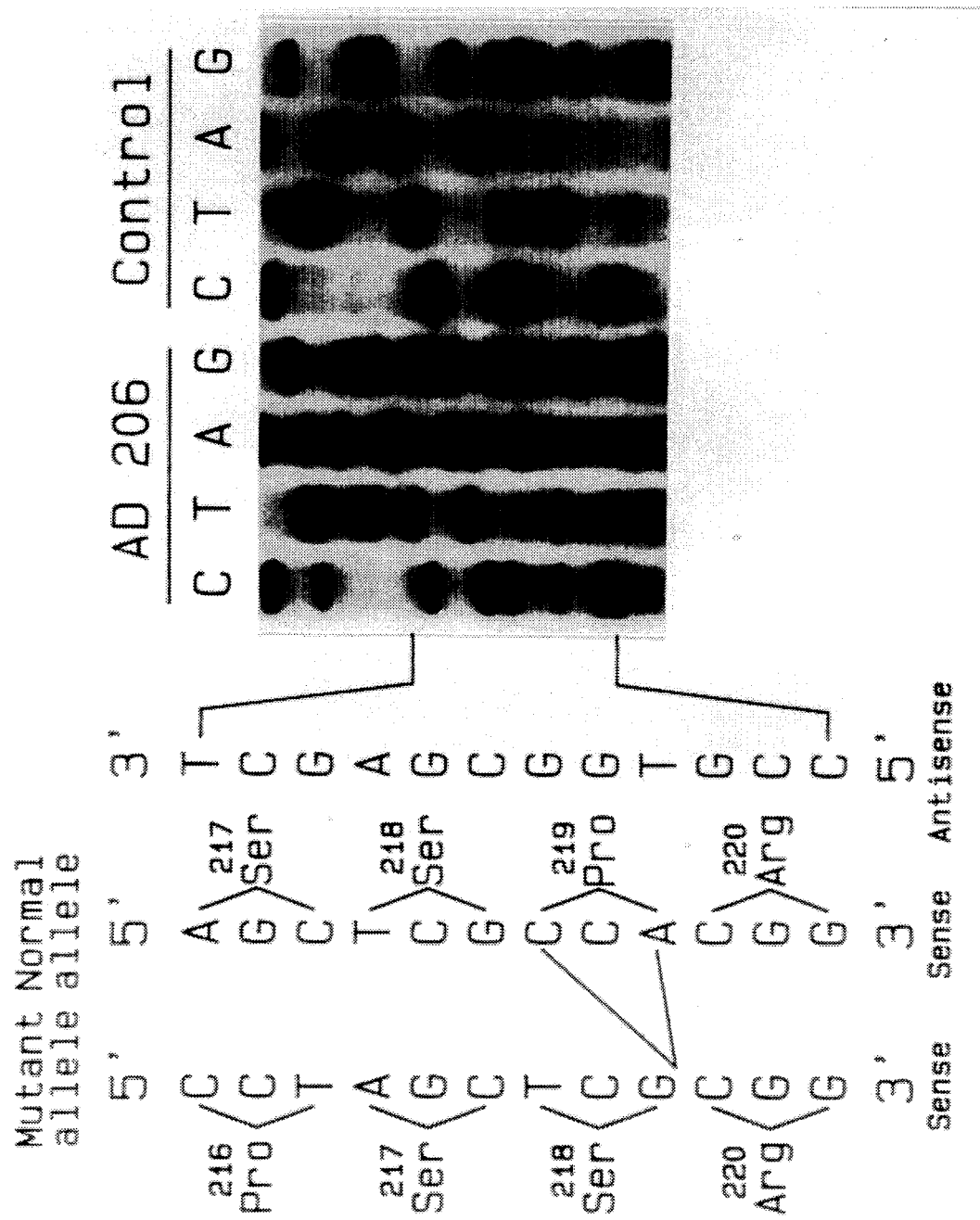
Figure 13B:
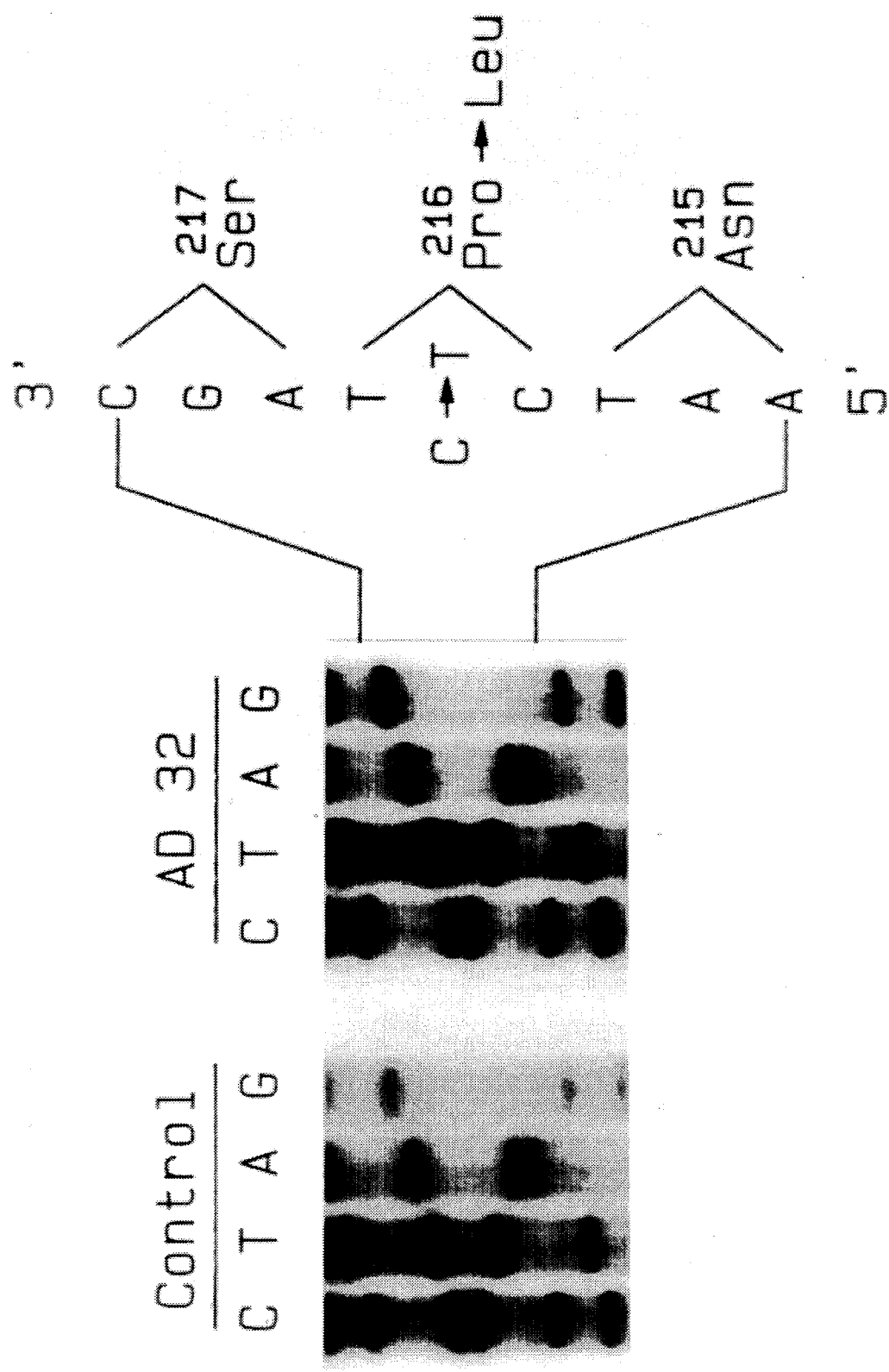
Figure 13C:
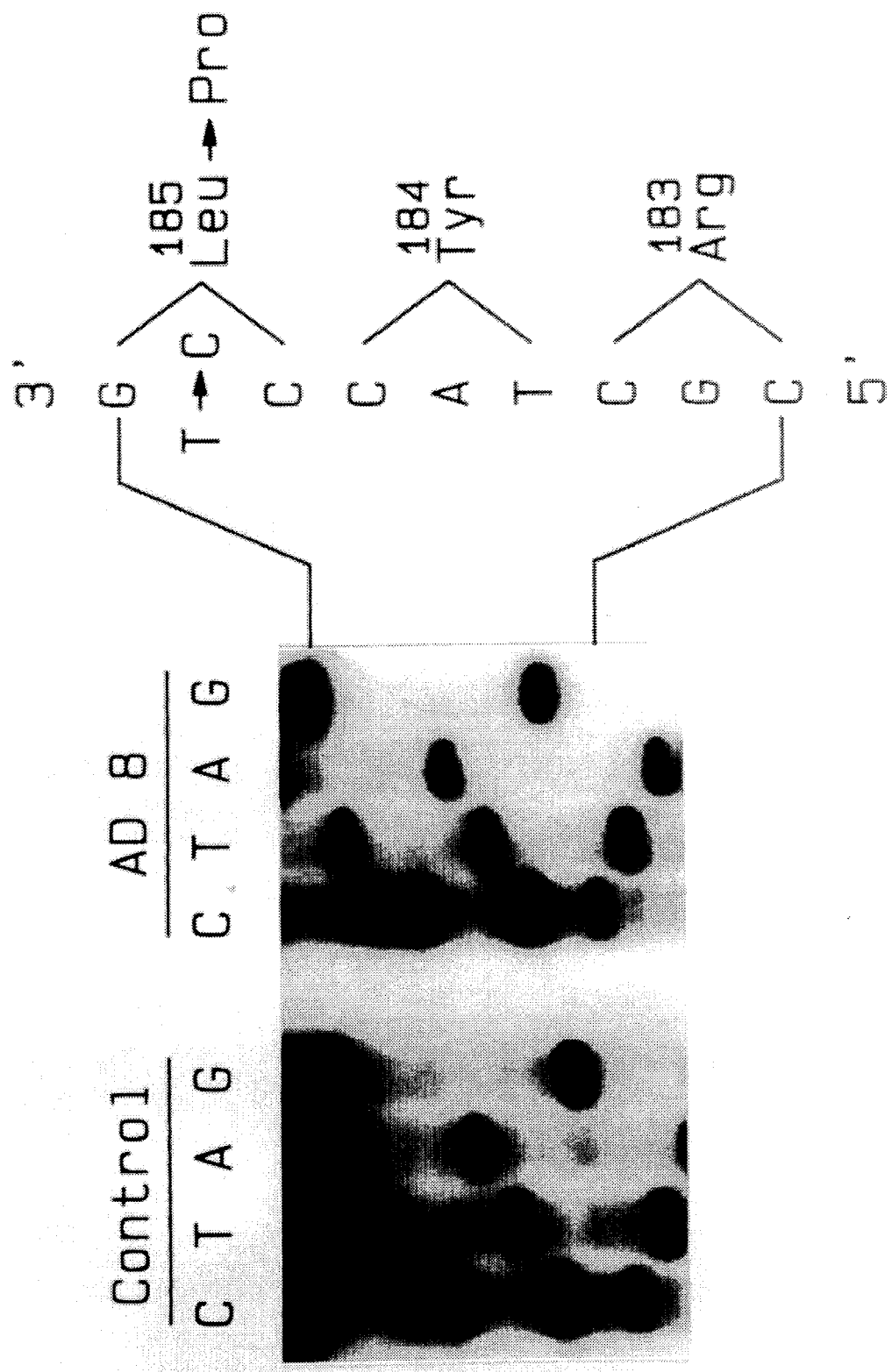

FIGS. 13A, 13B, and 13C show the nucleotide sequence of codons found to be altered in patients with autosomal dominant retinitis pigmentosa. FIG. 13a) Patient AD206 has a deletion of codon 219. FIG. 13b) Patient AD32 has a C-to-T transition in the second base of codon 216, changing the specificity of this codon from proline to leucine. FIG. 13c) Patient AD8 has a T-to-C transition in the second base of codon 185, changing the specificity of this codon from proline to leucine.

Figure 14A:
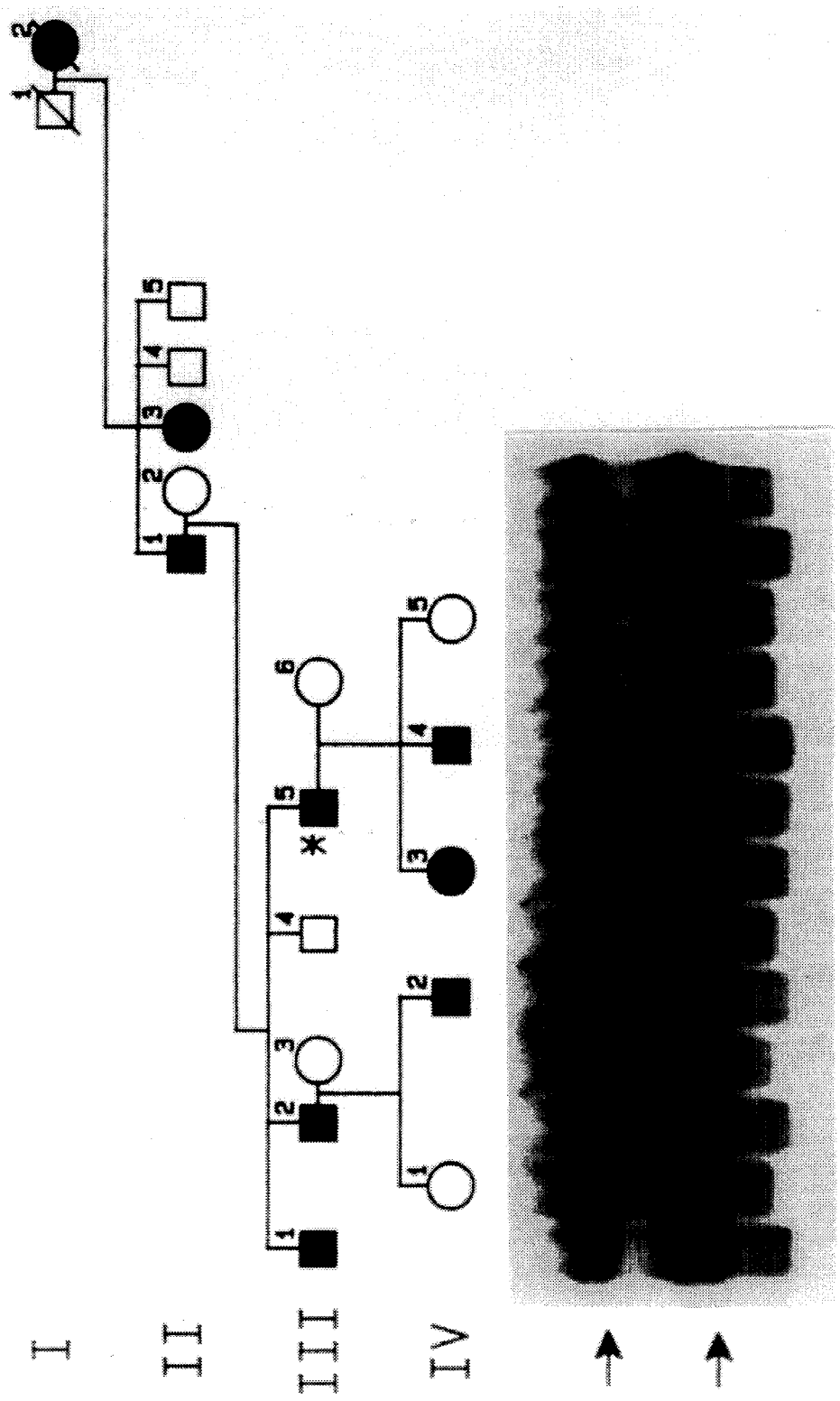
Figure 14B:
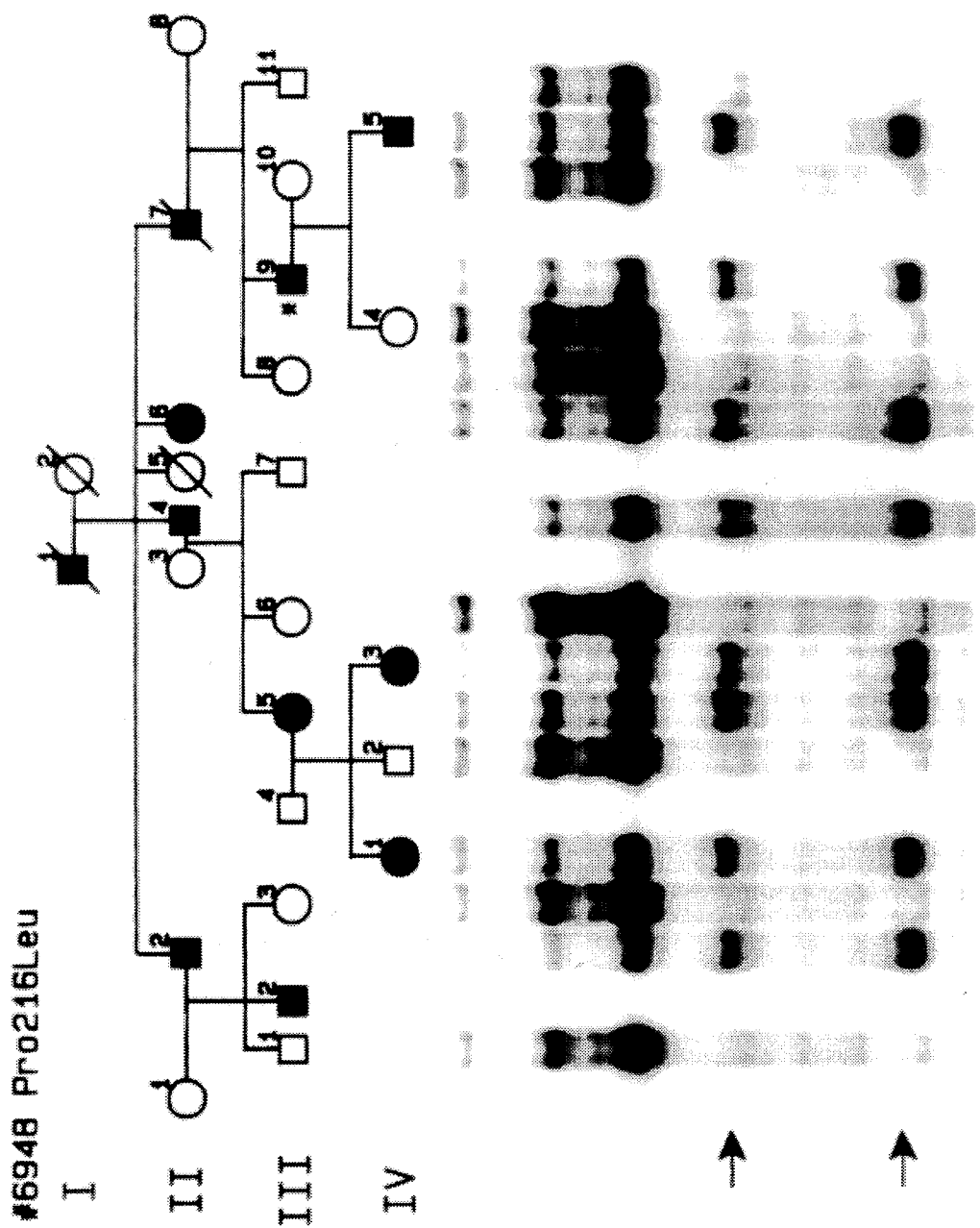
Figure 14C:

FIGS. 14A, 14B, and 14C show diagrams of cosegregation of retinitis pigmentosa with the mutant bands detected by SSCP. The patients AD206, AD32 and AD8 with the mutations shown in FIGS. 13A, 13B, and 13C are members of families #6459, #6948, and #6935 respectively, and are indicated with asterisks. Affected members are designated by filled symbols. Beneath each schematic pedigree are the results of SSCP analysis. Arrows designate mutant bands. No blood sample was obtained from the individuals with blank lanes beneath their symbols. Patients IV-3 and IV-4 in pedigree #6459 and patient III-6 in pedigree #6935 have not been examined clinically.

Figure 15:
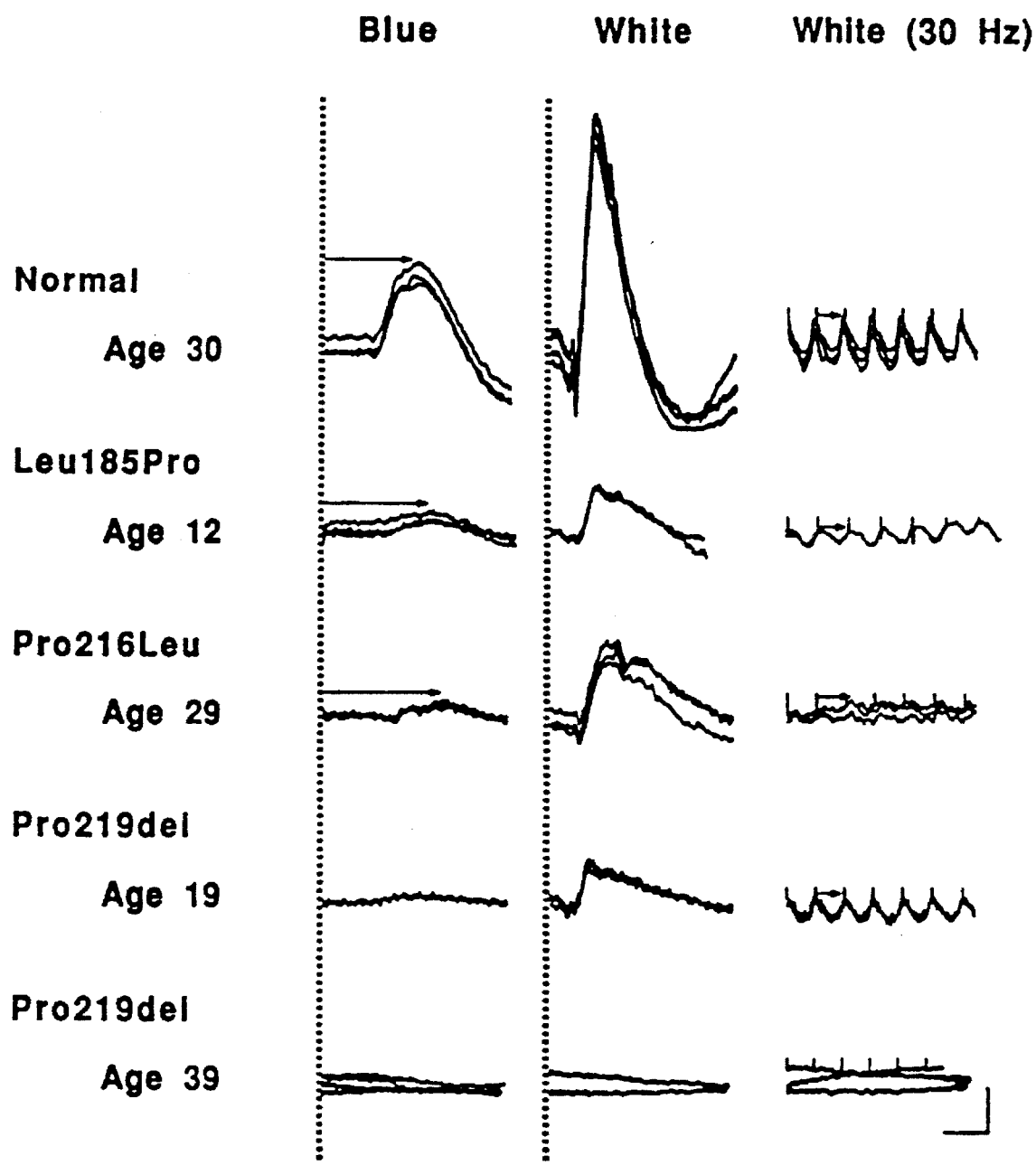

FIG. 15 is a diagram of full-field ERGs from an unaffected individual (age 30), patients with Leu185Pro (age 12), Pro216Leu (age 29), and Pro219del (age 19), each with an early stage of retinitis pigmentosa, and a patient with Pro219del (age 39) with an advanced stage of the disease. Illustrated are rod-isolated responses to flashes of dim blue light (left column), mixed cone-rod responses to flashes of white light (middle column), and cone-isolated responses to 30 Hz white flickering light (right column). Stimulus onset it denoted by vertical hatched lines in the left and middle columns and by short vertical lines in the right column. Horizontal arrows in the left and right columns designate respectively rod and cone response times (that is the time interval between a flash and the corresponding cornea-positive response peak). Under these test conditions, normal amplitudes are $\geq 100$ μV (left column), $\geq$μV (middle column), and $\geq$μV (right column); normal rod response time is $\leq 108$ ms and normal cone response time is $\leq 32$ ms. Calibration symbol (lower right) designates 50 ms horizontally and 100 μV vertically.

Figure 16:
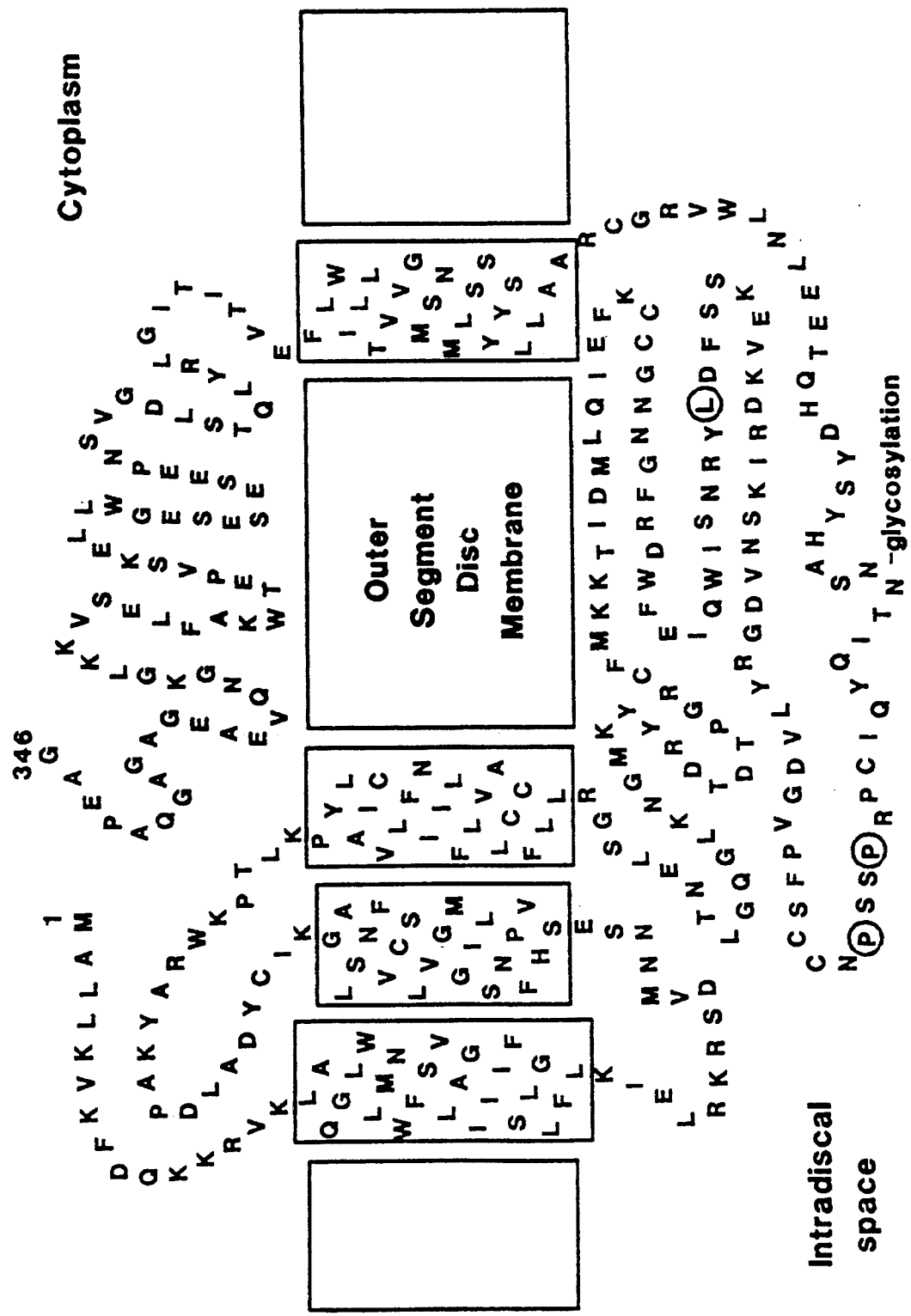

FIG. 16 is the amino acid sequence of the protein encoded by RDS and its predicted position in the photoreceptor outer segment. Mutant amino acids are circled.

Figure 17A:
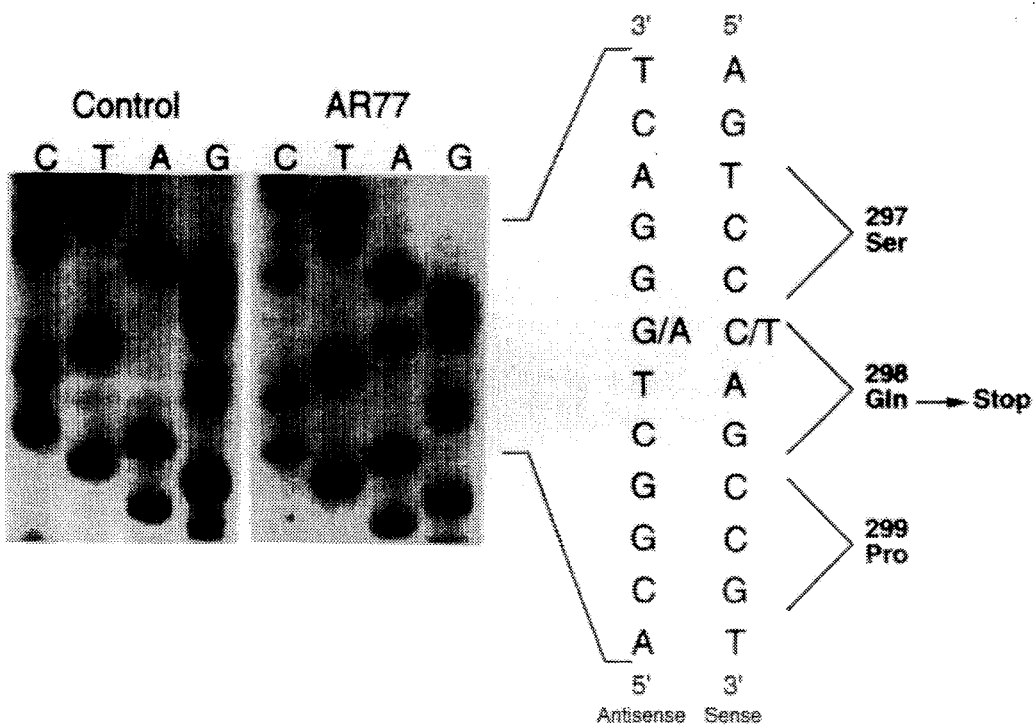
Figure 17B:
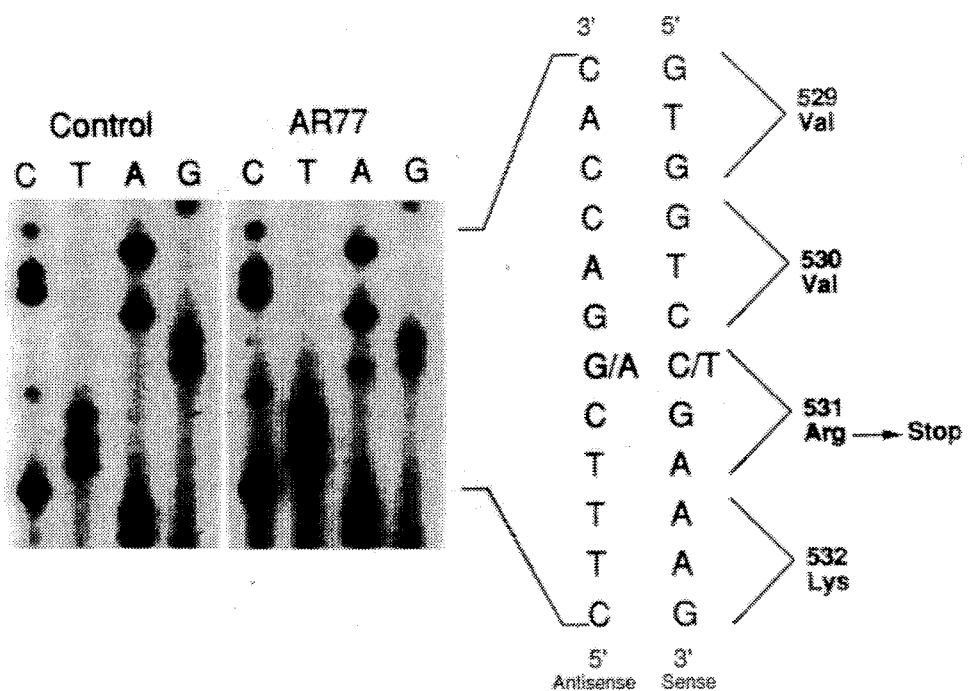

FIGS. 17A and 17B show the sequence of a portion of the human PDE β gene showing codons altered in patient AR77 with autosomal recessive retinitis pigmentosa. Patient AR77 is a heterozygous carrier of both: FIG. 17A: a C-to-T transition in the first base of codon 298 that results in a nonsense mutation, and FIG. 17B: a C-to-T transition in the first base of codon 531 that also results in a nonsense mutation. In both FIG. 17A and FIG. 17B, the 3' end of the sense sequence is at the bottom and the 5' end at the top.

Figure 18A:
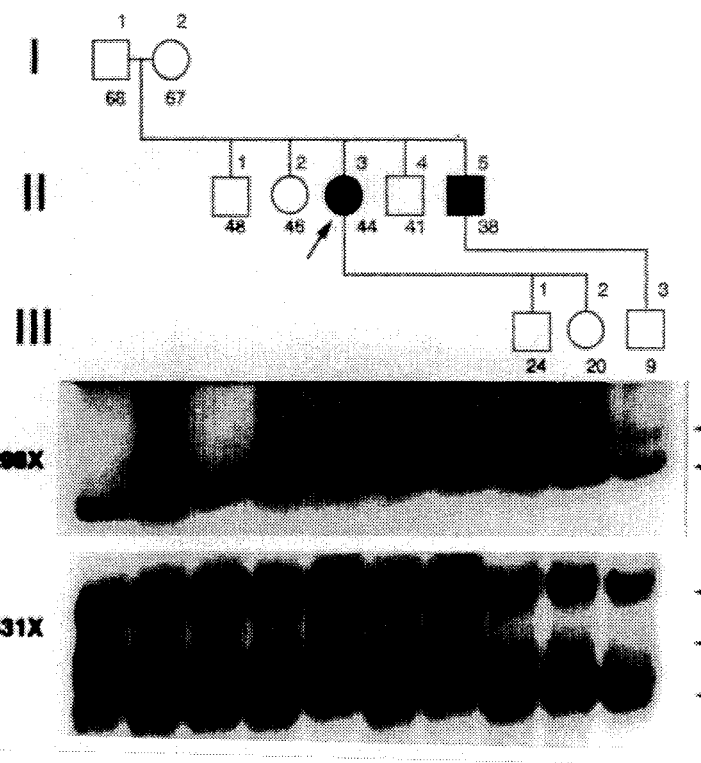
Figure 18B:
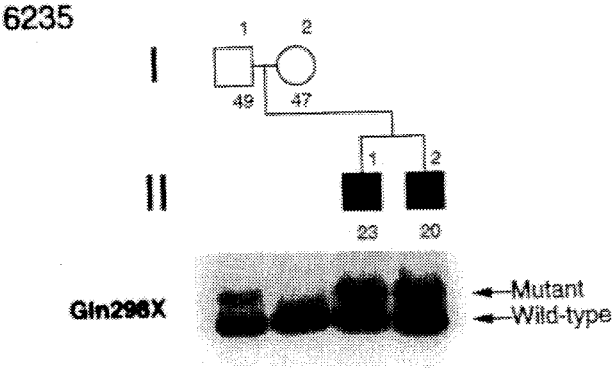
Figure 18C:
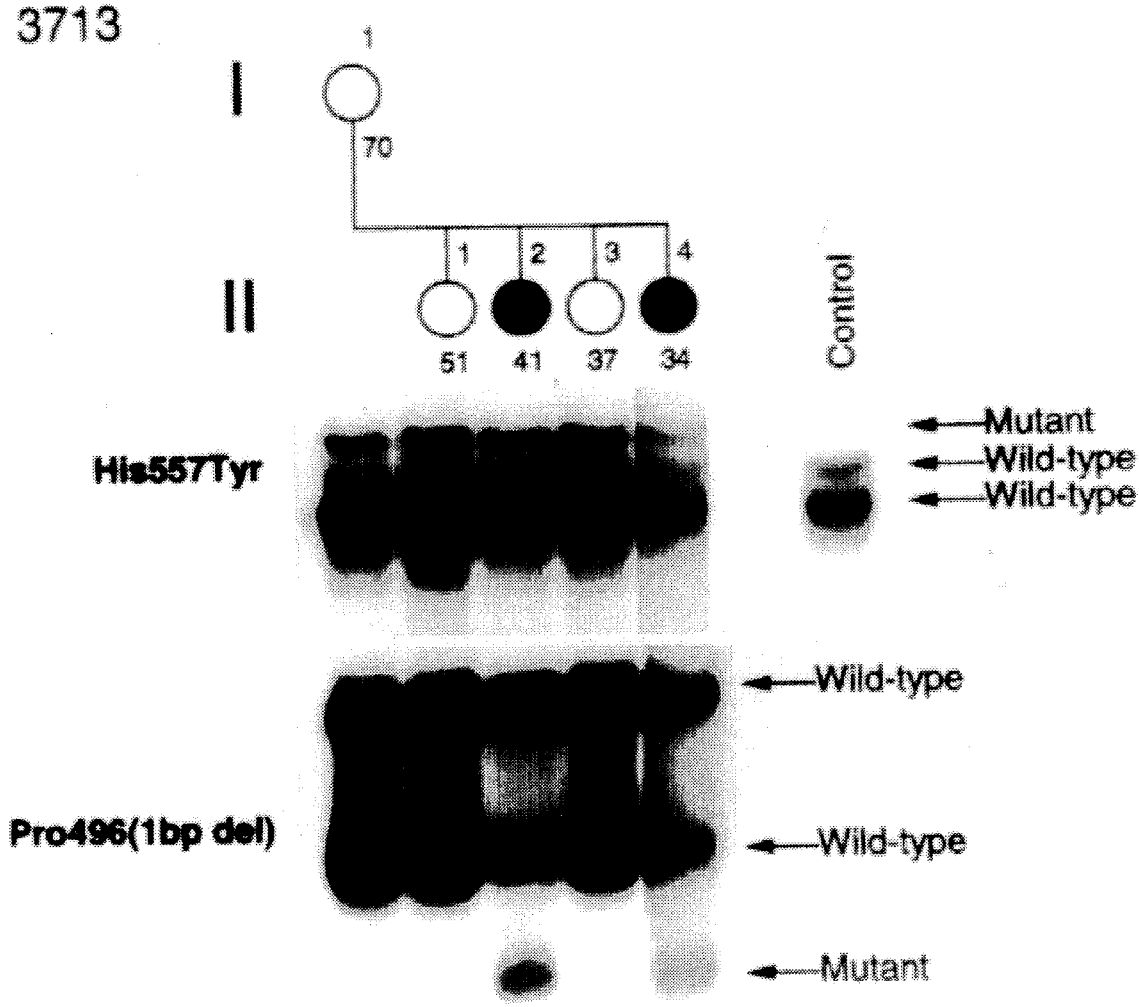

FIGS. 18A, 18B, and 18C are schematic representations showing cosegregation of autosomal recessive retinitis pigmentosa with PDE β. Variant electrophoretic bands detected by SSCP analysis are shown in the agarose gel (see photographic inserts). FIG. 18A: Patient AR77 with the mutations shown in FIG. 17 is member II-3 (designated by an arrow) of family 6193. SSCP analysis of families 6235 and 3713 are shown in FIG. 18B and FIG. 18C, respectively. Patient AR120 is member II-1 in family 6235, and patient AR67 is member II-2 in family 3713. Filled symbols indicate affected individuals. The results of SSCP analysis are beneath each symbol. Arrows on the left point to mutant and wild-type bands. A normal control with wild-type bands is included to the left of the pedigree of 3713. The number immediately below each symbol is the age of the individual in December, 1992.

Figure 19:
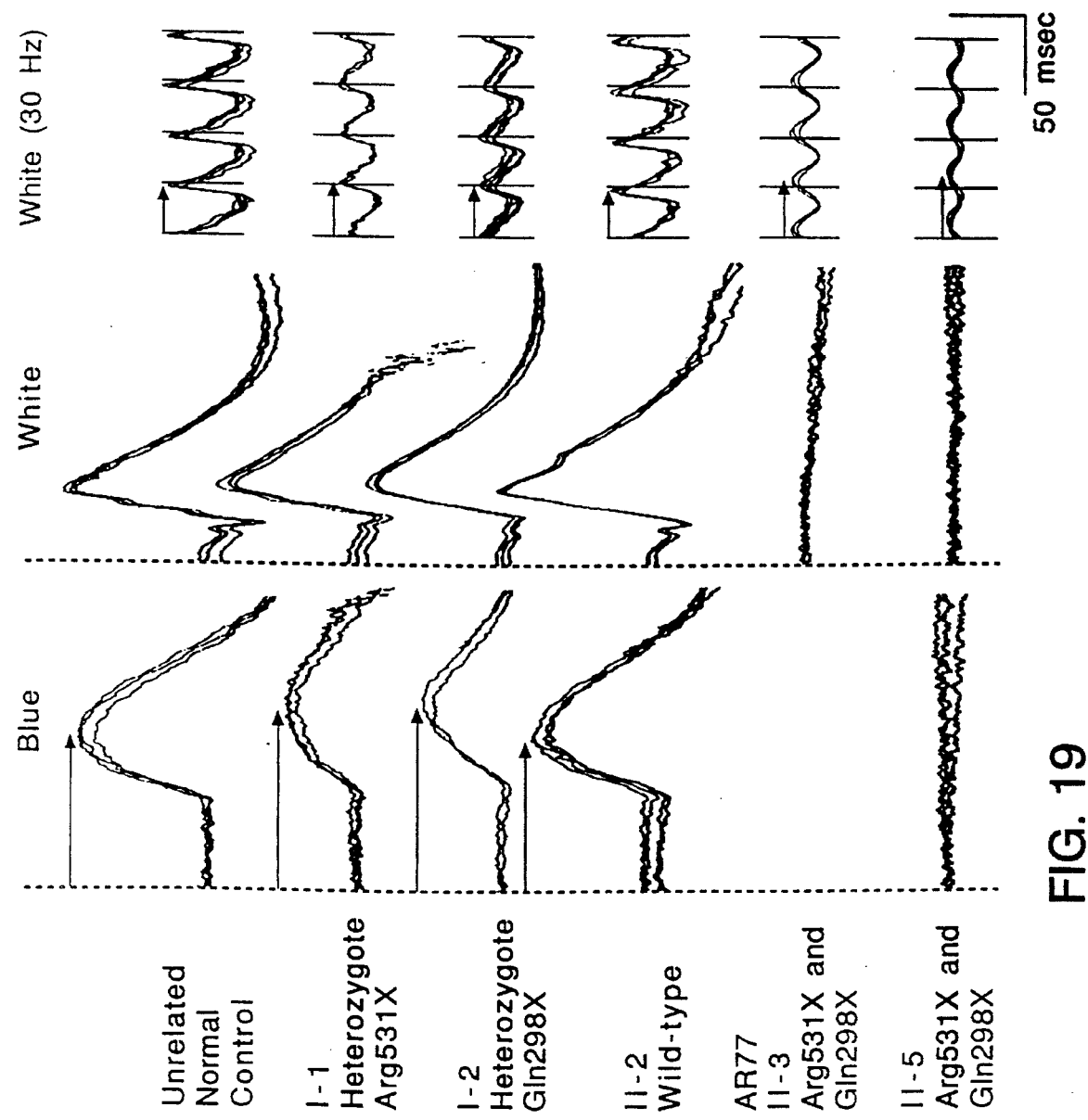

FIG. 19 is a comparison of full-field ERGs from an unrelated normal control and members of family 6193. I-1 is the father of AR77, who heterozygously carries Arg531X (age 68); I-2 is the mother of AR77, who heterozygously carries (II-3) is a heterozygous carrier of Arg531X and Gln298X (age 43 at time of exam); and II-5 is the affected brother of AR77, who also carries both mutations (age 38).

Figure 20:
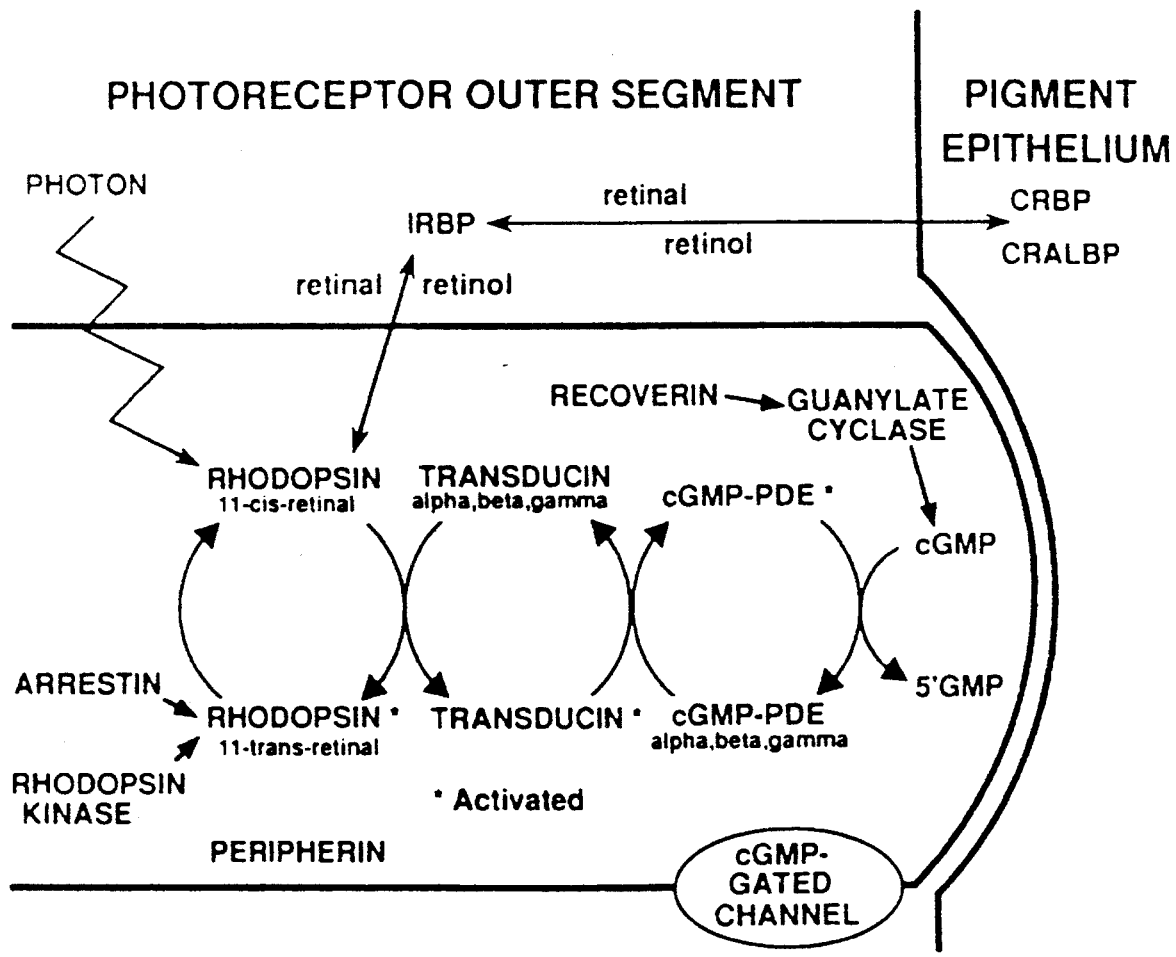

FIG. 20 is a schematic representation of the enzyme cascade of the photoreceptor outer segment. In the figure, S-antigen is identified by its co-name "arrestin", and RDS is identified by its co-name "peripherin".

Diagnosis of HRD Diseases

The invention disclosed herein relates to diagnosis of various HRD diseases by first identifying the genetic defect which causes the disease in question, and then devising an assay using either a hybridization probe or a PCR amplification primer containing the mutant sequence. It is postulated that many, if not all, of such diseases are attributable to mutations in the various photoreceptor proteins, including but not limited to rhodopsin, the cone visual pigments, rod-transducin, cone-transducin, the γ-subunit of retinal cGMP phosphodiesterase, PDE β, RDS, and interphotoreceptor retinal binding protein. As the test of this hypothesis, rhodopsin genes from several patients with autosomal dominant RP were examined by the method of the invention for the presence of any deviation from the normal DNA sequence for such gene. This examination of the rhodopsin genes of affected patients, described in detail in Example 1 below, showed that at least one type of RP involves a point mutation in one rhodopsin allele of affected patients.

In a second test of this hypothesis, three distinct mutations of the human homologue of the retinal degeneration slow gene (RDS) that cosegregate with autosomal dominant retinitis pigmentosa in separate families have been identified. The murine rds allele is a semidominant mutation with a phenotype of abnormal development of rod and cone photoreceptors, followed by their slow degeneration (Van Nie et al., 1978, Tissue Antigens 12:106; Sanyal et al., 1980, J. Comp. Neurol. 194:193; Cohen, 1983, Invest. Ophthalmol. Vis. Sci. 24:832). The phenotype has been regarded as a possible model for one of the scores of human HRDS, such as retinitis pigmentosa which is also characterized by photoreceptor degeneration. The results indicate that some cases of autosomal dominant retinitis pigmentosa have disease due to mutations at the RDS locus. A description of this work is provided in Examples 5–8.

In a third test of this hypothesis, four mutations have been identified in a partial screen (7 of 22 exons) of the PDE β gene. PDE β is one of the three subunits (alpha, beta, and gamma) of retinal cGMP phosphodiesterase, and as such is a component of the portion of the phototransduction cascade responsible for the conversion of cGMP to 5'GMP. The PDE β gene is the third human locus at which mutations have been found in patients with autosomal recessive retinitis pigmentosa. A description of the work on PDE β mutations is provided in Examples 9 and 10, and a further application of the information gleaned by the methods of the invention is illustrated in Example 11.

After identifying a specific mutation that is associated with a particular HRD disease, that information can then be used to design an oligonucleotide useful as a diagnostic tool to screen other individuals for that particular disease. The oligonucleotide can take the form of a hybridization probe (described in Example 2) or a primer for PCR amplification (described in Example 3). Such hybridization probes could range in size from six to 10,000 nucleotides (preferably 13 to 20 nucleotides), while PCR primers could range from ten to 1000 nucleotides (preferably 8 to 25 nucleotides).

If either such screen reveals that the mutation appears in some patients with an autosomal dominant HRD disease but in no unaffected individuals of a statistically significant sample, it can be presumed that the existence of that mutation in the DNA of any tested individual will be informative for the inherited propensity to develop one form of autosomal dominant HRD disease. An oligonucleotide which includes the mutant sequence will be useful as a diagnostic tool for screening individuals for that form of the disease. A genetic screening test based on this oligonucleotide, and further including a second oligonucleotide with the normal sequence could be useful not only to detect those homozygous for the mutation (and thus destined to develop the disease), but also those heterozygous for the mutation (and thus carriers of the disease trait).

A genetic screening test can also be used to identify individuals with autosomal recessive HRD disease, and/or to identify compound heterozygotes. In the latter case, two different mutations, each affecting different copies of the disease gene, are present in the affected patients of a sibship. Each of the two mutations comes from one parent. This is the case for the two mutations of the PDE β gene that are presented in Examples 9 and 10.

A further application of the information gleaned by the method of the invention is illustrated in Example 4, wherein is described the creation of a transgenic animal bearing a gene for a mutant form of a human photoreceptor protein. This animal is designed to serve as an animal model for a particular HRD disease.

Rhodopsin

EXAMPLE 1

Figure 1A:
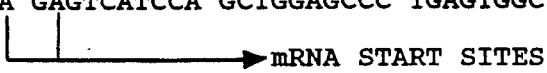

The nucleotide sequence for the normal human rhodopsin gene has been published (Nathans and Hogness, Proc. Natl. Acad. Sci. USA 81:4851–4855, 1984; also Genbank Accession No. K02281, EMBL ID:HSOPS), and is shown in FIG. 1 (without introns) (SEQ ID NO: 1) and FIG. 2 (with introns)(SEQ ID NO: 2). Using this sequence information, four pairs of 20-base oligodeoxyribonucleotides having the sequences shown in FIG. 2 (SEQ ID NO: 2) were synthesized using an automated DNA synthesizer (Pharmacia Gene Assembler), following manufacturer's instructions. The pair with the sequences numbered 348 and 349 in FIG. 2 were designed to prime the PCR amplification of exon 1 of the rhodopsin gene, 346 and 347 to prime exon 2, 344 and 345 to prime exons 3–4, while 350 and 351 were designed to prime the translated sequence within exon 5.

Figure 3:
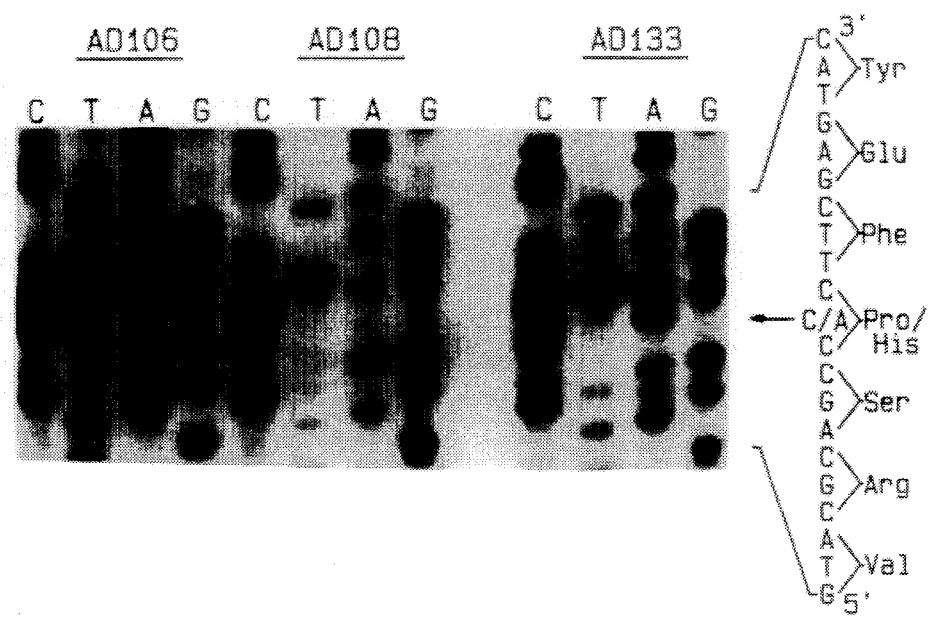

Twenty unrelated patients with autosomal dominant RP were selected from families whose affected members had delayed rod ERG responses and either normal or delayed cone ERG responses. A 0.05 to 0.5 μg sample of leukocyte DNA from each patient was amplified using 35 cycles in an automated PCR machine (Ericomp Programmable Cyclic Reactor) and one of the pairs of oligonucleotide primers listed above. This amplification process was repeated for each patient using each of the other pairs of oligonucleotide primers. Sequence analysis of the resultant amplified DNA using the method of Yandell and Dryja (Cold Spring Harbor Symposium Series: Cancer Cells 7-Molecular Diagnostics of Human Cancer; eds. Furth and Greaves, 223–227, Cold Spring Harbor Press, Cold Spring Harbor, N.Y., 1989, hereby incorporated by reference) revealed that five of the 20 patients were heterozygous for the same C-to-A transversion within codon 23 of the rhodopsin gene (for example, see AD133 in FIG. 3).

EXAMPLE 2

Using the rhodopsin mutation sequence information described in Example 1, two 19-nucleotide oligonucleotide hybridization probes [shown in FIG. 4(a) (SEQ ID NO: 3) and (b) (SEQ ID NO: 4)]and two having 15 nucleotides each [FIG. 4(c) (SEQ ID NO: 5) and (d) (SEQ ID NO: 6)] were then synthesized. The sequences of two of these oligonucleotides [FIG. 4(a) (SEQ ID NO: 3) and (c) (SEQ ID NO: 5)] match the sequences of codon-23-containing segments of the mutant rhodopsin gene, while the sequences of the other two probes [FIG. 4(b) (SEQ ID NO: 4) and (d) (SEQ ID NO:

6)] match the sequences of the corresponding segments of the normal rhodopsin gene. The 19mer probes illustrated in FIG. 4(a) (SEQ ID NO: 3) and (b) (SEQ ID NO: 4) constitute the pair of probes utilized for some of the hybridization tests described herein; the 15mer pair of probes illustrated in FIG. 4(c) (SEQ ID NO: 5) and (d) (SEQ ID NO: 6) were found to hybridize with the same specificity as the longer probes, and so were substituted for the longer probes in some of the work described herein. Hybridization and washing conditions were identical in all cases, except as specified below.

DNA from each of 148 unrelated patients with autosomal dominant RP, as well as DNA from each of 102 normal individuals who were unrelated to the patients, was screened using one of the pairs of oligonucleotide probes in a hybridization assay, as follows: Leukocyte DNA from each subject was amplified by PCR, using as amplification primers the pair of oligonucleotides flanking exon 1 (primers #348 and #349). The resultant amplified DNA, which included the exon 1 sequences of each subject's two rhodopsin gene homologues, was purified by electrophoresis in a 2% agarose gel (Seakem), denatured in situ by incubating for 20 min in 0.5M NaCl and 0.5M NaOH, and transferred by Southern blotting techniques to a nylon membrane filter (Micron Separations, Inc.) for hybridization analysis. The membranes were baked at 80° C. for 2 hours, then pre-hybridized overnight at 37° C. in 30–50 ml of a solution containing 0.5% SDS, 100 mM sodium pyrophosphate, 5× SSPE (1 liter of 20× SSPE contains: 174 g NaCl, 27.6 g $NaH_2PO_4(H_2O)$, 7.4 g disodium EDTA, pH 7.4), and 5× Denhardts (500 ml of 50× Denhardts contains: 5 g Ficol (M.W. 400,000), 5 g polyvinylpyrolidone, and 5 g bovine serum albumin). Each oligonucleotide probe, end-labeled with $32_P$ (using $[\gamma^{-32}P]$-dATP) and polynucleotide kinase (New England Biolabs), was tested for its ability to hybridize with the denatured amplified DNA under highly-stringent conditions, as follows: the pre-hybridization solution was replaced with 5–10 ml of fresh solution containing the labelled oligonucleotide probe; after hybridization for 1–2 hours at 37° C., the filters were washed 4 times at room temperature in a solution of 0.5×SSC and 0.1% SDS; and then washed for 20 minutes at 57° C. (for the 19 mer probes) or 53° C. (for the 15 mer probes) in a solution of 3M tetramethylammonium chloride, 50 mM Tris (pH 8.0), 2 mM EDTA, and 0.1% SDS. The filters were then rinsed at room temperature with fresh aliquots of the same wash solution, blotted on Whatman 3M paper, wrapped in clear plastic wrap (Saran Wrap), and autoradiographed, with exposures generally for 2–40 hours at −70° C., using an intensifying screen. As the washing procedure utilized removes unhybridized labeled probe from the filter but leaves in place on the filter any probe which has hybridized to the amplified rhodopsin DNA, autoradiographic analysis of the filter detects only hybridized probe. Hybridization of the mutation-containing probe [FIG. 4(a) (SEQ ID NO: 3) or (c) (SEQ ID NO: 5)] with a given sample of DNA indicates the presence of that mutation in the genome of the person from whom the sample was derived. Of the 148 RP patients tested, 17, including the original five who had previously been identified by sequence analysis as bearing the mutation, carried the C-to-A base change in codon 23 of the rhodopsin gene, whereas none of the 102 normal individuals tested carried it ($\chi_1^2=12.57$, $p<0.001$). This result effectively rules out the possibility that this nucleotide change represents a DNA polymorphism with no relationship to RP.

Figure 5:
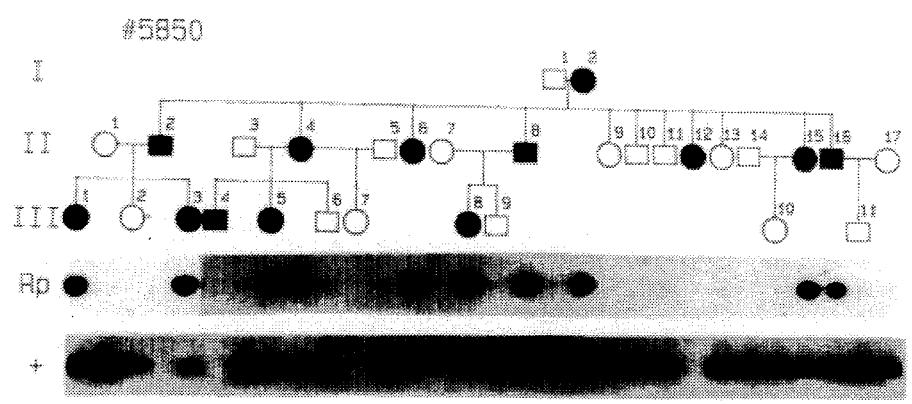
FIG. 5 is an illustration of the inheritance of RP within one family (designated pedigree #5850), showing the hybridization of amplified rhodopsin gene exon 1 DNA obtained from each indicated individual with (1) an oligonucleotide probe bearing the mutant sequence within codon 23 (line marked "RP") or (2) an oligonucleotide with the normal sequence (line marked "+").

The potential utility of these probes to screen for inheritance of this form of RP is illustrated by a study of inheritance within a single family, family #5850. As shown in the autoradiograms across the bottom of FIG. 5, the C-to-A mutation ("Rp") is present in amplified leukocyte DNA from all affected members (solid symbols) who were tested, but in none of the amplified DNA samples from unaffected members (open symbols) who were tested. Leukocyte DNA for testing was unavailable from individuals II-2, II-12, III-4, and III-7.

Figure 6:
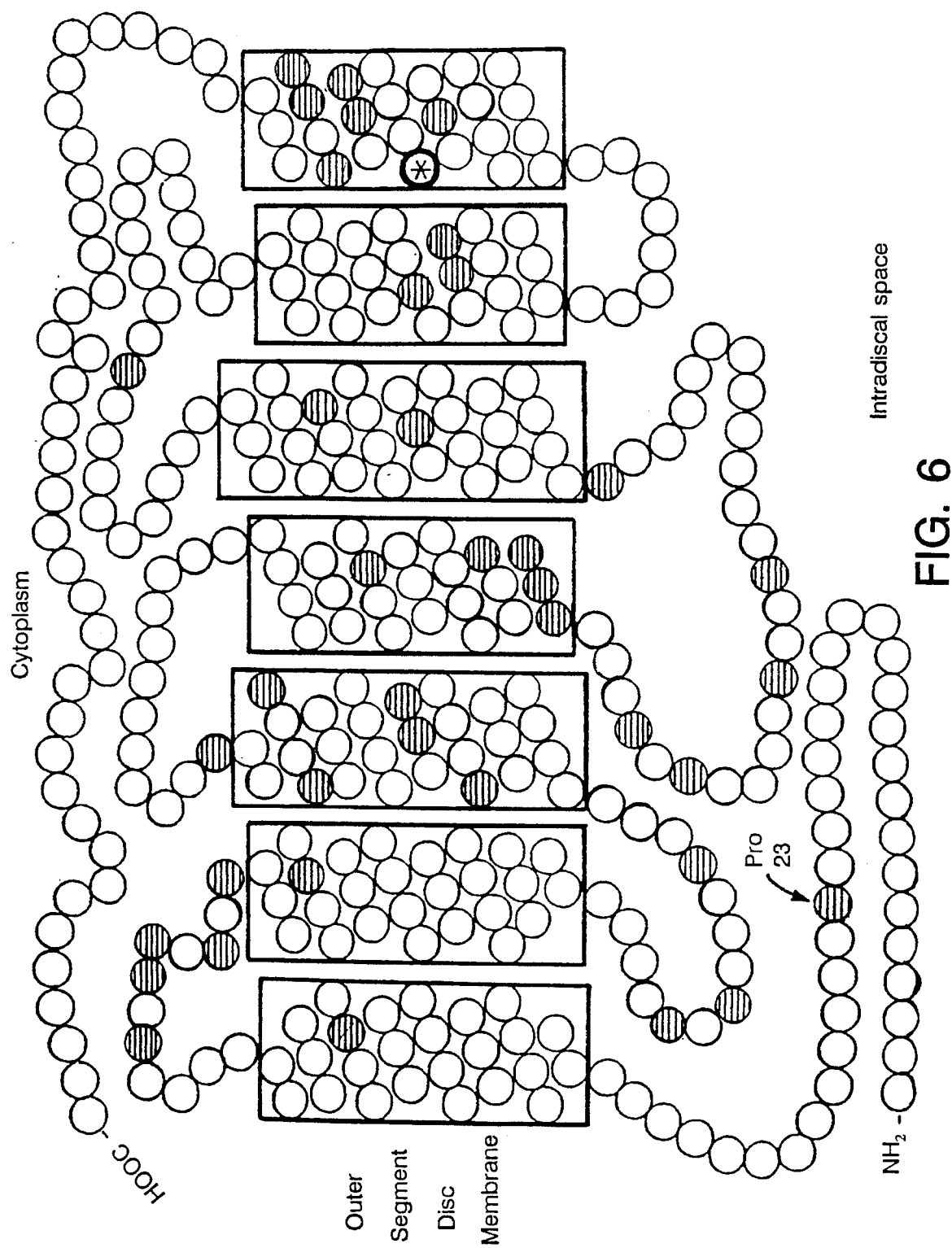
FIG. 6 is a schematic representation of the approximate arrangement of the rhodopsin molecule in relation to the rod outer segment disc membrane.

Rhodopsin codon 23 normally codes for a proline within the amino-terminal region of rhodopsin (FIG. 6). The precise function of this region of the rhodopsin protein is unknown, but the proline at this position is invariate among the vertebrate and invertebrate opsins, as well as among molecules such as the beta-2 adrenergic receptor that have homology with the opsins. In view of the conservation of proline at this position, the nucleotide change found in codon 23 (i.e., the substitution of the charged amino acid histidine for the nonpolar proline) was predicted to result in a dysfunctional or absent rhodopsin molecule that would affect rod function.

This prediction is consistent with ERG findings in family #5850. FIG. 7 illustrates normal ERG responses from an unaffected member (III-2, age 28) and abnormal responses from two affected siblings and an affected aunt (III-3, age 24; III-1, age 29; and II-4, age 52). The techniques used to obtain the ERG data are as described by Berson et al. (Arch. Ophthalmol. 80:58–67, 1968) and Reichel et al. (Am. J. Ophthalmol. 108:540–547, 1989). Stimulus onset is indicated in the left and middle columns of FIG. 7 by vertical hatched lines, and in the right column by a vertical line. Two or three consecutive sweeps are superimposed. Cornea positivity is indicated by upward deflection. Oblique arrows in the middle column designate delayed rod-dominated peaks. Horizontal arrows in the right column designate cone response times (i.e., time interval between stimulus flash and corresponding cornea-positive response peak). Under these test conditions, normal amplitudes are ≧100 µV for single flashes of blue light, ≧350 µV for single flashes of white light, and ≧50 µV for 30 Hz white flicker; normal cone response times are ≦32 msec. The calibration symbol in the lower right corner of FIG. 7 designates 50 msec horizontally and 100 µV vertically.

The recordings in the left column of FIG. 7 show the response to flashes of dim blue light, a measure of rod function. The two affected siblings have a markedly reduced response of the rods compared to the response shown by their unaffected sister. The middle column of FIG. 7 shows the response to single flashes of white light, which normally elicit a response from both rods and cones. The cone-dominated and the rod-dominated ERG peaks recorded by the 28-year old normal member occurred at the same time and cannot be distinguished, while her two affected siblings exhibit a splitting of the response into an early, cone-dominated peak and a delayed, rod-dominated peak of reduced amplitude (see oblique arrows in FIG. 7). This splitting results from a relatively normal cone response time but delayed rod response time. The right column of FIG. 7 shows the ERG responses of the four family members to flickering (30 Hz) white light; this is a measure of cone function, since only cones can respond to light flashes of this frequency. In this test, the 24-year-old affected sibling demonstrates a normal amplitude and response time similar to that of her unaffected sister, while the 29-year-old affected sibling, with more advanced disease, has a slightly reduced amplitude and borderline delayed response time (see horizontal arrows). The ERG findings in the two affected siblings are consistent with the predominant involvement of rods in the early stages of this form of autosomal dominant RP, as one might expect from a defect in rhodopsin, a protein that is thought to be associated exclusively with rods. Late in this disease, there is loss of cone and rod function, illustrated by the profoundly reduced responses in all three columns from the 52-year-old affected aunt.

EXAMPLE 3

Instead of using radioactively labelled hybridization probes to screen genomic DNA for the mutation in codon 23 of the rhodopsin gene, as described in Example 2, the inherent disadvantages of radioactive reagents may be avoided entirely by screening instead with a method which uses PCR primer discrimination to indicate the presence of a mutant allele. This method was used to screen samples of genomic DNA for the C-to-A transversion in codon 23 of rhodopsin, as follows:

Two pairs of 20-base oligonucleotide primers were synthesized and used to prime PCR amplification of a 151-bp segment of rhodopsin DNA from each patient to be screened. One of the pairs is shown in FIG. 8 (SEQ ID NO:7) as the boxed sequences numbered 348 and 502, with oligonucleotide #502 including as its 3' nucleotide the (G) corresponding to the normal sequence found in the antisense strand of codon 23. The second pair of primers is shown in FIG. 8 (SEQ ID NO: 7) as the boxed sequences numbered 348 and 485, with oligonucleotide #485 identical to #502 except that its 3' nucleotide is (T), corresponding to the mutant sequence for the antisense strand of codon 23. A perfect match of primer to template at the 3' nucleotide of each PCR primer is known to be particularly important for efficient amplification of the intervening template DNA. Thus, the 348/485 pair of primers will be capable of efficiently priming amplification only of DNA containing the mutant allele, while the 348/502 pair will efficiently prime amplification only of DNA which has the normal sequence in codon 23 of the rhodopsin gene, i.e. the normal allele. Efficiency of priming is measured as follows:

A 50 ng sample of leukocyte genomic DNA from an individual to be screened is combined with 20 picomoles of primer #348 and 20 picomoles of primer #485 in a total volume of 50 µl PCR reaction solution (50 mM KCl, 20 mM Tris pH 8.4, 0.1 µg/µl bovine serum albumin, 1.0 mM $MgCl_2$, and 200 µM of each of dATP, dCTP, dGTP and dTTP). A second 50 ng sample of genomic DNA from the same individual is similarly combined with 20 picomoles of primer #348 and 20 picomoles of primer #502 in 50 µl PCR solution; both samples are overlaid with 50µl sterile mineral oil and simultaneously subjected to the same thermal cyclic reactor block in an automated PCR machine (Ericomp Programmable Cyclic Reactor) under the following temperature conditions: 93° C. for 2 min; 35 repetitions of the cycle: 46° C. for 10 sec, 71° C. for 30 sec, and 93° C. for 20 sec; and finally, one cycle of 46° C. for 90 sec, 71° C. for 4 min. Mineral oil is removed by extracting with 55 µl of a solution of 96% chloroform and 4% isoamyl alcohol. Seven µl of the amplified product is electrophoresed through a 2% agarose gel with appropriate size markers, stained with ethidium bromide, and either photographed or observed directly under ultraviolet illumination. Only DNA which has been efficiently amplified will form a clearly stained band on the gel. Thus, only those individuals who carry the mutant allele will show a visibly stained band in the lane corresponding to the 348/485 primer pair. Both normal individuals and those heterozygous for the mutant allele will produce a distinct band of amplified DNA in the 348/502 lane. As a control, two samples (one for each pair of primers) from an individual known to carry the mutant allele are always amplified alongside the test sample. In FIG. 9, DNA from three patients, two (lanes 1 and 6, and lanes 2 and 7, respectively) having both a normal and a mutant allele, and a third (lanes 3 and 8) having two normal alleles, was amplified by PCR using either the 348/485 primer pair (lanes 1, 2, and 3) or the 348/502 primer pair (lanes 6, 7, and 8); the patients bearing the mutant allele showed efficient priming with either primer pair, while the homozygous normal individual produced a distinct band only when 348/502 primer pair was used (lane 8) and not when the 348/485 primer pair was used (lane 3).

EXAMPLE 4

In order to create an animal model for human RP, the gene encoding the mutant form of human rhodopsin characterized above was first isolated by screening a genomic DNA library prepared from a sample of DNA obtained from an RP patient who had been shown by the method of the invention to carry the C-to-A transversion in one allele. The probe used to screen the library was a 6 kilobase DNA fragment that encodes the entire normal rhodopsin gene, including its transcriptional and translational control elements. Given the length of the probe, it would be expected to hybridize equally well with the mutation-containing rhodopsin allele and the normal allele, so of the clones from this library which hybridize to the probe, one half are expected to represent the mutant gene. Positive clones can then be further screened to identify the mutant allele by using either the probes of Example 2 or the PCR primers of Example 3. Once the mutant rhodopsin gene is isolated, it will be introduced into a mouse embryo in accordance with the method of Leder et al. (U.S. Pat. No. 4,736,866, herein incorporated by reference). The strain of transgenic mice which results will bear one gene for mutant human rhodopsin and two for normal mouse rhodopsin; crossing two such mice will yield some offspring which bear two mutant human alleles and two normal mouse alleles, the 1:1 proportion which in humans results in autosomal dominant RP. It is expected that such a genotype will result in expression of a phenotype resembling human RP, thus providing an invaluable means to study in detail the nature of the disease, and to test potential therapies.

Retinal Degeneration Slow Gene

EXAMPLE 5

Starting with a murine cDNA clone corresponding to the wild type RDS sequence (Travis et al., 1989, Nature 338:70), the corresponding human cDNA sequence from a human retinal cDNA library was isolated. The longest cDNA clone (pHRDS8) spanned the entire open reading frame. This probe detects at least three di-allelic RFLPs (ApaI, DraI, BglII) at the RDS locus, each with a minor allele frequency greater than 0.20 based on a set of 108 "control" individuals without retinitis pigmentosa or a family history of the disease (Travis et al., 1991, Genomics 10:773). The probe pHRDS8 and its cognate RFLPs were used in a search for defects in this gene in retinitis pigmentosa.

The investigation was limited to the autosomal forms of retinitis pigmentosa after mapping the RDS locus to human chromosome 6p (Travis et al., 1991, supra). Patients found to have a mutant rhodopsin gene were excluded from this study, since such mutations are the cause of dominant retinitis pigmentosa in 20–30% of families (Dryja et al., 1990, Nature 343:364; Dryja et al., 1990, New. Engl. J. Med. 323:1302; Inglehearn et al., 1991, Am. J. Hum. Genet. 48:26; Keen et al., 1991, Genomics 11:199; Sung et al., 1991, Proc. Natl. Acad. Sci. USA 88:6481; Sheffield et al., 1991, Am. J. Hum. Genet. 49:699). A search was conducted for gene deletions or rearrangements among 106 unrelated patients with dominant retinitis pigmentosa and 126 unrelated patients with recessive retinitis pigmentosa, using Southern blotting techniques. No aberrant restriction fragments were observed, making it unlikely that deletions or gene rearrangements with breakpoints in the RDS locus are a common cause of dominant or recessive retinitis pigmentosa. A concurrent tabulation of RFLP alleles in these sets of patients provided one note-worthy result: There was an overrepresentation of the minor allele of the ApaI RFLP in the set of unrelated dominant patients (but not in the recessive patients). In fact, 52 out of 106 patients with dominant retinitis pigmentosa carried this allele vs. an expected 39.5 (Chi-square=6.31; df=1; 0.02>p>0.01).

EXAMPLE 6

To determine whether some patients with dominant retinitis pigmentosa had mutations beyond the resolution of the Southern blotting techniques, an intron/exon map and a partial restriction map of the RDS locus was constructed (FIG. 12). This was accomplished by probing a human genomic library in the bacteriophage vector EMBL3 with pHRDS8. Out of $10.9 \times 10^6$ clones that were screened, 137 clones hybridized to the probe. Six of these were plaque purified, amplified and mapped. A consensus restriction map and the number and location of the exons was determined using standard methods. Restriction fragments containing exons were subcloned in plasmids and used as templates for obtaining intron sequences.

Pairs of oligonucleotide primers were synthesized in order to amplify segments of the coding sequence from genomic DNA using the polymerase chain reaction. The amplified sequences were screened for mutations using the technique called "SSCP" analysis (single strand conformation polymorphism) described in Orita et al. (1989, Genomics 5:874, hereby incorporated by reference). Three variant bands found during this investigation are of special interest. Each of these variant bands is due to an alteration in the DNA sequence that changes the encoded amino acid sequence (FIGS. 13A, 13B, and 13C). One variant is a three base deletion that precisely eliminates codon 219 of RDS which normally specifies proline (patient AD206 FIG. 13A). The second changes the specificity of codon 216 RDS from proline to leucine (patient AD32 FIG. 13B), while the third changes the specificity of codon 185 RDS from leucine to proline (patient AD8 FIG. 13C). The mutations in patients AD206 and AD32 were near the 5' end of exon 2, which was amplified by the polymerase chain reaction using the following primers: sense (derived from 3' end of the first intron), 5'-AAGCCCATCTCCAGCTGTCT-3' (SEQ ID NO: 21); antisense (derived from the middle of exon 2'), 5'-TCGTAACTGTAGTGTGCTGA-3' (SEQ ID NO: 22). The mutation in patient AD5 was near the 3' end of exon 1 which was amplified with the following primers: sense (derived from exon 1), 5'-TATGCCAGATGGAAGCCCTG-3' (SEQ ID NO: 23); antisense (derived from the 5' end of the first intron), 5'-TCTGACCCCAGGACTGGAAG-3' (SEQ ID NO: 24). The amplified DNA was directly sequenced using published methods (Yandell et al., 1989, supra).

The SSCP analysis was performed according to a modification of a published method (Orita et al., 1989, Genomics 5:874, hereby incorporated by reference), using the primers noted in the above paragraph (SEQ ID NOS: 21–24), except that the sense primer for family #6935 was 5'-AGTACTAC-CGGGACACAGAC-3'(SEQ ID NO: 25). DNA fragments were amplified by the polymerase chain reaction and either digested with DdeI (for family #6948), with BstNI (for family #6935), or not at all (for family #6459) before being denatured and separated by electrophoresis through a nondenaturing 6% acrylamide gel.

The first two variants, termed Pro219del and Pro21Leu, were found in only one patient each (AD206 and AD32, respectively) in an expanded set of 139 unrelated patients with dominant retinitis pigmentosa (all without a rhodopsin mutation), while the third, Leu185Pro, was found in two unrelated patients (AD8 and AD145) from that set. None of these variants was found among an additional 52 unrelated patients with autosomal dominant retinitis pigmentosa who carry a rhodopsin mutation. None was present among 100 unrelated "control" individuals without retinal degeneration. The relatives of three of these patients donated blood for analysis: in each family, the presence of the abnormality invariably correlated with the disease (FIGS. 14A, 14B, and 14C). Each of the three variations therefore represents a mutation that causes autosomal dominant retinitis pigmentosa due to a defect in the RDS gene.

EXAMPLE 7

FIG. 15 displays the ERGs from an unaffected, "control" individual and patients with each of the three mutations. The left column shows the retinal response to a flash of dim blue light used to determine rod function. The middle column shows the response of both rods and cones to single flashes of bright white light. The right column provides the retinal response to flickering (30 Hz) white light; since rods cannot respond to this flicker frequency, this is a measure of cone function. As illustrated in this figure, all patients with the mutations described here had abnormal ERGs. Young patients had moderately reduced amplitudes and delayed response times. This is compatible with the notion that mutations in the RDS gene affect both rods and cones. Older patients with advanced disease had profound reductions of both rod and cone amplitudes.

EXAMPLE 8

The RDS gene represents the second human locus, after rhodopsin (Dryja et al., 1990, Nature 343:364; Dryja et al., 1990, New Engl. J. Med. 323:1302; Inglehearn et al., 1991, Am. J. Hum. Genet. 48:26; Keen et al., 1991, Genomics 11:199; Sung et al., 1991, Proc. Natl. Acad. Sci. USA 88:6481; Sheffield et al., 1991, Am. J. Human Genet. 49:699), at which mutations are known to cause autosomal dominant retinitis pigmentosa. The product of this gene is a membrane-associated glycoprotein confined to the photoreceptor outer segments (Travis et al., 1991, Neuron 6:61; Connell et al., 1991, Proc. Natl. Acad. Sci. USA 88:723; Connell et al., 1990, Biochem. 29:4691). Based on the phenotype of the rds strain of mice and on the initial biochemical characterization, the protein is probably involved with maintaining the structure of outer segment discs. The mRNA sequence has been determined in mouse (Travis et al., 1989, supra), human (Travis et al., 1991 Genomics 10:773), cow (Connell et al., 1991, supra), and rat (Begy et al., 1990, Nucl. Acids Res. 18:3058). The three amino acids affected by the mutations described herein are probably located within the second intradiscal loop as shown in FIG. 16 (Travis et al., 1991, Neuron 6:61; Connell et al., 1991, supra; Connell et al., 1990, supra). This is a domain of the retinal degeneration slow protein that is very highly conserved among these four mammalian species. In particular, the three residues involved by these mutations are invariant. The region also contains the only glycosylation site conserved in all four species. Substitutions in RDS between proline and leucine, or the loss of a proline residue, are non-conservative changes that can be expected to have major effects on the secondary structure of the RDS protein.

The β-Subunit of cGMP Phosphodiesterase

EXAMPLE 9

Again using SSCP analysis (Dryja et al., Proc. Natl. Acad. Sci. USA 88:9370–9374, 1991; Orita et al., 1989, supra), seven of the 22 exons of the PDE β gene were screened for genetic mutations.

Ninety-nine unrelated patients with autosomal recessive retinitis pigmentosa (exons 3, 5, 6, 7, 12, 13, 14; representing 221 out of 854 codons) were screened. Each patient had either unaffected parents and at least one affected sibling, or were the offspring of a consanguineous mating. If the patient and the affected sibling were both male, an ophthalmologic exam and an ERG of the mother were performed to rule out the possibility of X-linked disease. No patient included in the screen had defects in the rhodopsin gene as detected by SSCP. All patients had reduced and delayed or absent rod ERG responses. A control group of 100 unrelated individuals was selected on the basis of no personal or family history of retinitis pigmentosa. Informed consent was obtained from all participants. Leukocyte nuclei were prepared from between 10 and 50 ml of venous blood as described previously (Kunkle et al. Proc. Natl. Acad. Sci. USA 74:1245–1249, 1977). These nuclei were stored at –70° C. prior to DNA purification and analysis.

DNA was amplified by PCR, using the following pairs of oligonucleotide primers based on the PDE β sequence of Weber et al. (Nucleic Acids Res. 19:6263–6268, 1991, hereby incorporated by reference) and Riess et al. (Nature Genetics 1:104–108, 1992): exon 5: sense 5'-ACCGC-CCCACCCTCACCTCT-3' (SEQ ID NO:13), antisense 5'-CCCTATCCCTCCCTCTCCTG-3' (SEQ ID NO:14); exon 12: sense 5'-CCTCCCTCAGCCCACAATCC-3' (SEQ ID NO:15), antisense 5'-TGACTATGCGCCTGCGGTGT-3' (SEQ ID NO:16); and exon 13: sense 5'-GCGCTCTG-GCGGGACTTACA-3' (SEQ ID NO:17), antisense 5'-GC-CTGCACAACCCTGGTGAT-3' (SEQ ID NO:18). The pH, $Mg^{+2}$ concentration, and annealing temperature for PCR of each primer pair was as follows: pH 8.4, 0.75 mM $MgCl_2$, 63° C. (exon 5); pH 8.4, 1 mM $MgCl_2$, 63° C. (exon 12); and pH 8.4, 1 mM $MgCl_2$, 63° C. (exon 13). The resulting DNA fragments, 191 bp, 203 bp, and 204 bp, respectively, were heat-denatured and single-stranded fragments were separated by electrophoresis at room temperature through 9% polyacrylamide gels with or without 10% glycerol. Gels were run at 30 W for 6 to 11 hours before drying and autoradiography.

Direct DNA sequencing was performed as follows. The mutation encoding Gln298X of PDE β is located in exon 5 and was amplified by polymerase chain reaction using the following primers: sense 5'-CCCTGCTGCTGTGGTCA-GAC-3' (SEQ ID NO:19); antisense 5'-CCCTATCCCTC-CCTCTCCTG-3' (SEQ ID NO:14). The mutation encoding Arg531X PDE β is located in exon 12 and was amplified with the primers: sense 5'-CCTCCCTCAGCCCACAATCC-3' (SEQ ID NO:15); antisense 5'-CCTCTAAACTTCCT-GTGGGA-3' (SEQ ID NO:20). The pH, $Mg^{+2}$ concentration, and annealing temperature for PCR of the primer pairs was as follows: pH 8.6, 1 mM $MgCl_2$, 58° C. (exon 5); and pH 8.6, 0.5 mM $MgCl_2$, 48° C. (exon 12). Using published methods (Yandell et al. 1989, supra), the amplified DNA of exons 5 and 12 were sequenced directly with the radioactively labelled primers: antisense 5'-CCCTATCCCTC-CCTCTCCTG-3' (SEQ ID NO:14) and antisense 5'-TGAC-TATGCGCCTGCGGTGT-3' (SEQ ID NO:16), respectively.

Direct genomic sequencing of variant bands identified four mutations in the open reading frame of PDE β: a C-to-T transition at position 11638 of the Weber et al. sequence (1991, supra) in exon 5 resulting in a nonsense mutation (Gln298X) in patients AR77 and AR120 (FIG. 17A); a C-to-T transition at position 18086 of the Weber et al. sequence (1991, supra) in exon 12 resulting in a nonsense mutation (Arg531X) in patient AR77 (FIG. 17B); a one base pair deletion at position 17981 of the Weber et al. sequence (1991, supra) in exon 12 (pro496(1bp del)) and a C-to-T transition at position 19876 of the Weber et al. sequence (1991, supra) in exon 13 resulting in a missense mutation (his557Tyr) in patient AR67. None of these mutations were found among a group of 100 control individuals without retinitis pigmentosa.

SSCP analysis of DNA from the relatives of AR77 (family 6193, FIGS. 13A), reveals that the two affected family members carry both Gln298X and Arg531X in PDE β. None of the unaffected siblings carries both mutations. Their mother is heterozygous for Gln298X, while their father is heterozygous for Arg531X, indicating that the mutations are nonsynthenic. Gln298X and Arg531X are likely to be null alleles since neither of the predicted PDE β proteins would contain the putative catalytic domain within residues 555 to 792 (Charbonneau et al., Proc. Natl. Acad. Sci. USA 83:9308–9312, 1986; Charbonneau et al., Proc. Natl. Acad. Sci. USA 87:288–292, 1990). Gln298X of PDE β also cosegregates with autosomal recessive retinitis pigmentosa in the relatives of AR120 (family 6235, FIG. 18B). Both affected family members are heterozygous for this PDE β mutation; however, a second mutation of the homologous allele is yet to be identified in this kindred.

In a third family, 3713, patient AR67 and her affected sister heterozygously carry both Pro496(1bp del) and His557Tyr, both of PDE β (FIG. 18C). The mother carries only one of these defects (His557Tyr), indicating that the two mutations are nonsynthenic (a blood sample from the father was not available). The Pro496(1 bp del) mutation results in a predicted mutant protein with a premature stop at codon 574. This protein, if expressed by photoreceptors, is probably nonfunctional since the putative catalytic domain would have numerous, altered amino acid residues and the carboxy end would be truncated. The nonconservative His557Tyr mutation of PDE β removes a positively charged residue near the glycine-rich loop within the putative catalytic domain. A histidine at position 557 is present in human, bovine, and murine PDE β; human and bovine PDE β, and bovine PDE α (Collins et al., Genomics 13:698–704, 1992; Li et al., Proc. Natl. Acad. Sci. USA 87:293–297, 1990). The nonsynthenic alleles, Pro496(1bp del) and His557Tyr of PDE β cosegregate with autosomal recessive retinitis pigmentosa in this kindred.

EXAMPLE 10

Clinical Findings

The patients with mutations in the PDE β gene (6193:II-3 and II-5; 6235:II-1 and II-2; 3713:II-2) had clinical findings typical of retinitis pigmentosa. They reported absent night vision since early childhood. All had best-corrected visual acuity of 20/40 or better, and visual fields constricted to about a 20° diameter with or without peripheral islands. Final dark adapted thresholds were elevated 2 or more log units. Ophthalmoscopy revealed attenuated retinal vessels and typical intraretinal bone-spicule pigment around the midperiphery.

Full-field electroretinography was performed using a contact-lens electrode placed on the topically anesthetized cornea after pharmacologic dilation of the pupils and adaptation to the dark for 45 min. The responses were electronically amplified, displayed on an oscilloscope, and photographed as described previously (Berson et al. 1968, supra; Andreasson et al. Am. J. Ophthalmol. 105:500–503, 1988). The rod amplitude versus retinal illuminance functions were plotted as described previously (Rosenfeld et al. Nature Genetics 1:209–213, 1992; Sandberg et al. Invest. Ophthalmol. Vis. Sci. 31:2283–2287, 1990). Responses to flashes of dim blue light (left column), mixed cone-rod responses to flashes of white light (middle column), and cone isolated responses to 30 Hz white flickering light (right column) are illustrated in FIG. 19. Stimulus onset is marked by vertical dotted lines in the left and middle columns and by short vertical lines in the right column. Two or three consecutive sweeps are superimposed in each column. Horizontal arrows in the left and right columns show road and cone response times, respectively. Under these test conditions, the normal amplitudes are $\geq 100$ μV (left column), $\geq 350$ μV (middle column), and $\geq 50$ μV (right column); normal rod response time is $\leq 108$ ms, and normal cone response time is $\leq 32$ ms. Calibration symbol (lower right) shows 50 ms horizontally, 100 μV vertically (left column), 200 μV vertically (middle column), and 100 μV vertically (right column, except for II-3 and II-5 in which the vertical designates 1 μV with computer averaging to show delayed response times). Responses to blue light were not available for AR77.

ERG recordings revealed no detectable rod responses to dim blue light in patietns with mutations in the PDE β gene (see, e.g., family 6193 in FIG. 19). Responses to single flashes of white light were markedly reduced in amplitude, indicating loss of rod and cone function. Cone-isolated responses to white flickering light, monitored with computer averaging, were reduced and delayed.

It was determined whether heterozygous carriers of a defective PDE β allele (e.g., the parents and some unaffected siblings in these families) express a reduced amount of functional enzyme in their rods that leads to a subtle photoreceptor dysfunction. The carriers with known mutations who were examined (6193: I-1 and I-2) reported no difficulty with night vision and had no fundus findings of retinitis pigmentosa. Their rod-isolated responses to flashes of dim blue light and cone-isolated responses to flickering white light were minimally if at all reduced and minimally if at all delayed (FIG. 19). To examine rod function more closely in these two carriers, the amplitude of the rod b-wave was plotted as a function of the intensity of the stimulating flash of light (Rosenfeld et al., supra; Sandberg et al., 1990, supra). The light intensity that produced a half-maximal rod response in these patients was approximately equal to that found in normal controls, suggesting that the sensitivity of rods to light flashes was normal. By contrast, the maximum rod signal was reduced by 37% ($P=0.003$).

EXAMPLE 11

In order to create an animal model for hereditary retinal degenerative disease characterized by mutations in the RDS locus or in the gene encoding PDE β, genes encoding any of the mutations described above can be isolated by screening a genomic library prepared from a sample of DNA obtained from individuals carrying such mutations, using the probes that are described above. The general methodology for production of non-human transgenic animals is described in Example 4. Animals so produced will provide an invaluable means to study in detail the nature of the disease, and to test potential therapies.

Other Embodiments

Other embodiments are within the following claims. For example, the method disclosed herein for identifying the precise genetic abnormality responsible for a given HRD disease could be utilized for further studies on a gene encoding a photoreceptor protein, e.g., the rhodopsin gene, the RDS gene, and the PDE β gene, with the goal of identifying mutations other than the one described in the examples above. In particular, since only 7 of the 22 exons of PDE β have been screened, it is likely that additional mutations will be found in the PDE β gene when other exons are screened, e.g., by using the methods provided herein. Such mutations might include, besides point mutations similar to the C-to-A transversion or the C-to-T transitions described above, deletions, additions, or rearrangements of one or more nucleotides. The method could be applied to genes encoding other photoreceptor proteins besides rhodopsin, RDS, or the PDE β gene, or for other eye-related proteins with a possible role in HRD disease. For example, genes encoding the following human photoreceptor proteins have been cloned and sequenced and thus could be analyzed by the method of the invention to determine whether or not a mutation in any such gene is associated with some form of the disease. The relationship between many of the enzymes of the phototransduction cascade, as well as structural proteins of the photoreceptor outer segment, is shown in FIG. 20. Of particular interest are each of the three cone visual pigments (Nathans et al., Science 232:193, 1986); interphotoreceptor retinal binding protein (Fong and Bridges, J. Biol. Chem. 263: 15330, 1988); retinal S-antigen (also referred to as "arrestin"; Yamaki et al., FEBS Lett. 234: 39, 1988); the α-subunits of rod-transducin and cone-transducin (Lerea et al., Science 234:77, 1986); RDS (labelled in FIG. 20 as "peripherin"), PDE β, and the α- and γ-subunits of retinal cGMP phosphodiesterase (for which the cDNA sequence and the corresponding amino acid sequence of the longest open reading frame are shown in FIG. 10 (SEQ ID NO: 8) and FIG. 11 (SEQ ID NO: 9), respectively; this DNA sequence was determined by sequencing a cDNA clone obtained by probing a human retina cDNA library with a synthetic oligonucleotide probe, the sequence of which was derived from a conserved region found to be identical in two previously-cloned homologs of the gene, the bovine and the murine versions). Genetic linkage studies will in some cases suggest likely gene candidates for analysis by the method of the invention, as where the inherited trait maps to the same chromosomal location as a particular cloned and sequenced gene. If such map information is not available for a given gene or HRD disease, then a bank of appropriate PCR primers representing all suspected genes can be used by applying the methods of the invention in a brute-force search for the causative mutation. Where the DNA sequence of a given photoreceptor protein-encoding gene is not known, it can be determined by standard cloning and DNA sequencing techniques well known to those of ordinary skill in the art (see, e.g., Maniatis et al., Molecular Cloning: A Laboratory Manual. Cold Spring Harbor Laboratory, Cold Spring Harbor, N.Y., 1982).

Once the mutation responsible for a given HRD disease has been characterized, an oligonucleotide probe or primer incorporating the mutation can be readily synthesized by standard methods; the probe or primer could then be used to screen nucleic acid samples in the same manner as the probe disclosed in the examples above. A second probe or primer having the sequence of the corresponding part of the normal version of the gene may also be synthesized for use as a control capable of hybridizing to, or priming the amplification of, the normal allele. The probe or primers could be longer or shorter than the 19 mers and 15 mers utilized in Example 2 or the 20 mers of Examples 3, 6, or 10, as long as they can clearly differentiate between the mutant allele and the normal allele.

Minor variations in the methods used would also be within the scope of the invention. For example, if a source of mRNA encoding the protein of interest were available from HRD disease patients, cDNA cloning could substitute for PCR as the method used for amplifying the number of copies of mutation-containing DNA in a given DNA sample, in order to generate enough copies for DNA sequence analysis. The probe or primer of the invention may be RNA rather than DNA (although DNA, which is less labile than RNA, would be preferred), and the nucleic acid to be screened using the probe or primer could be mRNA or cDNA (if either is available) instead of genomic DNA. Any suitable animal could be substituted for the mouse of Example 4 and Example 11 in order to produce an animal model for an HRD disease; the method of introducing the heritable human mutant allele into the animal may vary from that specified herein, and still be within the invention: for example, the mutant human gene may be introduced solely into those cells of a developing embryo which are already committed to develop into eye cells, yielding an animal which bears the mutant allele in its eye cells (e.g., retinal cells) but not in the majority of its other cells. The particular form of HRD disease to be investigated may be one that is inherited in an autosomal dominant manner, as is the form of RP discussed in the above examples, or it could be autosomal recessive, X-linked, or mitochondrially (maternally) inherited. Hybridization of the probe or primer to the nucleic acid sample, or efficient amplification of a sample by the probe or primer, could be detected by any appropriate means known to those of ordinary skill in the art.

What is claimed is:

1. A method of diagnosing in a human subject an increased likelihood of developing or transmitting to future generations a disease in which a mutant form of a human photoreceptor protein is a causative agent, said method comprising, analyzing the DNA of said human subject to determine the presence or absence of a mutation in a gene for a protein selected from the group consisting of rhodopsin, retinal degeneration slow (RDS) protein, and the β-subunit of retinal rod cGMP phosphodiesterase, the presence of such a mutation indicating an increased likelihood of developing or transmitting to future generations a disease in which a mutant form of a human photoreceptor protein is a causative agent.

2. The method of claim 1, wherein said DNA is analyzed by amplifying said DNA and identifying said mutation in said amplified DNA.

3. The method of claim 1, wherein said analyzing the DNA of said human subject comprises identifying a single strand conformation polymorphism.

4. The method of claim 1, wherein said analyzing the DNA of said human subject comprises DNA sequencing.

5. A probe or primer consisting of a purified single-stranded oligonucleotide, said oligonucleotide being of 10–50 nucleotides in length and containing a region the sequence of which is identical to the sequence of a six-nucleotide, single-stranded segment of a gene encoding a mutant form of the β-subunit of retinal rod cGMP phosphodiesterase, said segment comprising part or all of a mutation characterizing said mutant form of said gene.

6. The probe or primer of claim 5, wherein said oligonucleotide is DNA.

7. The probe or primer of claim 5, wherein said mutation comprises a change in the codon encoding glutamine 298 of said β-subunit of retinal rod cGMP phosphodiesterase.

8. The probe or primer of claim 5, wherein said mutation comprises a change in the codon encoding arginine 531 of said β-subunit of retinal rod cGMP phosphodiesterase.

9. The probe or primer of claim 5, wherein said mutation comprises a change in the codon encoding proline 496 of said β-subunit of retinal rod cGMP phosphodiesterase.

10. The probe or primer of claim 9, wherein said change is a deletion of a nucleotide from said codon 496.

11. The probe or primer of claim 5, wherein said mutation comprises a change in the codon encoding histidine 557 of said β-subunit of retinal rod cGMP phosphodiesterase.

12. The method of claim 1, wherein said analyzing the DNA of said human subject comprises:

(a) providing a probe or primer consisting of a purified oligonucleotide, said oligonucleotide being of 10–50 nucleotides in length and containing a region the sequence of which is identical to the sequence of a six-nucleotide segment of a gene encoding a mutant form of a protein selected from the group consisting of rhodopsin, retinal degeneration slow protein, and the β-subunit of retinal rod cGMP phosphodiesterase, said segment comprising part or all of a mutation characterizing said mutant form;

(b) exposing said probe or primer to said DNA of said human subject; and (c) detecting hybridization of said probe or primer to said DNA, thereby determining the presence of said mutation in said gene.

13. The method of claim 12, wherein said human subject is a fetus or a patient.

14. The method of claim 12, wherein said method is used to detect a genetic predisposition to develop a hereditary retinal degenerative disease.

15. The method of claim 1, wherein said analyzing the DNA of said human subject comprises (a) providing a probe or primer consisting of a purified oligonucleotide, said oligonucleotide containing a region the sequence of which is identical to the sequence of a six-nucleotide segment of a gene encoding a mutant form of a protein selected from the group consisting of rhodopsin, retinal degeneration slow protein, and the β-subunit of retinal rod cGMP phosphodiesterase, said segment comprising part or all of a mutation characterizing said mutant form;

(b) combining said probe or primer with a second primer and said DNA of said human subject, under conditions permitting amplification of a DNA template comprising said mutation in said gene; and (c) detecting amplification of said DNA template, thereby determining the presence of said mutation in said gene.

16. The method of claim 15, wherein said human subject is a fetus or a patient.

17. The method of claim 15, wherein said method is used to detect a genetic predisposition to develop a hereditary retinal degenerative disease.

* * * * *

UNITED STATES PATENT AND TRADEMARK OFFICE
CERTIFICATE OF CORRECTION

PATENT NO. : 5,498,521

DATED : MARCH 12, 1996

INVENTOR(S) : THADDEUS P. DRYJA AND ELIOT L. BERSON

It is certified that error appears in the above-indentified patent and that said Letters Patent is hereby corrected as shown below:

TITLE PAGE

Page 2, under "OTHER PUBLICATIONS", column 2, line 7 from the bottom, correct the spelling of "accumulation";

Column 1, line 11, "U.S. Patent No. 5,335,546" should be replaced with --U.S. Patent No. 5,225,546--;

Column 2, line 19, replace "$\gamma$-subunit" with --ß-subunit--;

Column 4, line 61, correct the spelling of "utilized";

Column 13, line 30, replace "10.9 X 106 clones" with --10.9 X $10^6$ clones--;

Column 13, line 60, replace "ADS" with --AD8--;

Column 16, line 63, replace "PDE ß" with --PDE $\alpha$--;

Column 17, line 43, correct the spelling of "patients";

UNITED STATES PATENT AND TRADEMARK OFFICE
CERTIFICATE OF CORRECTION

PATENT NO. : 5,498,521
DATED : March 12, 1996
INVENTOR(S) : THADDEUS P. DRYJA AND ELIOT L. BERSON It is certified that error appears in the above-indentified patent and that said Letters Patent is hereby corrected as shown below:

Columns 33-34, "Sequence ID No. 11", correct the spelling of "single".

Signed and Sealed this

Third Day of September, 1996

Attest:

BRUCE LEHMAN

Attesting Officer

Commissioner of Patents and Trademarks